(12) United States Patent
Blake et al.

(10) Patent No.: US 12,152,040 B2
(45) Date of Patent: Nov. 26, 2024

(54) TERT-BUTYL (S)-2-(4-(PHENYL)-6H-THIENO[3, 2-F][1, 2, 4]TRIAZOLO[4, 3-A][1,4]DIAZEPIN-6-YL) ACETATE DERIVATIVES AND RELATED COMPOUNDS AS BROMODOMAIN BRD4 INHIBITORS FOR TREATING CANCER

(71) Applicant: Genentech, Inc., South San Francisco, CA (US)

(72) Inventors: Robert Anthony Blake, South San Francisco, CA (US); Peter Dragovich, South San Francisco, CA (US); Lewis J. Gazzard, South San Francisco, CA (US); Susan Kaufman, South San Francisco, CA (US); Tracy Kleinheinz, South San Francisco, CA (US); Thomas Pillow, South San Francisco, CA (US); Steven T. Staben, South San Francisco, CA (US); Binqing Wei, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 880 days.

(21) Appl. No.: 17/198,240

(22) Filed: Mar. 10, 2021

(65) Prior Publication Data
US 2021/0221821 A1    Jul. 22, 2021

Related U.S. Application Data

(63) Continuation of application No. PCT/US2019/050576, filed on Sep. 11, 2019.

(60) Provisional application No. 62/729,679, filed on Sep. 11, 2018.

(51) Int. Cl.
*C07D 495/14*    (2006.01)
*A61P 35/00*    (2006.01)
*C07D 495/16*    (2006.01)

(52) U.S. Cl.
CPC .......... *C07D 495/14* (2013.01); *A61P 35/00* (2018.01); *C07D 495/16* (2013.01)

(58) Field of Classification Search
CPC ...... C07D 495/14; C07D 495/16; A61P 35/00
See application file for complete search history.

(56) References Cited

U.S. PATENT DOCUMENTS 10,772,962 B2 *    9/2020    Qian ................. A61K 45/06

FOREIGN PATENT DOCUMENTS

| WO | 2011/054845 A1 | 5/2011 |
|----|----------------|--------|
| WO | 2014/001356 A1 | 1/2014 |
| WO | 2015/081280 A1 | 6/2015 |
| WO | 2016/069578 A1 | 5/2016 |
| WO | 2017/030814 A1 | 2/2017 |
| WO | 2017/044849 A1 | 3/2017 |

OTHER PUBLICATIONS

Romero, F., et al., "Disrupting Acetyl-Lysine Recognition: Progress in the Development of Bromodomain Inhibitors" ACS J Med Chem (EPUB: Dec. 1, 2015), 59(4):1271-1298 (Feb. 25, 2016).
"International Preliminary Report on Patentability—PCT/US2019/050576" (Report Issuance Date: Mar. 9, 2021, Chapter I),: pp. 1-12 (Mar. 25, 2021).
"International Search Report—PCT/US2019/050576" (w/Written Opinion),: pp. 1-20 (Jan. 20, 2020).

* cited by examiner

*Primary Examiner* — Kamal A Saeed

(57) ABSTRACT

The present disclosure relates to compounds and salts thereof that are useful for inhibiting target polypeptides and proteins, in particular, bromodomain (e.g., BRD4) proteins. Also disclosed are pharmaceutical compositions comprising the compounds, or a salt (e.g., a pharmaceutically acceptable salt) thereof, and methods of using such compounds and salts in the treatment of various bromodomain-mediated diseases or disorders.

31 Claims, No Drawings

TERT-BUTYL (S)-2-(4-(PHENYL)-6H-THIENO[3, 2-F][1, 2, 4]TRIAZOLO[4, 3-A][1,4]DIAZEPIN-6-YL) ACETATE DERIVATIVES AND RELATED COMPOUNDS AS BROMODOMAIN BRD4 INHIBITORS FOR TREATING CANCER

CROSS-REFERENCE TO RELATED APPLICATIONS

This application is a continuation of International Application No. PCT/US2019/050576 having an International filing date of Sep. 11, 2019 which claims priority to U.S. Provisional Application No. 62/729,679 filed Sep. 11, 2018, both of which are incorporated herein in their entirety.

BACKGROUND OF THE DISCLOSURE

The present disclosure relates to compounds and salts thereof that are useful for inhibiting target polypeptides and proteins, in particular, bromodomain (e.g., BRD4). In particular, the compounds bind to and inhibit and/or degrade the target protein (e.g., BET/BRD4). Also disclosed are pharmaceutical compositions comprising the compounds, or a salt (e.g., a pharmaceutically acceptable salt) thereof, and methods of using such compounds and their salts in the treatment of various bromodomain-mediated diseases or disorders.

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., Genes Dev., 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., Trends Biochem. Sci., 1997, 22, 5, 151-153; and Tamkun J. W., et al., Cell, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., Trends Pharm. Sci., 33(3):146-153 (2012) and Muller et al., Expert Rev., 13(29):1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. This is highlighted by the observation that mutations in bromodomain-containing proteins are linked to cancer, as well as immune and neurologic dysfunction. Moreover, recent findings have demonstrated that small molecule inhibition of the bromodomains of BRD4 may have clinical utility in diverse human diseases, ranging from auto-immunity to cardiac hypertrophy. This is possible because the underlying mechanism resides in transcriptional regulation. Hence, the selective inhibition of bromodomains across the family creates varied opportunities as novel therapeutic agents in human dysfunction.

There is thus a need for treatments for cancer, immunological disorders, and other bromodomain related diseases, and for compounds that can inhibit or degrade bromodomains, such as BRD4.

SUMMARY

The present disclosure is directed to compounds, and salts and enantiomers thereof, effective in the treatment of cancer, immunological disorders, and other bromodomain-mediated disorders through inhibition or degradation of bromodomain proteins, such as BRD4, or through other mechanisms of action.

The present disclosure is directed to a compound of Formula (I):

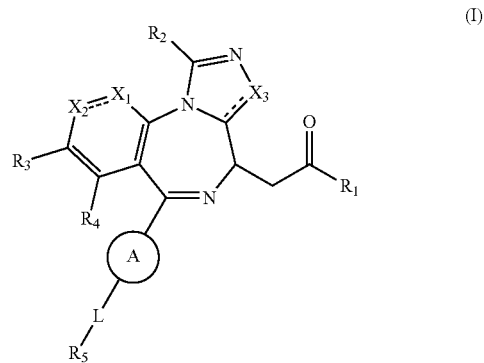

or a pharmaceutically acceptable salt or an enantiomer thereof, wherein:
$X_1$ is S or $C(R_{11})$;
$X_2$ is absent or $C(R_{12})$;
$X_3$ is N or O;

ring A is phenyl or a 6-membered heteroaryl, wherein ring A is optionally further substituted with one or more substituents selected from the group consisting of halo, hydroxy, —$C_{1-3}$-alkyl, —O—$C_{1-3}$-alkyl, and —$NH_2$;
$R_1$ is —O—$C_1$-$C_6$-alkyl, or —$N(R_8)(R_9)$;
$R_2$ is methyl;
$R_3$, $R_4$, $R_{11}$, and $R_{12}$ are each independently selected from the group consisting of H, methyl, and methoxy;
$R_5$ is selected from the group consisting of —$N(R_6)(R_7)$; —C(H)($CH_3$)—$NH_2$; —C($CH_3$)$_2$—$NH_2$; methyl; and hydroxy;
$R_6$ and $R_7$ are independently selected from the group consisting of H, methyl, —C(NH)—$NH_2$, hydroxy, and —C(O)$CH_3$;
$R_8$ and $R_9$ are independently selected from the group consisting of H, $C_1$-$C_4$-alkyl, and phenyl, wherein the phenyl is optionally substituted with $R_{10}$;
$R_{10}$ is hydroxy;
L is $C_1$-$C_4$ alkylene, $C_2$-$C_4$ alkenylene or $C_2$-$C_4$ alkynylene; and
═══ is a single or a double bond; wherein when $X_1$ is C($R_{11}$), ═══ is a double bond between $X_1$ and $X_2$, and when $X_3$ is N, ═══ is a double bond between $X_3$ and the rest of the molecule.

In an embodiment, the present disclosure is directed to a compound of Formula (I), or a pharmaceutically acceptable salt thereof, wherein $R_5$ is —$N(R_6)(R_7)$; $R_6$ and $R_7$ are independently selected from the group consisting of H, methyl, —C(NH)—$NH_2$, and hydroxy; and L is a $C_3$-$C_4$ alkenylene or a $C_3$-$C_4$ alkynylene.

In another embodiment, the present disclosure is directed to a compound of Formula (Ia) or (Ib):

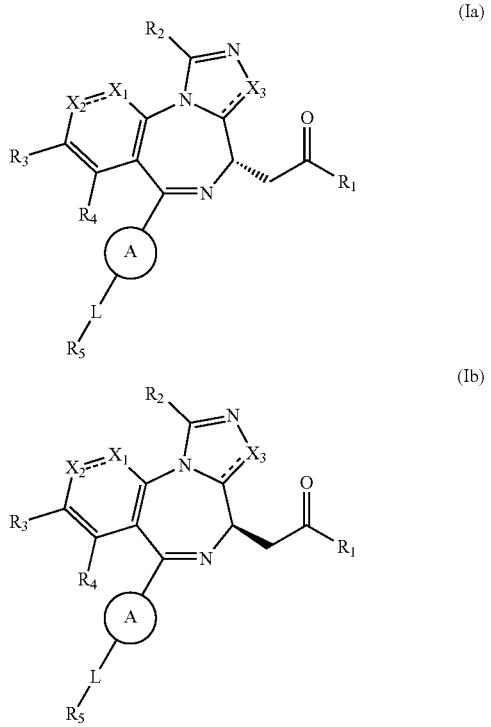

or a pharmaceutically acceptable salt thereof; wherein $R_1$, $R_2$, $R_3$, $R_4$, $R_5$, ring A, L, and ═══ are as defined for Formula (I).

In another embodiment, the present disclosure is directed to a pharmaceutical composition comprising a compound of the present disclosure (e.g., a compound of Formula (I)), or a salt (e.g., a pharmaceutically acceptable salt) thereof, and one or more pharmaceutically acceptable excipients. In one embodiment, the pharmaceutical composition further comprises an additional bioactive agent.

In another embodiment, the present disclosure is directed to a method of treating a disease or disorder in a human in need thereof, the method comprising administering to said human an effective amount of a compound of the present disclosure (e.g., a compound of Formula (I)), or a salt (e.g., a pharmaceutically acceptable salt) thereof, or a composition comprising said compound or salt. In one embodiment, the disease or disorder is a bromodomain-mediated disorder.

In another embodiment, the present disclosure is directed to a method of degrading a bromodomain-containing protein in a cell, the method comprising exposing the cell to a composition comprising an effective amount of a compound of the present disclosure (e.g., a compound of Formula (I)), or a salt (e.g., a pharmaceutically acceptable salt) thereof, wherein the compound effectuates the degradation of the bromodomain-containing protein. In one embodiment, the bromodomain-containing protein is bromodomain-containing protein 4 (BRD4).

DETAILED DESCRIPTION OF THE DISCLOSURE

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers alternatives, modifications, and equivalents. In the event that one or more of the incorporated literature, patents, and similar materials differs from or contradicts this application, including but not limited to defined terms, term usage, described techniques, or the like, this application controls. Unless otherwise defined, technical and scientific terms used herein have the same meaning as commonly understood by one of ordinary skill in the art to which this disclosure belongs, applying that term in context to its use in describing the present disclosure. The terminology used in the description is for describing particular embodiments only and is not intended to be limiting of the disclosure. All publications, patent applications, patents, and other references mentioned herein are incorporated by reference in their entirety.

I. Definitions

The terms "moiety" or "group" refers to a component that is covalently bound or linked to another component.

The term "covalently bound" or "covalently linked" refers to a chemical bond formed by sharing of one or more pairs of electrons.

A "patient" or an "individual" or a "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer.

The term "cancer" refers to or describes the physiological condition in mammals that is typically characterized by unregulated cell growth/proliferation. In particular, the term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. A "tumor" comprises one or more cancerous cells. Examples of cancer are provided elsewhere herein.

A "chemotherapeutic agent" or "anti-cancer agent" refers to a chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylomithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (RI1577); orafenib, ABT510; Bcl-2 inhibitor such as oblimersen sodium (GENASENSE®, an antisence oligonucleotide); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafamib (SCH 6636, SARASAR™);

and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the compounds and compositions of the subject matter described herein are used to delay development of a disease or to slow the progression of a disease. In one embodiment, treatment is performed for prophylaxis only. In an embodiment, treatment is performed during the course of clinical pathology only (i.e., not for prophylaxis). In an embodiment, treatment is performed both during the course of clinical pathology and for prophylaxis.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

The term "effective" is used to describe an amount of a compound, composition or component which, when used within the context of its intended use, achieves the desired therapeutic or prophylactic result. The term effective subsumes other effective amount or effective concentration terms, which are otherwise described or used in the present application. As used herein, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a compound of the present disclosure, as well as salts thereof, may be administered as the raw chemical. Additionally, the active ingredient may be presented as a pharmaceutical composition.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted", "optionally further substituted" or variations thereof denote an optional substitution, including multiple degrees of substitution, with one or more substituent group, for example, one, two, three, four or five. The phrase should not be interpreted as duplicative of the substitutions herein described and depicted.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

The phrase "pharmaceutically acceptable salt," as used herein, refers to pharmaceutically acceptable organic or inorganic salts of a molecule. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1'-methylene bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds described herein and these should be considered to form a further aspect of the subject matter. These salts, such as oxalic or trifluoroacetate, while not in themselves pharmaceutically acceptable, may be useful in the preparation of salts useful as intermediates in obtaining the compounds described herein and their pharmaceutically acceptable salts.

A "small molecule" generally refers to an organic molecule that is less than about 5 kilodaltons (Kd) in size. In some embodiments, the small molecule is less than about 4 Kd, 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. Small molecules are not proteins, polypeptides, oligopeptides, peptides, polynucleotides, oligonucleotides, polysaccharides, glycoproteins, proteoglycans, etc. A derivative of a small molecule refers to a molecule that shares the same structural core as the original small molecule, but which can be prepared by a series of chemical reactions from the original small molecule.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described herein. In an embodiment, an alkyl radical is one to eight carbon atoms ($C_1$-$C_8$), or one to six carbon atoms ($C_1$-$C_6$), or one to four carbon atoms ($C_1$-$C_4$), or one to three carbon atoms ($C_1$-$C_3$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, isopropyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, tert-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described herein. In an embodiment, an alkylene radical is one to eight carbon atoms ($C_1$-$C_8$), one to six carbon atoms ($C_1$-$C_6$), one to four carbon atoms ($C_1$-$C_4$), or two to four carbon atoms ($C_2$-$C_4$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of any length from two to twelve carbon atoms ($C_2$-$C_{12}$) with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkenylene" refers to linear or branched-chain divalent hydrocarbon radical of any length from two to twelve carbon atoms ($C_2$-$C_{12}$) with at least one site of unsaturation, i.e., a carbon-carbon, sp2 double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—$CH=CH$—), allyl (—$CH_2CH=CH$—), —$CH_2CH_2CH=CH$—, and the like.

The term "alkynyl" refers to a linear or branched monovalent hydrocarbon radical of any length from two to twelve carbon atoms ($C_2$-$C_{12}$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of any length from two to twelve carbon atoms ($C_2$-$C_{12}$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), —$CH_2CH_2$C≡C—, and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein. "Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described herein. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6]system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 3-carboline.

The term "methoxy" refers to —O—CH$_3$.

The term "hydroxy" refers to —OH.

The term "t-butyl" or "tBu" refers to tert-butyl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond ⚏ is shown, both a double bond and single bond are represented within the context of the compound shown.

As used herein a wavy line "⌇" that intersects a bond in a chemical structure indicate the point of attachment of the atom to which the wavy bond is connected in the chemical structure to the remainder of a molecule, or to the remainder of a fragment of a molecule In certain embodiments disclosed herein, certain groups (e.g., phenyl or heteroaryl) are described as "substituted". In some such embodiments, the "substituted" group may be substituted with 1, 2, 3, 4, 5, or more substituents, as indicated herein. In certain embodiments, certain groups may be substituted with one or more substituents independently selected from, but not limited to, alkyl, alkenyl, alkynyl, cycloalkyl, heterocyclyl, aryl, heteroaryl, halo (i.e., halogen), haloalkyl, oxo, OH, CN, —O-alkyl, S-alkyl, NH-alkyl, N(alkyl)$_2$, O-cycloalkyl, S-cycloalkyl, NH-cycloalkyl, N(cycloalkyl)$_2$, N(cycloalkyl)(alkyl), NH$_2$, SH, SO$_2$-alkyl, P(O)(O-alkyl)(alkyl), P(O)(O-alkyl)$_2$, Si(OH)$_3$, Si(alkyl)$_3$, Si(OH)(alkyl)$_2$, CO-alkyl, CO$_2$H, NO$_2$, SF$_5$, SO$_2$NH-alkyl, SO$_2$N(alkyl)$_2$, SONH-alkyl, SON(alkyl)$_2$, CONH-alkyl, CON(alkyl)$_2$, N(alkyl)CONH(alkyl), N(alkyl)CON(alkyl)$_2$, NHCONH(alkyl), NHCON(alkyl)$_2$, NHCONH$_2$, N(alkyl)SO$_2$NH(alkyl), N(alkyl) SO$_2$N (alkyl)$_2$, NHSO$_2$NH(alkyl), NHSO$_2$N(alkyl)$_2$, and NHSO$_2$NH$_2$.

Still additional definitions and abbreviations are provided elsewhere herein.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

In the claims, as well as in the specification above, transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

As indicated above, the description relates to a compounds or salts thereof that inhibit and/or degrade bromodomain proteins (e.g., BRD4). In some embodiments, the compounds or salts thereof bind to, inhibit, and/or degrade bromodomain proteins, and in particular, BRD4.

II. BRD4 Inhibitor Compounds

In one aspect, the present disclosure is directed to a compound of Formula (I):

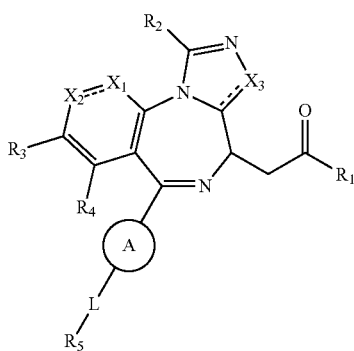

(I)

or a salt (e.g., a pharmaceutically acceptable salt) or an enantiomer thereof;
wherein:
$X_1$ is S or $C(R_{11})$;
$X_2$ is absent or $C(R_{12})$;
$X_3$ is N or O;
ring A is phenyl or a 6-membered heteroaryl, wherein ring A is optionally further substituted in an embodiment with one or more substituents selected from the group consisting of halo, hydroxy, —$C_{1-3}$-alkyl, —O—$C_{1-3}$-alkyl, and —$NH_2$;
$R_1$ is —O—$C_1$-$C_6$-alkyl, or —$N(R_8)(R_9)$;
$R_2$ is methyl;
$R_3$, $R_4$, $R_{11}$, and $R_{12}$ are each independently selected from the group consisting of H, methyl, and methoxy;
$R_5$ is selected from the group consisting of —$N(R_6)(R_7)$; —$C(H)(CH_3)$—$NH_2$; —$C(CH_3)_2$—$NH_2$; methyl; and hydroxy;
$R_6$ and $R_7$ are independently selected from the group consisting of H, methyl, —C(NH)—$NH_2$, hydroxy, and —$C(O)CH_3$;
$R_8$ and $R_9$ are independently selected from the group consisting of H, $C_1$-$C_4$-alkyl, and phenyl, wherein the phenyl is optionally substituted with $R_{10}$;
$R_{10}$ is hydroxy;
L is selected from the group consisting of a $C_1$-$C_4$ alkylene, a $C_2$-$C_4$ alkenylene, and a $C_2$-$C_4$ alkynylene; and
===== is a single or a double bond; wherein when $X_1$ is $C(R_{11})$, ===== is a double bond between $X_1$ and $X_2$, and when $X_3$ is N, ===== is a double bond between $X_3$ and the rest of the molecule.

In one embodiment the compound is a compound of Formula (I), or a salt (e.g., a pharmaceutically acceptable salt) thereof, wherein $X_1$, $X_2$, $X_3$, ring A, $R_1$, $R_2$, $R_3$, $R_4$, $R_5$, $R_6$, $R_7$, $R_8$, $R_9$, $R_{10}$, $R_{11}$, $R_{12}$, and ===== are as defined above for Formula (I), and wherein L is $C_2$-$C_4$ alkylene, $C_2$-$C_4$ alkenylene or a $C_2$-$C_4$ alkynylene.

In an embodiment, $R^5$ is selected from the group consisting of $CH_3$, OH, $NH_2$, $NH(CH_3)$, $N(CH_3)_2$, NH(OH), NH—$C(NH)(NH_2)$, NH—$C(O)(CH_3)$, $CH(CH_3)$—$NH_2$ and $C(CH_3)_2$—$NH_2$. In an embodiment, $R^5$ is selected from the group consisting of $NH_2$, $NH(CH_3)$, $N(CH_3)_2$, NH(OH), $CH(CH_3)$—$NH_2$ and NH—$C(NH)(NH_2)$.

In one embodiment the compound is a compound of Formula (I), or a salt (e.g., a pharmaceutically acceptable salt) thereof, wherein $X_1$, $X_2$, $X_3$, ring A, $R_1$, $R_2$, $R_3$, $R_4$, $R_8$, $R_9$, $R_{10}$, $R_{11}$, $R_{12}$, and ===== are as defined above for Formula (I), and wherein $R_5$ is —$N(R_6)(R_7)$; $R_6$ and $R_7$ are independently selected from the group consisting of H, methyl, —C(NH)—$NH_2$, and hydroxy; and L is $C_3$-$C_4$ alkylene, $C_3$-$C_4$ alkenylene or a $C_3$-$C_4$ alkynylene.

In one aspect, the present disclosure is directed to a compound of Formula (Ia) or (Ib):

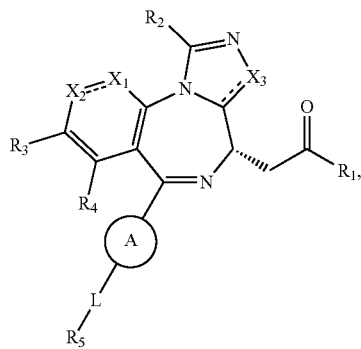

(Ia)

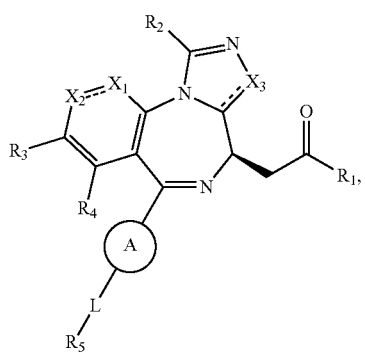

(Ib)

or a salt (e.g., a pharmaceutically acceptable salt) thereof;
wherein $X_1$, $X_2$, $X_3$, ring A, $R_1$, $R_2$, $R_3$, $R_4$, $R_5$, L, and ===== are as defined above for Formula (I).

In one embodiment, the compound is a compound of Formula (Ia) or (Ib), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In an embodiment, the compound is a compound of Formula (Ia) or (Ib), or a salt (e.g., a pharmaceutically acceptable salt) thereof, wherein $R^5$ is selected from the group consisting of $CH_3$, OH, $NH_2$, $NH(CH_3)$, $N(CH_3)_2$, NH(OH), NH—$C(NH)(NH_2)$, NH—$C(O)(CH_3)$, $CH(CH_3)$—$NH_2$ and $C(CH_3)_2$—$NH_2$. In an embodiment, $R^5$ is selected from the group consisting of $NH_2$, $NH(CH_3)$, $N(CH_3)_2$, NH(OH), $CH(CH_3)$—$NH_2$ and NH—$C(NH)$$(NH_2)$.

In one embodiment, the compound is a compound of Formula (Ia) or (Ib), or a salt (e.g., a pharmaceutically acceptable salt) thereof, wherein $R_5$ is —$N(R_6)(R_7)$; $R_6$ and $R_7$ are independently selected from the group consisting of H, methyl, —C(NH)—$NH_2$, and hydroxy; and L is a $C_3$-$C_4$ alkylene, a $C_3$-$C_4$ alkenylene or a $C_3$-$C_4$ alkynylene.

In embodiments, the compound is a compound of Formula (Ia) or (Ib), or a salt (e.g., a pharmaceutically acceptable salt) thereof, wherein L is $C_1$-$C_4$ alkylene, $C_2$-$C_4$ alkenylene or $C_2$-$C_4$ alkynylene; and $R_5$ is selected from the group consisting of —$N(R_6)(R_7)$, wherein $R_6$ and $R_7$ are independently selected from the group consisting of H, methyl, —C(NH)—$NH_2$, and hydroxy.

In one embodiment, the compound is a compound of Formula (I), (Ia), or (Ib), or a salt (e.g., a pharmaceutically acceptable salt) thereof, wherein ring A is further substituted with 1, 2, 3, or 4 $R_{13}$ groups, wherein each $R_{13}$ group is independently selected from the group consisting of H, halo, hydroxy, —$C_{1-3}$-alkyl, —O—$C_{1-3}$-alkyl, and —$NH_2$, or is independently selected from the group consisting of H and halo.

In one embodiment, the compound is a compound of Formula (I), (Ia), or (Ib), or a salt (e.g., a pharmaceutically acceptable salt) thereof, wherein ring A is selected from the group consisting of phenyl, pyridinyl, and pyrimidinyl.

In one embodiment, the compound is a compound of Formula (I), (Ia), or (Ib), or a salt (e.g., a pharmaceutically acceptable salt) thereof, wherein ring A is a 6-membered heteroaryl, wherein the 6-membered heteroaryl is optionally further substituted. In one particular embodiment, the 6-membered heteroaryl is selected from the group consisting of optionally substituted pyridinyl and optionally substituted pyrimidinyl.

In one embodiment, the compound is a compound of Formula (I), (Ia), or (Ib), or a salt (e.g., a pharmaceutically acceptable salt) thereof, wherein ring A is a 6-membered heteroaryl, and the 6-membered heteroaryl, taken together with L and $R_5$, is selected from the group consisting of:

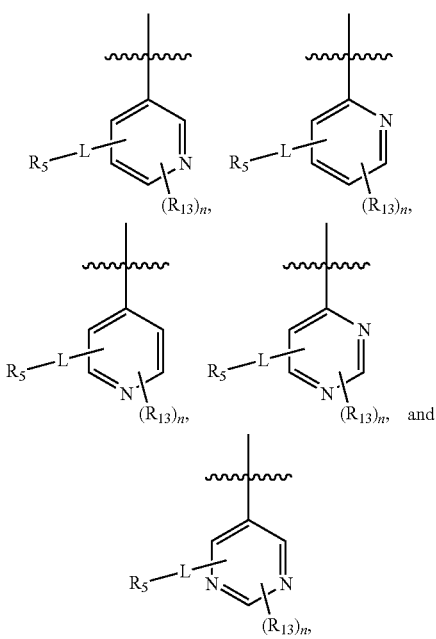

wherein $R_5$, $R_{13}$, and L are as defined above for Formulas (I), (Ia), or (Ib), and n is 0, 1, 2, or 3. In one particular embodiment, ring A, taken together with L and $R_5$, is

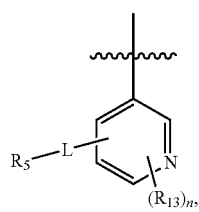

wherein $R_5$, $R_{13}$, and L are as defined above for Formulas (I), (Ia), or (Ib), and n is 0, 1, 2, or 3.

In one embodiment, the compound is a compound of Formula (I), (Ia), or (Ib), or a salt (e.g., a pharmaceutically acceptable salt) thereof, wherein ring A is a 6-membered heteroaryl, and the 6-membered heteroaryl, taken together with L and $R_5$, is selected from the group consisting of:

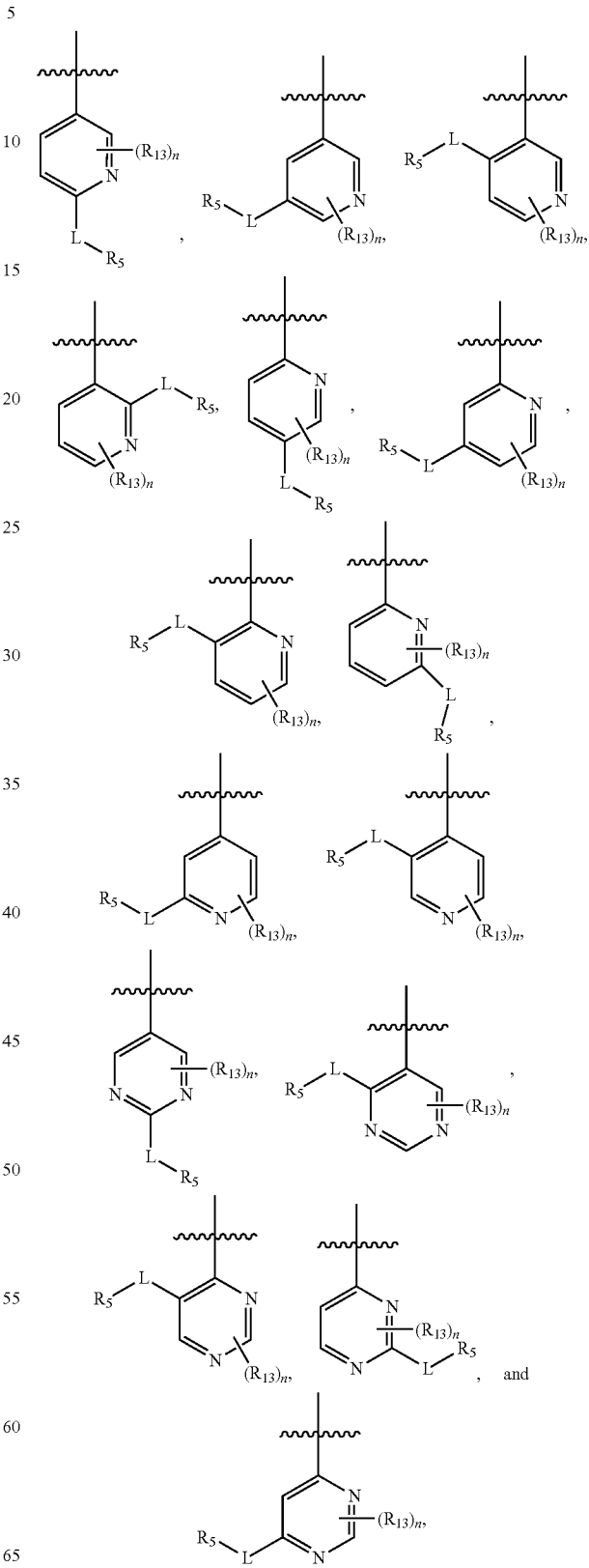

wherein L, $R_5$, and $R_{13}$, are as defined above for Formula (I), (Ia), or (Ib), and n is 0, 1, 2, or 3. In one particular embodiment, ring A, taken together with L and $R_5$, is

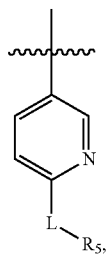

where L and $R_5$ are as defined above for Formula (I), (Ia), or (Ib).

In one embodiment, the compound is a compound of Formula (I), (Ia), or (Ib), or a salt (e.g., a pharmaceutically acceptable salt) thereof, wherein ring A is phenyl, wherein the phenyl is optionally further substituted. In one embodiment, ring A, taken together with L and $R_5$, is selected from the group consisting of:

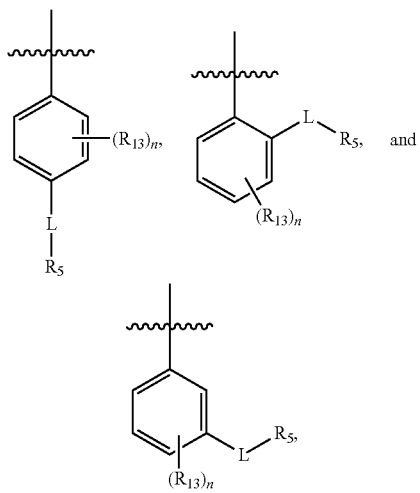

wherein $R_5$, $R_{13}$, and L are as defined above for Formula (I), (Ia), or (Ib), and n is 0, 1, 2, 3, or 4.

In one embodiment, the compound is a compound of Formula (I), (Ia), or (Ib), or a salt (e.g., a pharmaceutically acceptable salt) thereof, wherein ring A, taken together with L and $R_5$, is selected from the group consisting of

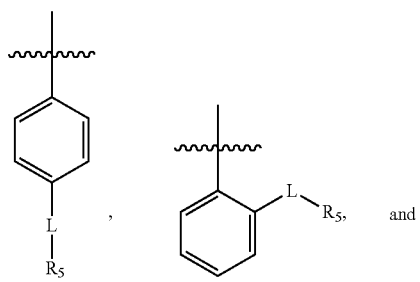

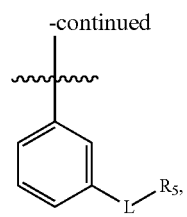

wherein $R_5$, $R_{13}$, and L are as defined above for Formula (I), (Ia), or (Ib).

In one embodiment, the compound is a compound of Formula (I), (Ia), or (Ib), or a salt (e.g., a pharmaceutically acceptable salt) thereof, wherein ring A, taken together with L and $R_5$, is

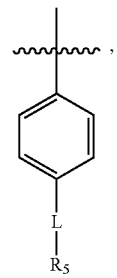

wherein L and $R_5$ are as defined above for Formula (I), (Ia), or (Ib).

In one embodiment, the compound is a compound of Formula (I), or a salt (e.g., a pharmaceutically acceptable salt) thereof, wherein $X_1$ is S, and $X_2$ is absent. For example, in one particular embodiment, the compound is a compound of Formula (II):

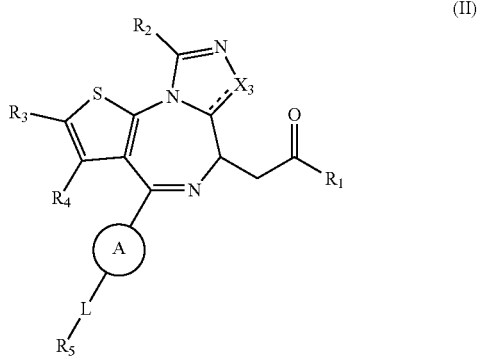

or a salt (e.g., a pharmaceutically acceptable salt) or an enantiomer thereof;

wherein $X_3$, ring A, $R_1$, $R_2$, $R_3$, $R_4$, $R_5$, L, and ===== are as defined above for Formula (I).

In an embodiment, the compound is a compound of Formula (IIa) or (IIb):

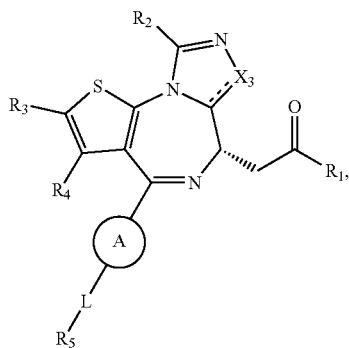

(IIa)

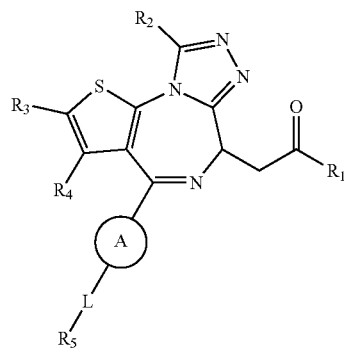

(III)

or a salt (e.g., a pharmaceutically acceptable salt) or an enantiomer thereof;

wherein ring A, $R_1$, $R_2$, $R_3$, $R_4$, $R_5$, and L are as defined above for Formula (I).

In an embodiment, the compound is a compound of Formula (IIIa) or (IIIb):

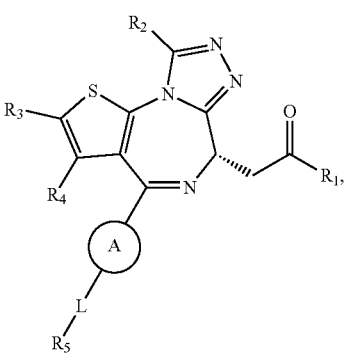

(IIIa)

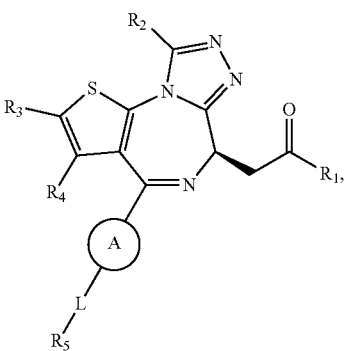

(IIIb)

(IIb)

or a salt (e.g., a pharmaceutically acceptable salt) thereof;

wherein $X_3$, ring A, $R_1$, $R_2$, $R_3$, $R_4$, $R_5$, L, and ----- are as defined above for Formula (I).

In one embodiment, the compound is a compound of Formula (II), (IIa), (IIb), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In another embodiment, the compound is a compound of Formula (II), (IIa), (IIb), or a salt (e.g., a pharmaceutically acceptable salt) thereof, wherein $R_5$ is —N($R_6$)($R_7$); $R_6$ and $R_7$ are independently selected from the group consisting of H, methyl, —C(NH)—$NH_2$, and hydroxy; and L is a $C_3$-$C_4$ alkylene, a $C_3$-$C_4$ alkenylene or a $C_3$-$C_4$ alkynylene.

In an embodiment, the compound is a compound of Formula (II), (IIa), (IIb), or a salt (e.g., a pharmaceutically acceptable salt) thereof, wherein $R^5$ is selected from the group consisting of $CH_3$, OH, $NH_2$, $NH(CH_3)$, $N(CH_3)_2$, NH(OH), NH—C(NH)($NH_2$), NH—C(O)($CH_3$), CH($CH_3$)—$NH_2$ and C($CH_3$)$_2$—$NH_2$. In an embodiment, $R^5$ is selected from the group consisting of $NH_2$, $NH(CH_3)$, $N(CH_3)_2$, NH(OH), CH($CH_3$)—$NH_2$ and NH—C(NH)($NH_2$).

In one embodiment, the compound is a compound of Formula (I), or a salt (e.g., a pharmaceutically acceptable salt) thereof, wherein $X_1$ is S; $X_2$ is absent; $X_3$ is N; and ----- is a double bond. For example, in one particular embodiment, the compound is a compound of Formula (III):

or a salt (e.g., a pharmaceutically acceptable salt) thereof; wherein ring A, $R_1$, $R_2$, $R_3$, $R_4$, $R_5$, and L are as defined above for Formula (I).

In one embodiment, the compound is a compound of Formula (III), (IIIa), (IIIb), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In an embodiment, the compound is a compound of Formula (III), (IIIa), (IIIb), or a salt (e.g., a pharmaceutically acceptable salt) thereof, wherein $R^5$ is selected from the group consisting of $CH_3$, OH, $NH_2$, $NH(CH_3)$, $N(CH_3)_2$, NH(OH), NH—C(NH)($NH_2$), NH—C(O)($CH_3$), CH($CH_3$)—$NH_2$ and C($CH_3$)$_2$—$NH_2$. In an embodiment, $R^5$ is selected from the group consisting of NH$_2$, NH(CH$_3$), N(CH$_3$)$_2$, NH(OH), CH(CH$_3$)—NH$_2$ and NH—C(NH)(NH$_2$).

In another embodiment, the compound is a compound of Formula (III), (IIIa), (IIIb), or a salt (e.g., a pharmaceutically acceptable salt) thereof, wherein R$_5$ is —N(R$_6$)(R$_7$); R$_6$ and R$_7$ are independently selected from the group consisting of H, methyl, —C(NH)—NH$_2$, and hydroxy; and L is a C$_3$-C$_4$ alkylene, a C$_3$-C$_4$ alkenylene or a C$_3$-C$_4$ alkynylene.

In one embodiment, the compound is a compound of Formula (I), or a salt (e.g., a pharmaceutically acceptable salt) thereof, wherein X$_1$ is S; X$_2$ is absent; X$_3$ is N; ring A is phenyl, wherein the phenyl may optionally be further substituted; and ====== is a double bond.

For example, in one particular embodiment, the compound is a compound of Formula (IV):

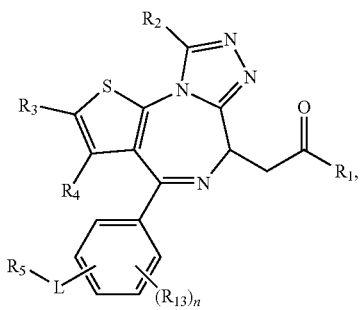
(IV)

or a salt (e.g., a pharmaceutically acceptable salt) or an enantiomer thereof;
wherein R$_1$, R$_2$, R$_3$, R$_4$, R$_5$, R$_{13}$, L, and n are as defined above for Formula (I).

In one particular embodiment, the compound is a compound of Formula (IV-1):

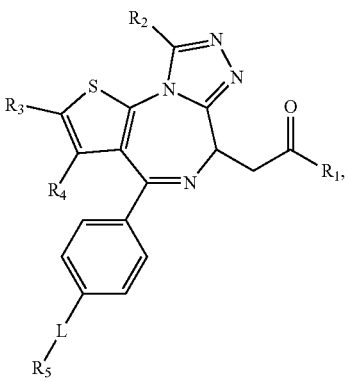
(IV-1)

or a salt (e.g., a pharmaceutically acceptable salt) or an enantiomer thereof;
wherein R$_1$, R$_2$, R$_3$, R$_4$, R$_5$, and L are as defined above for Formula (I).

In another embodiment, the compound is a compound of Formula (IVa) or (IVb):

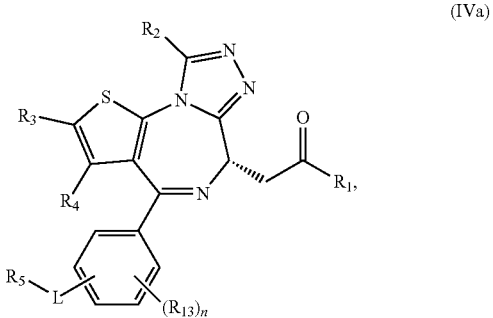
(IVa)

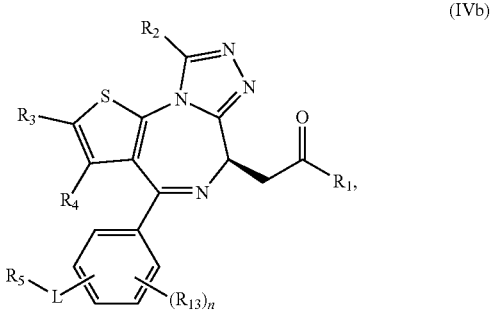
(IVb)

or a salt (e.g., a pharmaceutically acceptable salt) thereof;
wherein R$_1$, R$_2$, R$_3$, R$_4$, R$_5$, R$_{13}$, L, and n are as defined above for Formula (I).

In another embodiment, the compound is a compound of Formula (IV-1a) or (IV-1b):

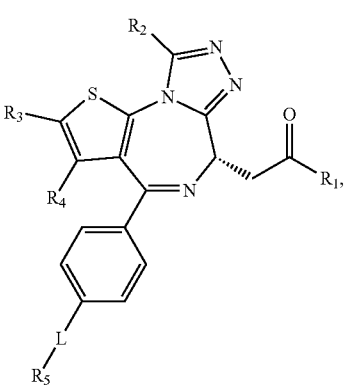
(IV-1a)

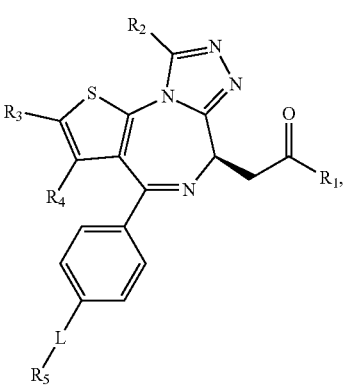
(IV-1b)

or a salt (e.g., a pharmaceutically acceptable salt) thereof;

wherein $R_1$, $R_2$, $R_3$, $R_4$, $R_5$, and L are as defined above for Formula (I).

In one embodiment, the compound is a compound of Formula (IV), (IV-1), (IVa), (IVb), (IV-1a), or (IV-1b), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In an embodiment, the compound is a compound of Formula (IV), (IV-1), (IVa), (IVb), (IV-1a), or (IV-1b), or a salt (e.g., a pharmaceutically acceptable salt) thereof, wherein $R^5$ is selected from the group consisting of $CH_3$, OH, $NH_2$, $NH(CH_3)$, $N(CH_3)_2$, $NH(OH)$, NH—C(NH)($NH_2$), NH—C(O)($CH_3$), $CH(CH_3)$—$NH_2$ and $C(CH_3)_2$—$NH_2$. In an embodiment, $R^5$ is selected from the group consisting of $NH_2$, $NH(CH_3)$, $N(CH_3)_2$, $NH(OH)$, $CH(CH_3)$—$NH_2$ and NH—C(NH)($NH_2$).

In an embodiment, the compound is a compound of Formula (IV), (IV-1), (IVa), (IVb), (IV-1a), or (IV-1b), or a salt (e.g., a pharmaceutically acceptable salt) thereof, wherein $R_5$ is —N($R_6$)($R_7$); $R_6$ and $R_7$ are independently selected from the group consisting of H, methyl, —C(NH)—$NH_2$, and hydroxy; and L is a $C_3$-$C_4$ alkylene, a $C_3$-$C_4$ alkenylene or a $C_3$-$C_4$ alkynylene.

In one embodiment, the compound is a compound of Formula (I), or a salt (e.g., a pharmaceutically acceptable salt) thereof, wherein $X_1$ is S; $X_2$ is absent; $X_3$ is O; and ----- is a single bond. For example, in one particular embodiment, the compound is a compound of Formula (V):

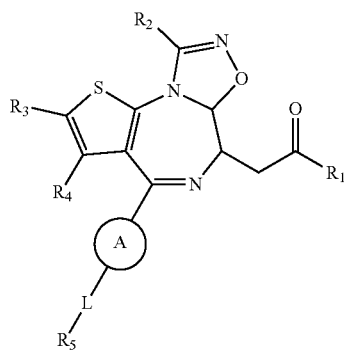

(V)

or a salt (e.g., a pharmaceutically acceptable salt) or an enantiomer thereof;
wherein ring A, $R_1$, $R_2$, $R_3$, $R_4$, $R_5$, and L are as defined above for Formula (I).

In another embodiment, the compound is a compound of Formula (Va) or (Vb):

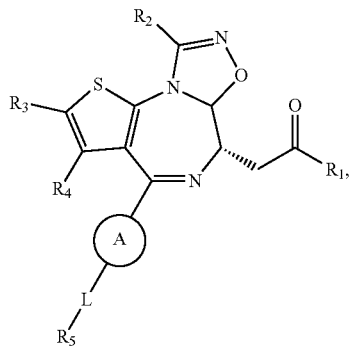

(Va)

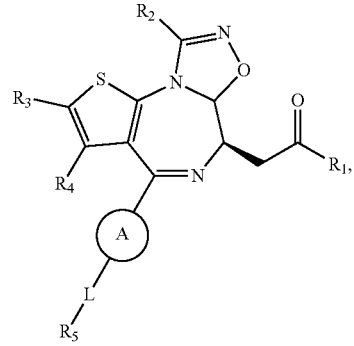

(Vb)

or a salt (e.g., a pharmaceutically acceptable salt) thereof;
wherein ring A, $R_1$, $R_2$, $R_3$, $R_4$, $R_5$, and L are as defined above for Formula (I).

In one embodiment, the compound is a compound of Formula (V), (Va), (Vb), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In an embodiment, the compound is a compound of Formula (V), (Va), (Vb), or a salt (e.g., a pharmaceutically acceptable salt) thereof, wherein $R^5$ is selected from the group consisting of $CH_3$, OH, $NH_2$, $NH(CH_3)$, $N(CH_3)_2$, $NH(OH)$, NH—C(NH)($NH_2$), NH—C(O)($CH_3$), $CH(CH_3)$—$NH_2$ and $C(CH_3)_2$—$NH_2$. In an embodiment, $R^5$ is selected from the group consisting of $NH_2$, $NH(CH_3)$, $N(CH_3)_2$, $NH(OH)$, $CH(CH_3)$—$NH_2$ and NH—C(NH)($NH_2$).

In another embodiment, the compound is a compound of Formula (V), (Va), (Vb), or a salt (e.g., a pharmaceutically acceptable salt) thereof, wherein $R_5$ is —N($R_6$)($R_7$); $R_6$ and $R_7$ are independently selected from the group consisting of H, methyl, —C(NH)—$NH_2$, and hydroxy; and L is a $C_3$-$C_4$ alkylene, a $C_3$-$C_4$ alkenylene or a $C_3$-$C_4$ alkynylene.

In one embodiment, the compound is a compound of Formula (I), or a salt (e.g., a pharmaceutically acceptable salt) thereof, wherein $X_1$ is S; $X_2$ is absent; $X_3$ is O; ring A is phenyl, wherein the phenyl may optionally be further substituted; and ----- is a single bond. For example, in one particular embodiment, the compound is a compound of Formula (VI):

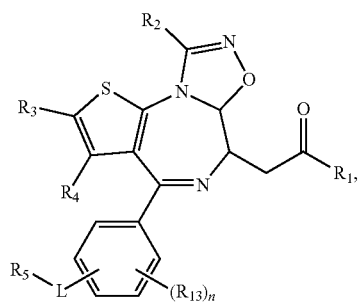

(VI)

or a salt (e.g., a pharmaceutically acceptable salt) or an enantiomer thereof;
wherein $R_1$, $R_2$, $R_3$, $R_4$, $R_5$, $R_{13}$, L, and n are as defined above for Formula (I).

In one particular embodiment, the compound is a compound of Formula (VI-1):

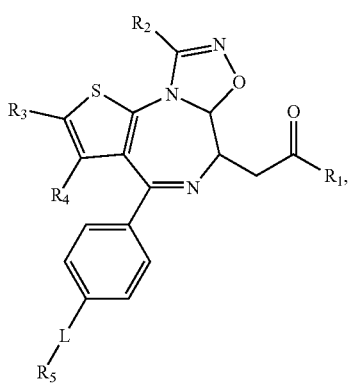

(VI-1)

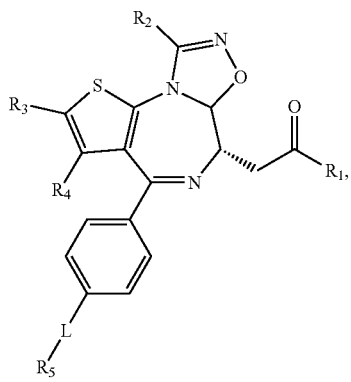

(VIa-1)

or a salt (e.g., a pharmaceutically acceptable salt) or an enantiomer thereof;

wherein $R_1$, $R_2$, $R_3$, $R_4$, $R_5$, and L are as defined above for Formula (I).

In another embodiment, the compound is a compound of Formula (VIa) or (VIb):

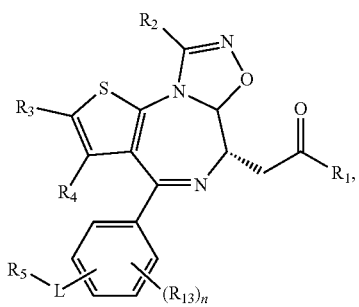

(VIa)

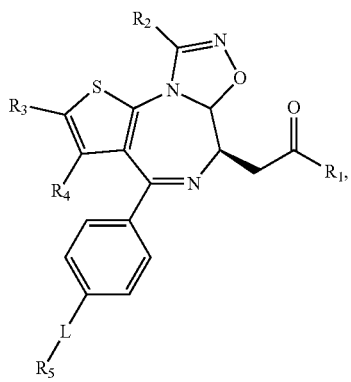

(VIb-1)

(VIb)

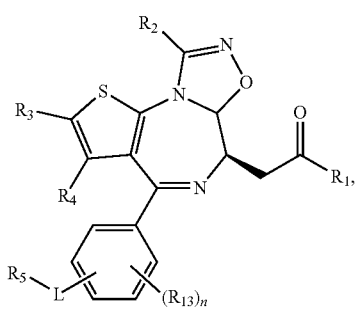

or a salt (e.g., a pharmaceutically acceptable salt) thereof;

wherein $R_1$, $R_2$, $R_3$, $R_4$, $R_5$, $R_{13}$, L, and n are as defined above for Formula (I).

In another embodiment, the compound is a compound of Formula (VI-1a) or (VI-1b):

or a salt (e.g., a pharmaceutically acceptable salt) thereof;

wherein $R_1$, $R_2$, $R_3$, $R_4$, $R_5$, and L are as defined above for Formula (I).

In one embodiment, the compound is a compound of Formula (VI), (VI-1), (VIa), (VIb), (VI-1a), or (VI-Ib), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In another embodiment, the compound is a compound of Formula (VI), (VI-1), (VIa), (VIb), (VI-1a), or (VI-1b), or a salt (e.g., a pharmaceutically acceptable salt) thereof, wherein $R_5$ is —N($R_6$)($R_7$); $R_6$ and $R_7$ are independently selected from the group consisting of H, methyl, —C(NH)—$NH_2$, and hydroxy; and L is a $C_3$-$C_4$ alkylene, a $C_3$-$C_4$ alkenylene or a $C_3$-$C_4$ alkynylene.

In one embodiment, the compound is a compound of Formula (I), or a salt (e.g., a pharmaceutically acceptable salt) thereof, wherein $X_1$ is C($R_{11}$) and $X_2$ is C($R_{12}$). For example, in one particular embodiment, the compound is a compound of Formula (VII):

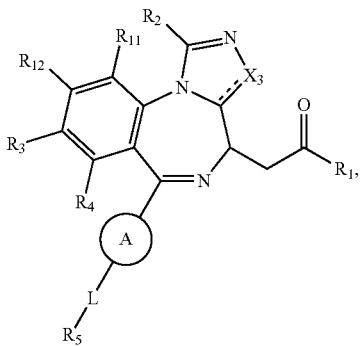

(VII)

or a salt (e.g., a pharmaceutically acceptable salt) or an enantiomer thereof;

wherein $R_1$, $R_2$, $R_3$, $R_4$, $R_5$, $R_{11}$, $R_{12}$, $R_{13}$, L, and ----- are as defined above for Formula (I).

In another embodiment, the compound is a compound of Formula (VIIa) or (VIIb):

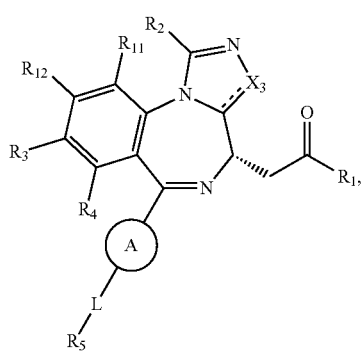

(VIIa)

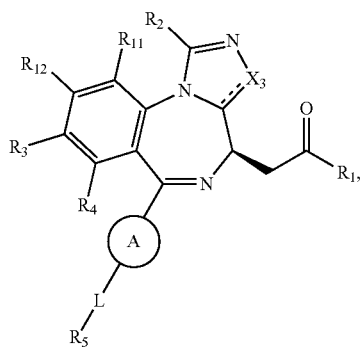

(VIIb)

or a salt (e.g., a pharmaceutically acceptable salt) thereof; wherein $R_1$, $R_2$, $R_3$, $R_4$, $R_5$, $R_{11}$, $R_{12}$, L, and ----- are as defined above for Formula (I).

In one embodiment, the compound is a compound of Formula (VII), (VIIa), (VIIb), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In another embodiment, the compound is a compound of Formula (VII), (VIIa), (VIIb), or a salt (e.g., a pharmaceutically acceptable salt) thereof, wherein $R_5$ is —N($R_6$)($R_7$); $R_6$ and $R_7$ are independently selected from the group consisting of H, methyl, —C(NH)—NH$_2$, and hydroxy; and L is a $C_3$-$C_4$ alkylene, a $C_3$-$C_4$ alkenylene or a $C_3$-$C_4$ alkynylene.

In one embodiment, the compound is a compound of Formula (I), or a salt (e.g., a pharmaceutically acceptable salt) thereof, wherein $X_1$ is C($R_1$), $X_2$ is C($R_{12}$), $X_3$ is N, and ----- is a double bond. For example, in one particular embodiment, the compound is a compound of Formula (VIII):

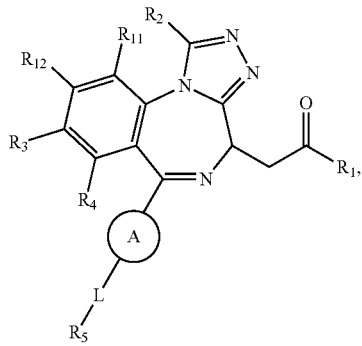

(VIII)

or a salt (e.g., a pharmaceutically acceptable salt) or an enantiomer thereof;

wherein $R_1$, $R_2$, $R_3$, $R_4$, $R_5$, $R_1$, $R_{12}$, and L are as defined above for Formula (I).

In another embodiment, the compound is a compound of Formula (VIIIa) or (VIIIb):

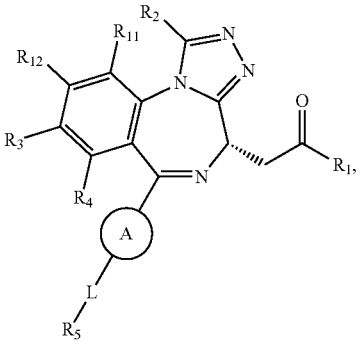

(VIIIa)

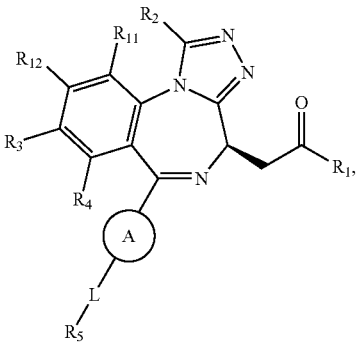

(VIIIb)

or a salt (e.g., a pharmaceutically acceptable salt) thereof; wherein $R_1$, $R_2$, $R_3$, $R_4$, $R_5$, $R_1$, $R_{12}$, and L are as defined above for Formula (I).

In one embodiment, the compound is a compound of Formula (VIII), (VIIIa), (VIIIb), or a salt (e.g., a pharmaceutically acceptable salt) thereof, wherein L is a $C_2$-$C_4$ alkylene, a $C_2$-$C_4$ alkenylene or a $C_2$-$C_4$ alkynylene.

In another embodiment, the compound is a compound of Formula (VIII), (VIIIa), (VIIIb), or a salt (e.g., a pharmaceutically acceptable salt) thereof, wherein $R_5$ is —N($R_6$)($R_7$); $R_6$ and $R_7$ are independently selected from the group consisting of H, methyl, —C(NH)—$NH_2$, and hydroxy; and L is a $C_3$-$C_4$ alkylene, a $C_3$-$C_4$ alkenylene or a $C_3$-$C_4$ alkynylene.

In one embodiment, the compound is a compound of Formula (I), or a salt (e.g., a pharmaceutically acceptable salt) thereof, wherein $X_1$ is C($R_{11}$); $X_2$ is C($R_{12}$); $X_3$ is N; ring A is phenyl, wherein the phenyl may optionally be further substituted; and ===== is a double bond. For example, in one particular embodiment, the compound is a compound of Formula (IX):

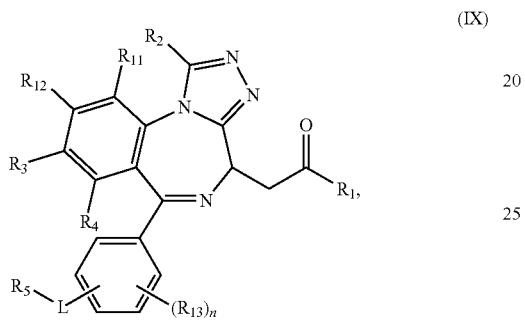
(IX)

or a salt (e.g., a pharmaceutically acceptable salt) or an enantiomer thereof;

wherein $R_1$, $R_2$, $R_3$, $R_4$, $R_5$, $R_1$, $R_{12}$, $R_{13}$, L, and n are as defined above for Formula (I).

In another embodiment, the compound is a compound of Formula (IX-1):

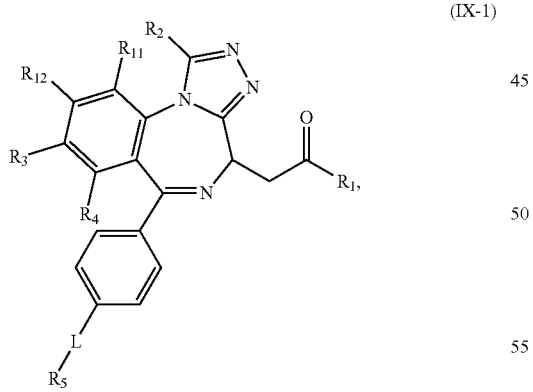
(IX-1)

or a salt (e.g., a pharmaceutically acceptable salt) or an enantiomer thereof;

wherein $R_1$, $R_2$, $R_3$, $R_4$, $R_5$, $R_1$, $R_{12}$, and L are as defined above for Formula (I).

In another embodiment, the compound is a compound of Formula (IXa) or (IXb):

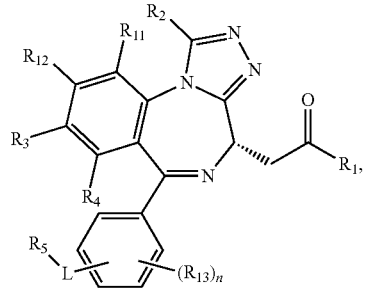
(IXa)

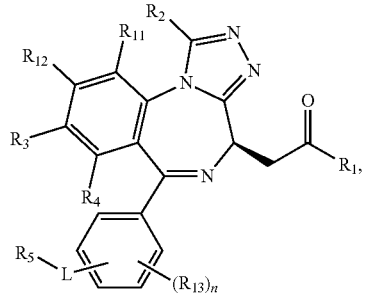
(IXb)

or a salt (e.g., a pharmaceutically acceptable salt) thereof; wherein $R_1$, $R_2$, $R_3$, $R_4$, $R_5$, $R_1$, $R_{12}$, $R_{13}$, L, and n are as defined above for Formula (I).

In another embodiment, the compound is a compound of Formula (IX-1a)(IX-Ib), (X), (Xa) or (Xb):

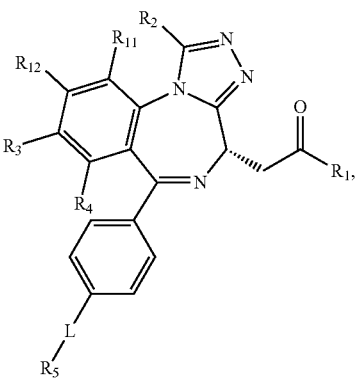
(IX-1a)

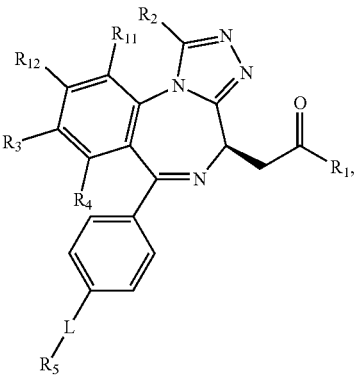
(IX-1b)

or a salt (e.g., a pharmaceutically acceptable salt) thereof; wherein $R_1$, $R_2$, $R_3$, $R_4$, $R_5$, $R_{11}$, $R_{12}$, and L are as defined above for Formula (I).

In one embodiment, the compound is a compound of Formula (IX), (IX-1), (IXa), (IXb), (IX-1a), (IX-1b), (X), (Xa) or (Xb), or a salt (e.g., a pharmaceutically acceptable salt) thereof, wherein L is $C_2$-$C_4$ alkylene, $C_2$-$C_4$ alkenylene or a $C_2$-$C_4$ alkynylene.

In an embodiment, the compound is a compound of Formula (IX), (IX-1), (IXa), (IXb), (IX-1a), (IX-1b), (X), (Xa) or (Xb), or a salt (e.g., a pharmaceutically acceptable salt) thereof, wherein $R_5$ is —N($R_6$)($R_7$); $R_6$ and $R_7$ are independently selected from the group consisting of H, methyl, —C(NH)—$NH_2$, and hydroxy; and L is $C_3$-$C_4$ alkylene, $C_3$-$C_4$ alkenylene or a $C_3$-$C_4$ alkynylene.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein $R_1$ is —O—$C_1$-$C_4$-alkyl. In one such embodiment, $R_1$ is —O-t-butyl. In another such embodiment, $R_1$ is —O—$CH_3$.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein $R_1$ is —N($R_8$)($R_9$). In one embodiment, $R_8$ and $R_9$ are each H. In an embodiment, $R_8$ is H and $R_9$ is $C_1$-$C_4$ alkyl. In still another embodiment, $R_8$ is H and $R_9$ is ethyl. In an embodiment, $R_8$ is H and $R_9$ is phenyl substituted with $R_{10}$.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein $R_1$ is —N($R_8$)($R_9$), $R_8$ is H and $R_9$ is phenyl substituted with $R_{10}$, and $R_{10}$ is hydroxy. In one embodiment, $R_9$ and $R_{10}$, taken together, are

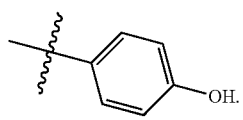 [SMILES: *c1ccc(O)cc1]

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein $R_3$ and $R_4$ are each methyl. In an embodiment, $R_3$ and $R_4$ are each H. In an embodiment, $R_3$ is methoxy and $R_4$ is H. In an embodiment, $R_3$ is H and $R_4$ is methoxy.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein $R_5$ is —N($R_6$)($R_7$). In one such embodiment, $R_6$ and $R_7$ are each H. In an embodiment, $R_6$ is H and $R_7$ is methyl. In an embodiment, $R_6$ and $R_7$ are each methyl. In an embodiment, $R_6$ is H and $R_7$ is —C(NH)—$NH_2$. In an embodiment, $R_6$ is H and $R_7$ is hydroxy. In an embodiment, $R_6$ is H and $R_7$ is —C(O)$CH_3$.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein $R_5$ is selected from the group consisting of —C(H)($CH_3$)—$NH_2$; —C($CH_3$)$_2$—$NH_2$; methyl; and hydroxy. In one such embodiment, $R_5$ is —C(H)($CH_3$)—$NH_2$. In another embodiment, $R_5$ is —C($CH_3$)$_2$—$NH_2$. In another embodiment, $R_5$ is methyl. In another embodiment, $R_5$ is hydroxy.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein L is a $C_3$-$C_4$ alkylene.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein L is a $C_3$-$C_4$ alkenylene.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein L is a $C_3$-$C_4$ alkynylene.

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein L and $R_5$, taken together, are selected from the group consisting of:

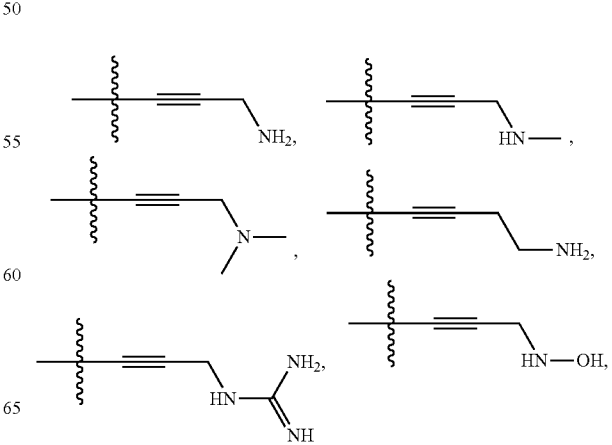

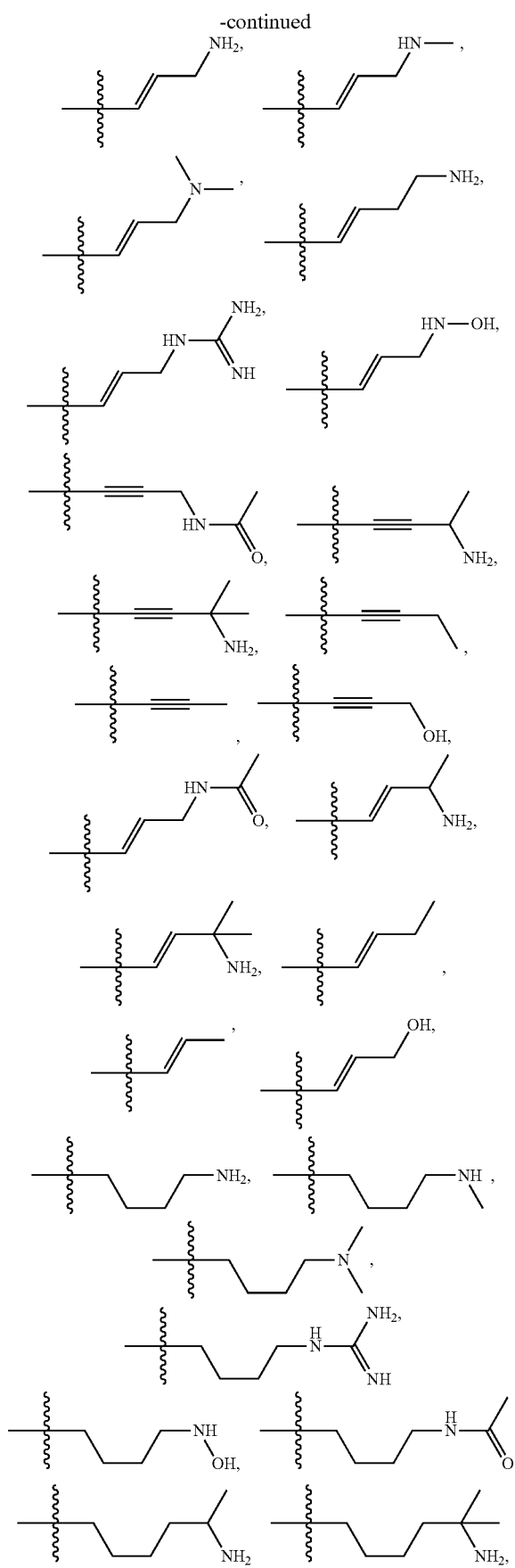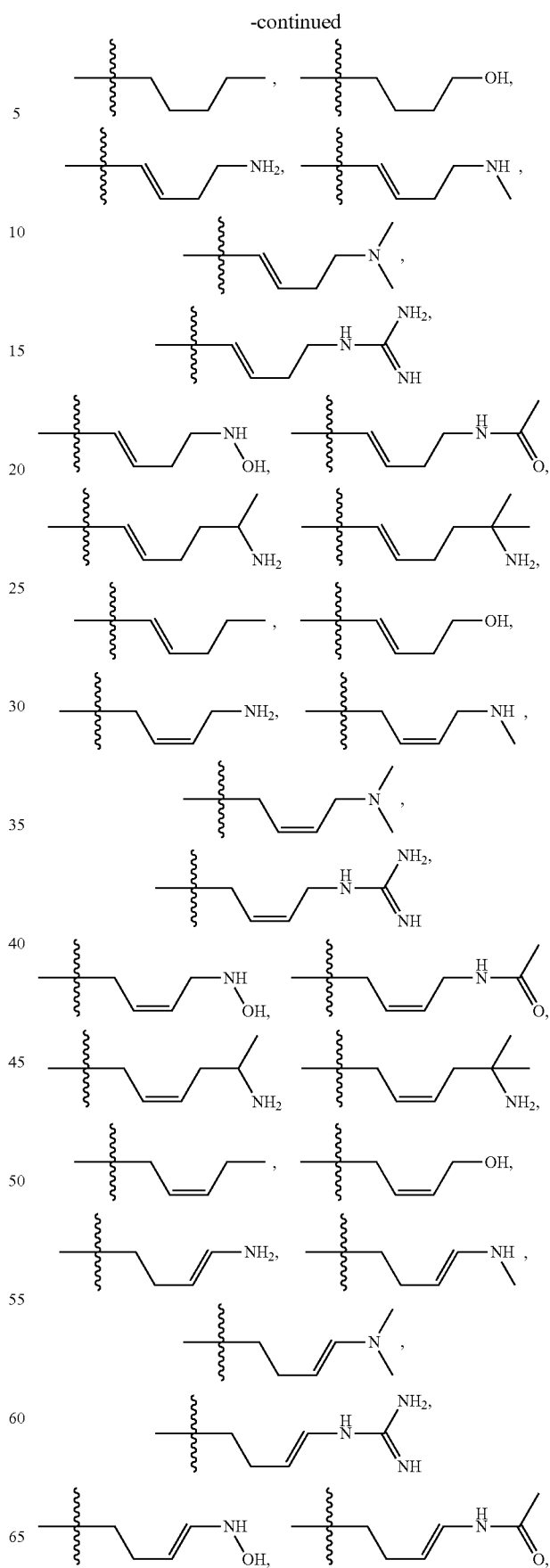

-continued
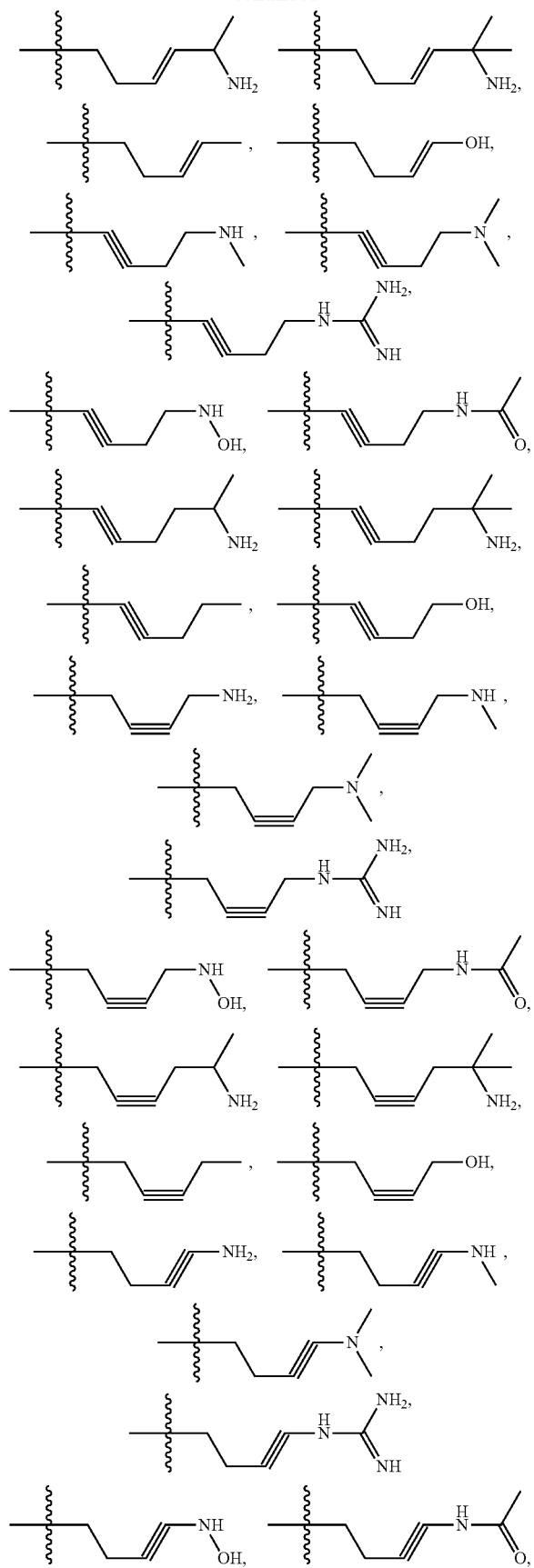
In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein L and $R_5$, taken together, are selected from the group consisting of:
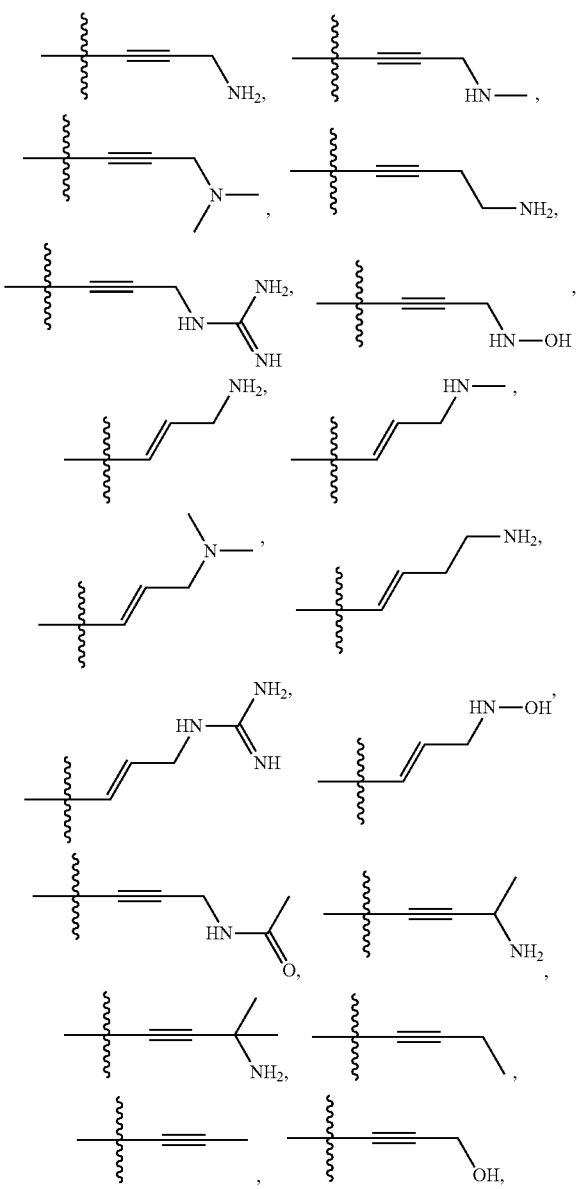

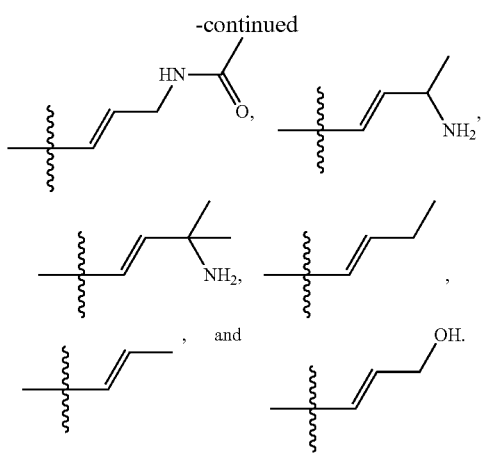

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein L and R$_5$, taken together, are selected from the group consisting of:

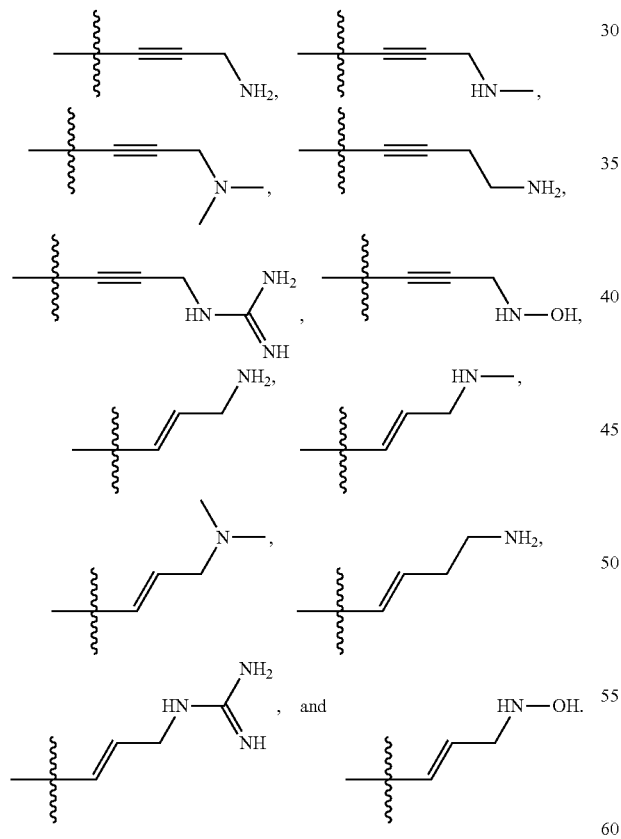

In one embodiment, the compound is a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, wherein L and R$_5$, taken together, are selected from the group consisting of:

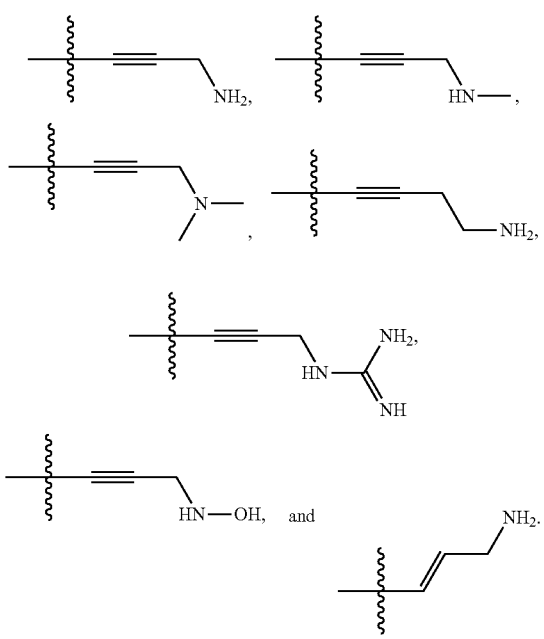

In embodiments, the present disclosure is directed to a compound of Formula (IV):

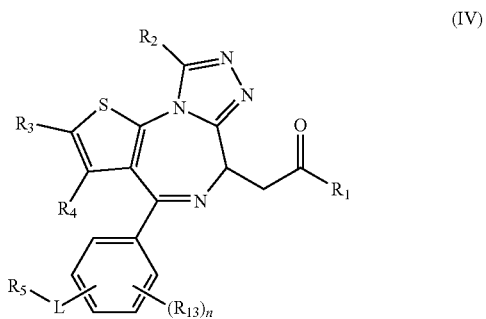

(IV)

or a pharmaceutically acceptable salt or enantiomer thereof, wherein

R$_1$ is —O—C$_1$-C$_6$-alkyl;

R$_2$ is methyl;

R$_3$ and R$_4$ are each methyl;

L is C$_2$-C$_4$ alkylene, C$_2$-C$_4$ alkenylene or C$_2$-C$_4$ alkynylene;

R$_5$ is selected from the group consisting of —N(R$_6$)(R$_7$); —C(H)(CH$_3$)—NH$_2$; —C(CH$_3$)$_2$—NH$_2$; methyl; and hydroxyl, wherein R$_6$ and R$_7$ are independently selected from the group consisting of H, methyl, —C(NH)—NH$_2$, hydroxy, and —C(O)CH$_3$;

each R$_{13}$ group is independently H or halo; and n is 0, 1, 2, 3 or 4.

In embodiments, the present disclosure is directed to a compound of Formula (IV):

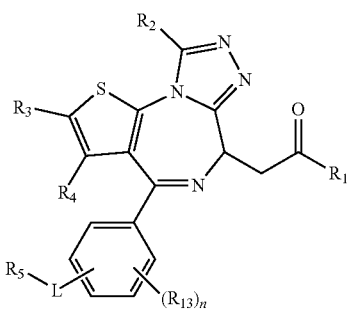

(IV)

or a pharmaceutically acceptable salt or enantiomer thereof, wherein
$R_1$ is —O—C(CH$_3$)$_3$;
$R_2$ is methyl;
$R_3$ and $R_4$ are each methyl;
L is $C_2$-$C_4$ alkylene, $C_2$-$C_4$ alkenylene or $C_2$-$C_4$ alkynylene;
$R_5$ is selected from the group consisting of —N(R$_6$)(R$_7$); —C(H)(CH$_3$)—NH$_2$; —C(CH$_3$)$_2$—NH$_2$; methyl; and hydroxyl, wherein $R_6$ and $R_7$ are independently selected from the group consisting of H, methyl, —C(NH)—NH$_2$, hydroxy, and —C(O)CH$_3$; and
n is 0.

In embodiments, the present disclosure is directed to a compound of Formula (IV) or a pharmaceutically acceptable salt or enantiomer thereof, wherein $R^5$ is selected from the group consisting of CH$_3$, OH, NH$_2$, NH(CH$_3$), N(CH$_3$)$_2$, NH(OH), NH—C(NH)(NH$_2$), NH—C(O)(CH$_3$), CH(CH$_3$)—NH$_2$ and C(CH$_3$)$_2$—NH$_2$. In an embodiment, $R^5$ is selected from the group consisting of NH$_2$, NH(CH$_3$), N(CH$_3$)$_2$, NH(OH) and NH—C(NH)(NH$_2$).

In embodiments, the present disclosure is directed to a compound of Formula (IV-1):

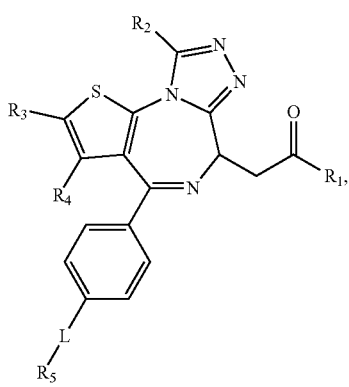

(IV-1)

or a pharmaceutically acceptable salt or enantiomer thereof, wherein
$R_1$ is —O—C$_1$-C$_6$-alkyl or —N(R$_8$)(R$_9$), wherein $R_5$ and $R_9$ are independently selected from the group consisting of H, C$_1$-C$_4$-alkyl, and phenyl, wherein the phenyl is optionally substituted with $R_{10}$, wherein $R_{10}$ is hydroxy;
$R_2$ is methyl;
$R_3$ and $R_4$ are each independently selected from the group consisting of H, methyl, and methoxy;
L is $C_2$-$C_4$ alkylene, $C_2$-$C_4$ alkenylene or $C_2$-$C_4$ alkynylene; and
$R_5$ is selected from the group consisting of —N(R$_6$)(R$_7$); —C(H)(CH$_3$)—NH$_2$; —C(CH$_3$)$_2$—NH$_2$; methyl; and hydroxyl, wherein $R_6$ and $R_7$ are independently selected from the group consisting of H, methyl, —C(NH)—NH$_2$, hydroxy, and —C(O)CH$_3$.

In embodiments, the present disclosure is directed to a compound of Formula (IV-1):

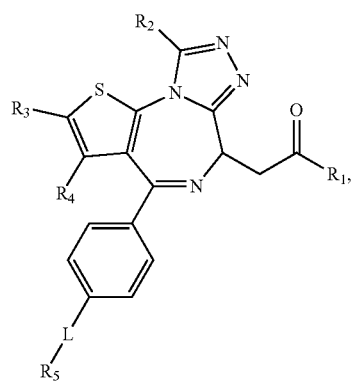

(IV-1)

or a pharmaceutically acceptable salt or enantiomer thereof, wherein
$R_1$ is —O—C$_1$-C$_6$-alkyl;
$R_2$ is methyl;
$R_3$ and $R_4$ are each methyl;
L is $C_2$-$C_4$ alkylene, $C_2$-$C_4$ alkenylene or $C_2$-$C_4$ alkynylene; and
$R_5$ is selected from the group consisting of —N(R$_6$)(R$_7$); —C(H)(CH$_3$)—NH$_2$; —C(CH$_3$)$_2$—NH$_2$; methyl; and hydroxyl, wherein $R_6$ and $R_7$ are independently selected from the group consisting of H, methyl, —C(NH)—NH$_2$, hydroxy, and —C(O)CH$_3$.

In embodiments, the present disclosure is directed to a compound of Formula (IV-1):

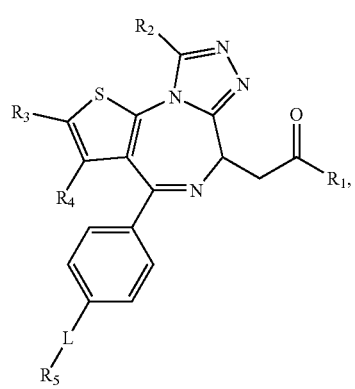

(IV-1)

or a pharmaceutically acceptable salt or enantiomer thereof, wherein
$R_1$ is —O—C(CH$_3$)$_3$;
$R_2$ is methyl;
$R_3$ and $R_4$ are each methyl;
L is $C_2$-$C_4$ alkylene, $C_2$-$C_4$ alkenylene or $C_2$-$C_4$ alkynylene; and $R_5$ is selected from the group consisting of —N($R_6$)($R_7$); —C(H)(CH$_3$)—NH$_2$; —C(CH$_3$)$_2$—NH$_2$; methyl; and hydroxyl, wherein $R_6$ and $R_7$ are independently selected from the group consisting of H, methyl, —C(NH)—NH$_2$, hydroxy, and —C(O)CH$_3$.

In embodiments, the present disclosure is directed to a compound of Formula (IV-1) or a pharmaceutically acceptable salt or enantiomer thereof, wherein $R^5$ is selected from the group consisting of CH$_3$, OH, NH$_2$, NH(CH$_3$), N(CH$_3$)$_2$, NH(OH), NH—C(NH)(NH$_2$), NH—C(O)(CH$_3$), CH(CH$_3$)—NH$_2$ and C(CH$_3$)$_2$—NH$_2$. In an embodiment, $R^5$ is selected from the group consisting of NH$_2$, NH(CH$_3$), N(CH$_3$)$_2$, NH(OH), CH(CH$_3$)—NH$_2$ and NH—C(NH)(NH$_2$).

In embodiments, the present disclosure is directed to a compound of Formula (X):

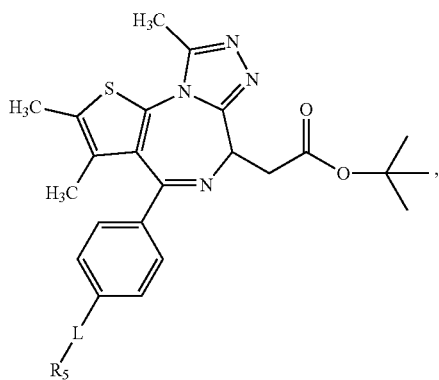

(X)

or a pharmaceutically acceptable salt or enantiomer thereof, wherein
L is C$_2$-C$_4$ alkylene, C$_2$-C$_4$ alkenylene or C$_2$-C$_4$ alkynylene; and
$R_5$ is selected from the group consisting of —N($R_6$)($R_7$); —C(H)(CH$_3$)—NH$_2$; —C(CH$_3$)$_2$—NH$_2$; methyl; and hydroxyl, wherein $R_6$ and $R_7$ are independently selected from the group consisting of H, methyl, —C(NH)—NH$_2$, hydroxy, and —C(O)CH$_3$.

In embodiments, the present disclosure is directed to a compound of Formula (X):

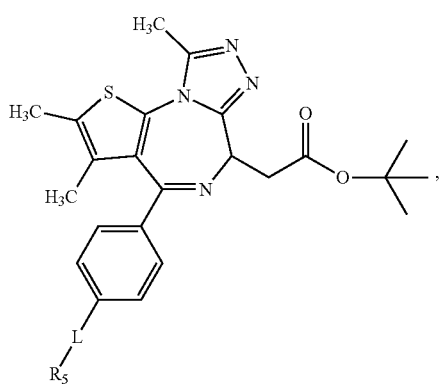

(X)

or a pharmaceutically acceptable salt or enantiomer thereof, wherein L and $R_5$ are selected from the group consisting of:

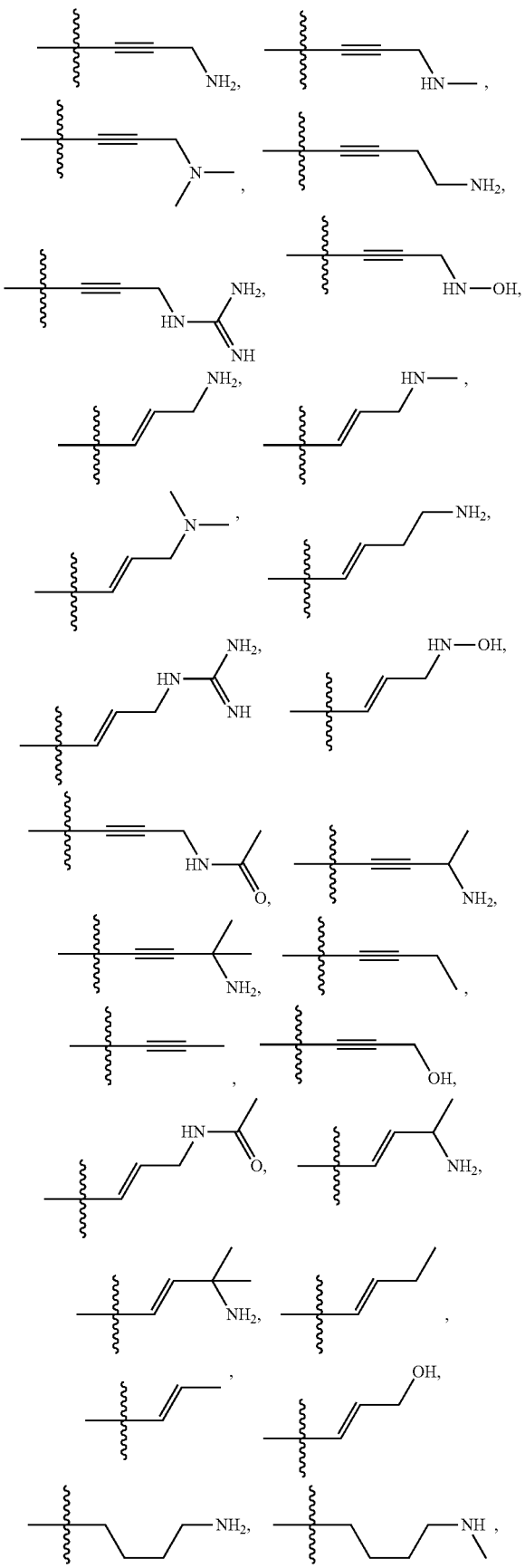

-continued
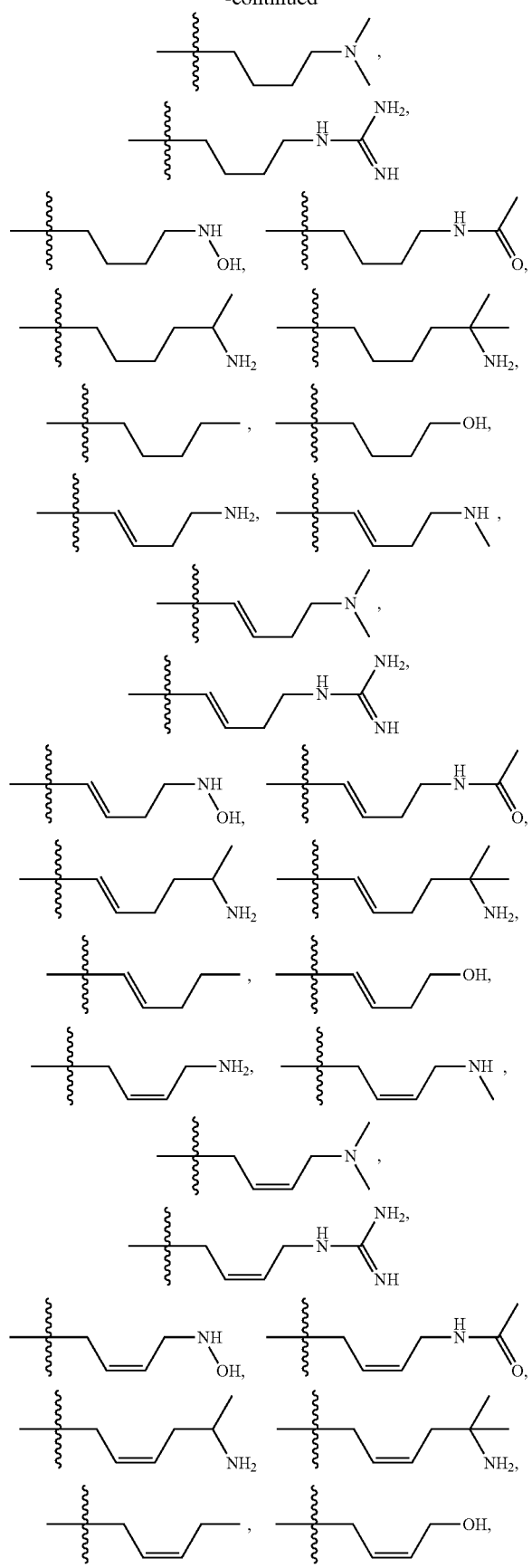
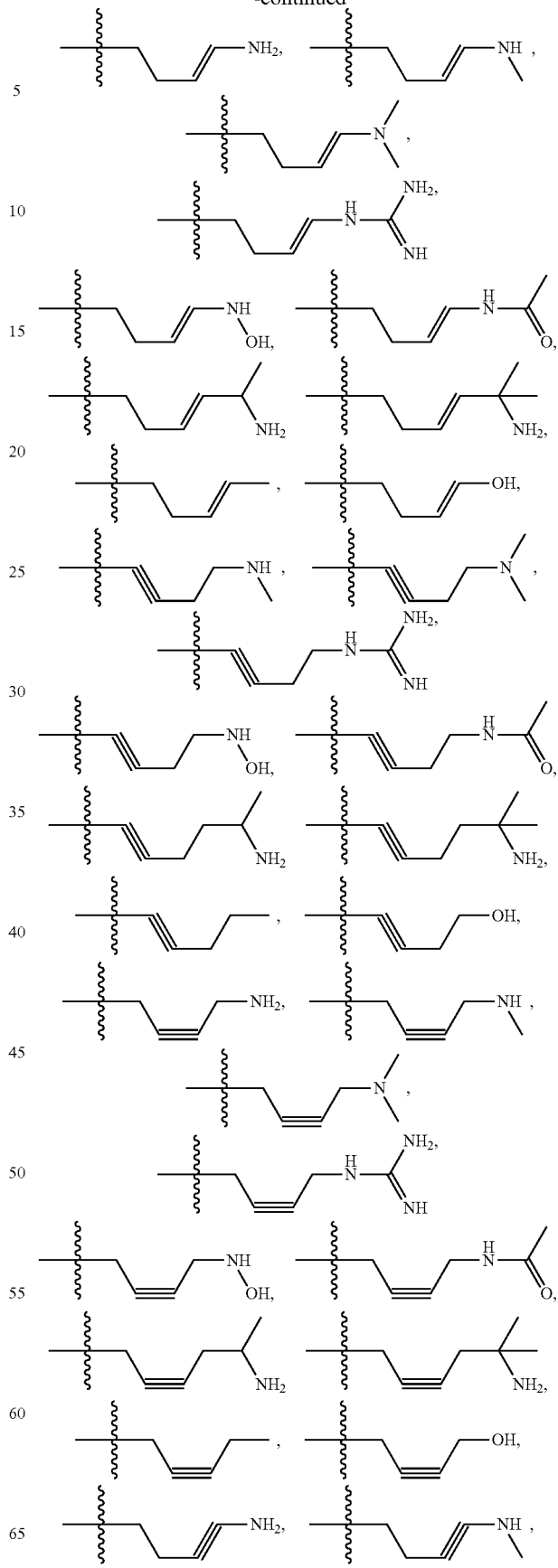

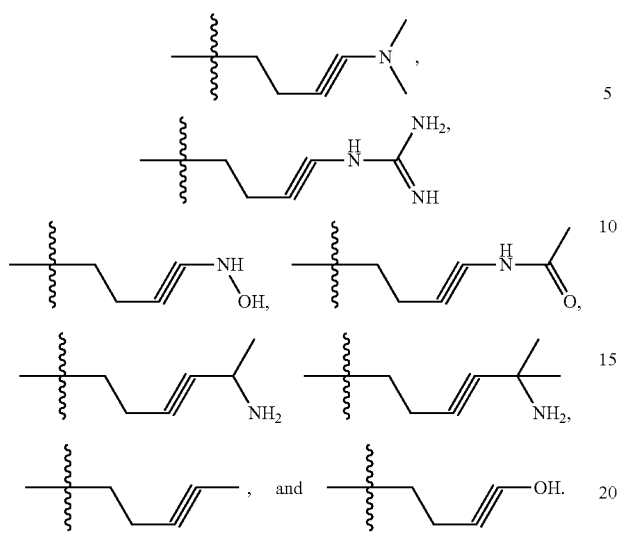
In embodiments, L-R₅ is selected from the group consisting of:
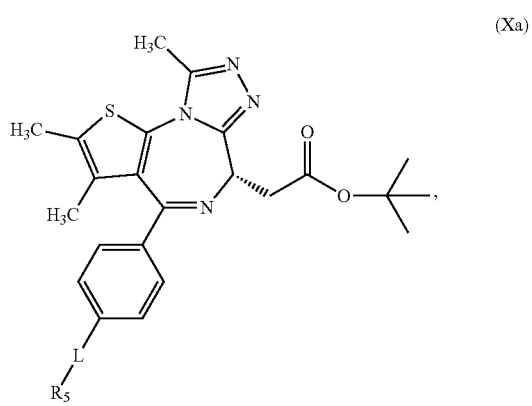
or a pharmaceutically acceptable salt or enantiomer thereof, wherein L and R₅ are selected from the group consisting of:
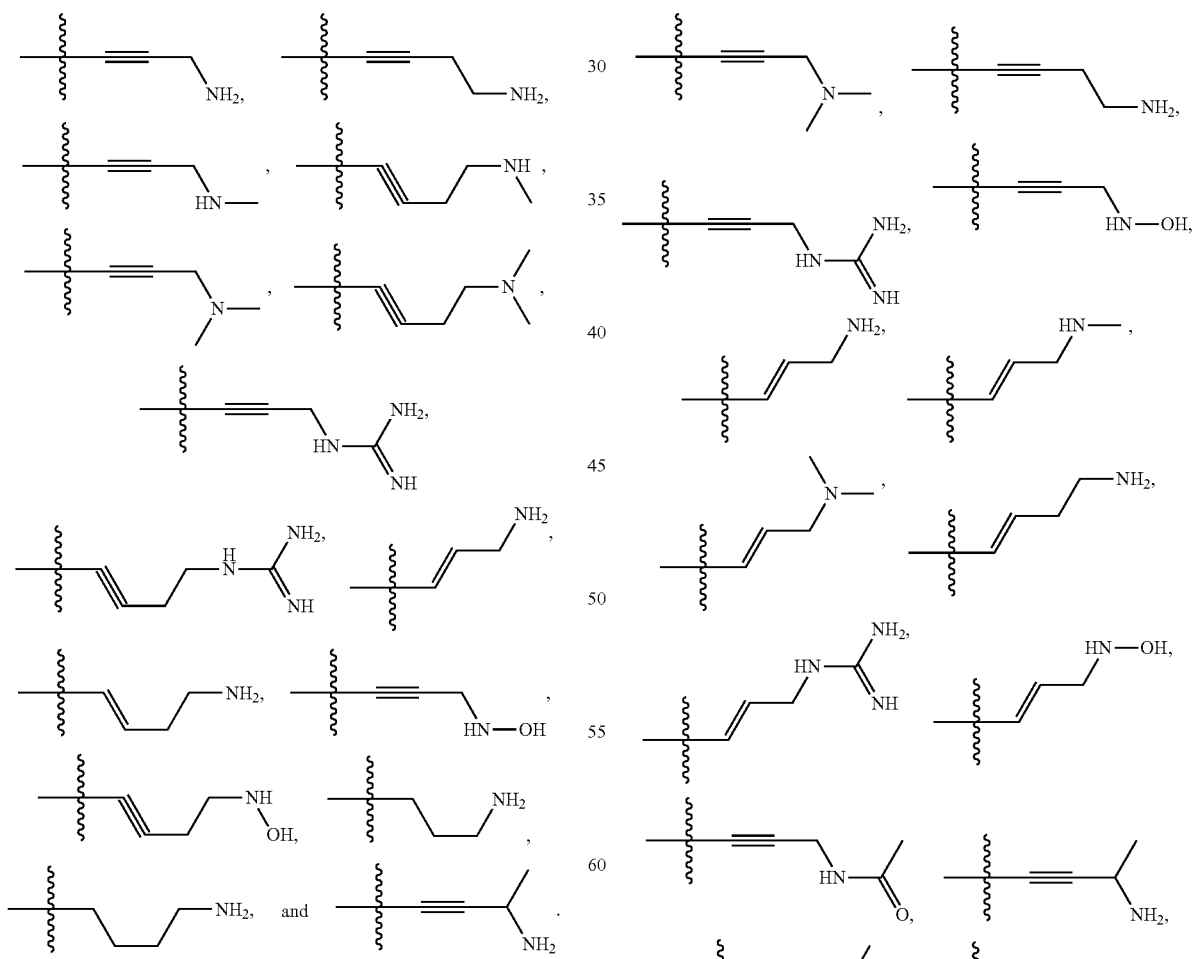
In embodiments, the present disclosure is directed to a compound of Formula (Xa):

-continued
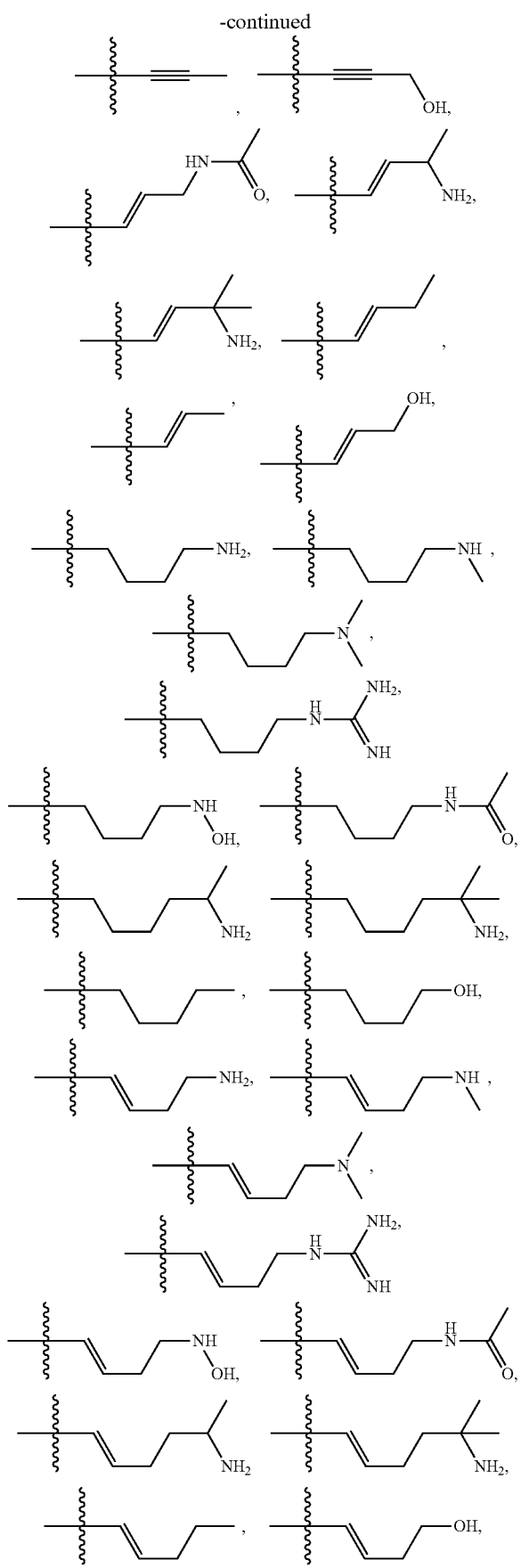
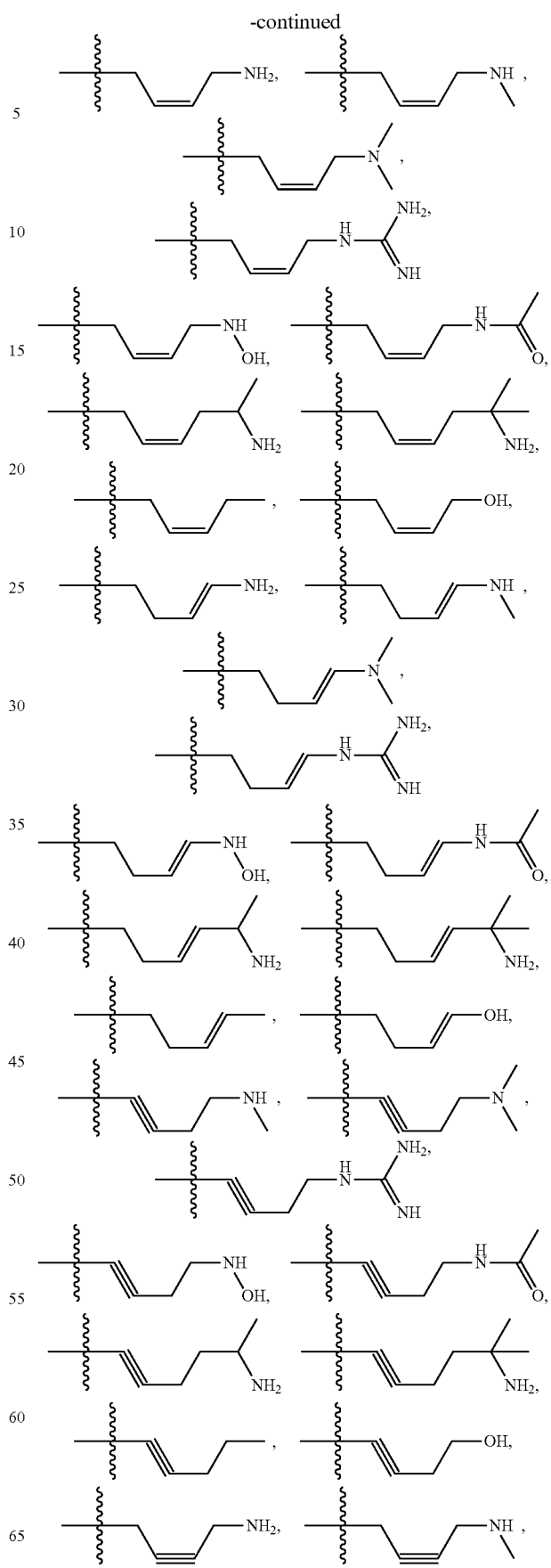

-continued
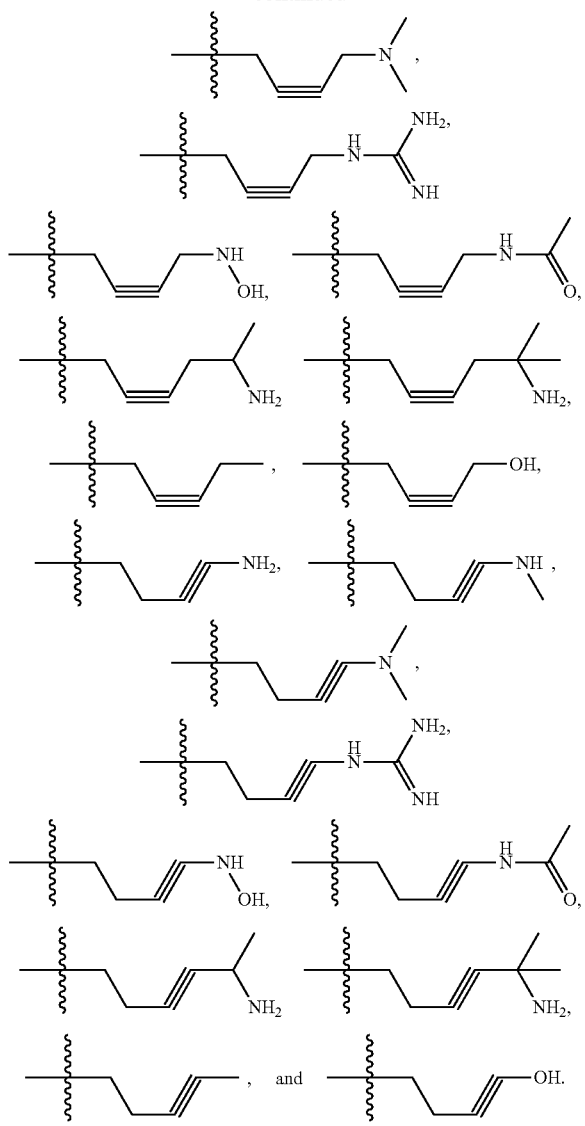
In embodiments, L-R$_5$ is selected from the group consisting of:
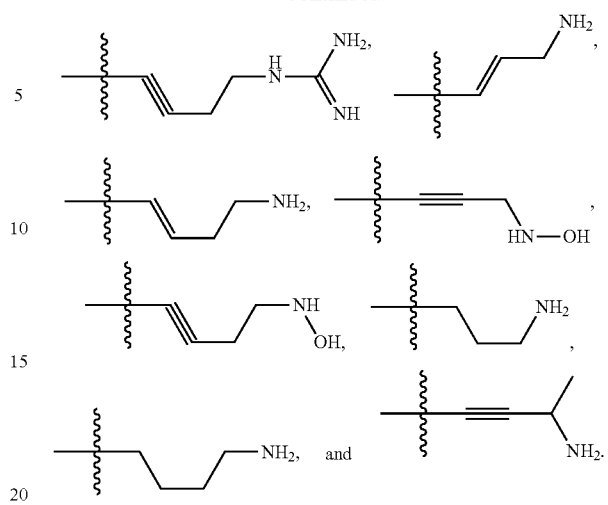
In embodiments, the present disclosure is directed to a compound of Formula (Xb):
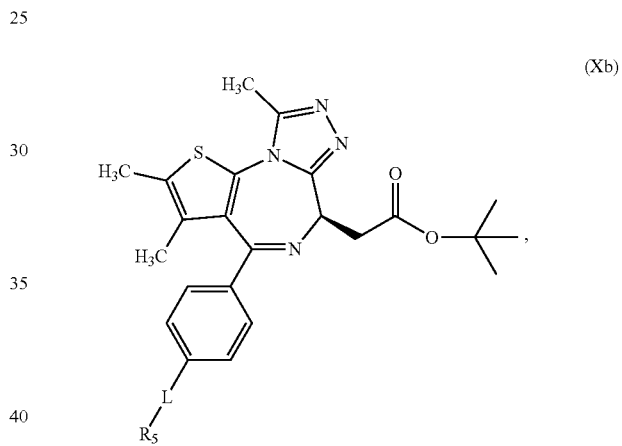
or a pharmaceutically acceptable salt or enantiomer thereof, wherein L and R$_5$ are selected from the group consisting of:
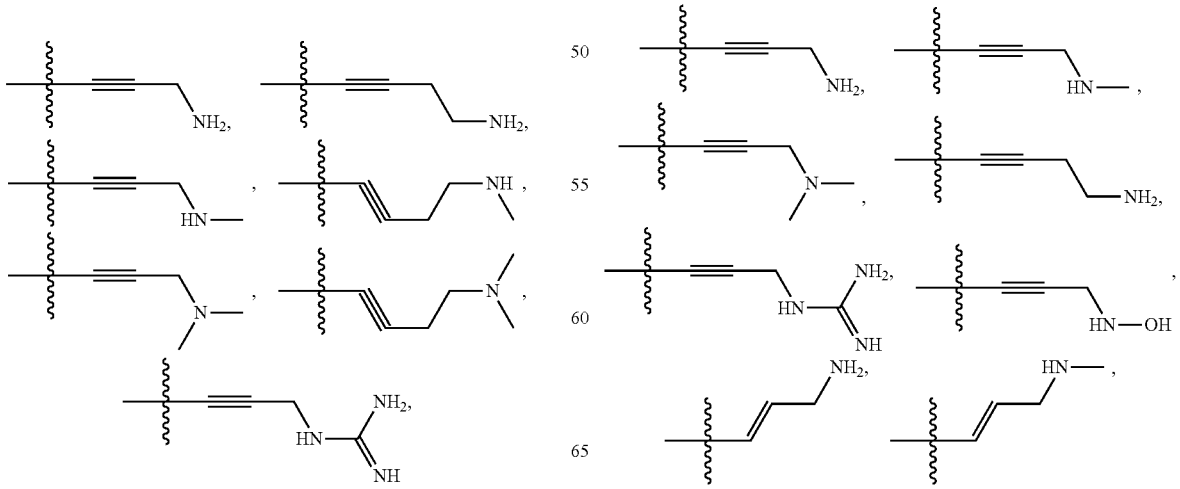

-continued
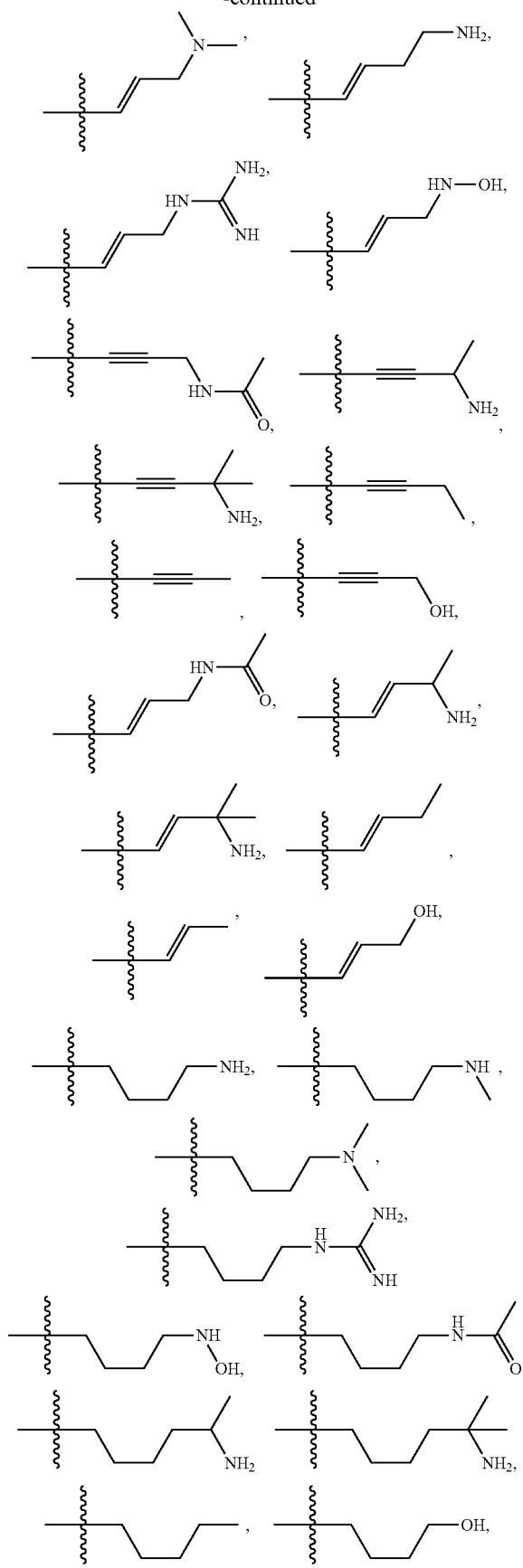
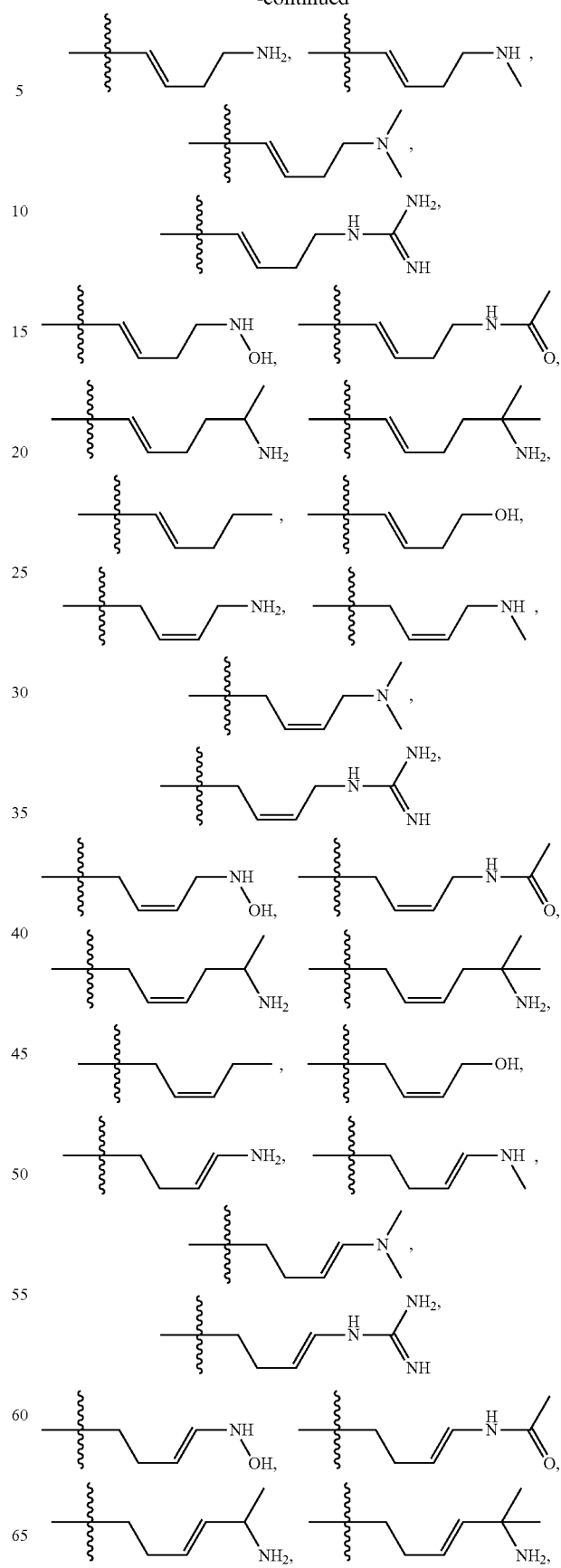

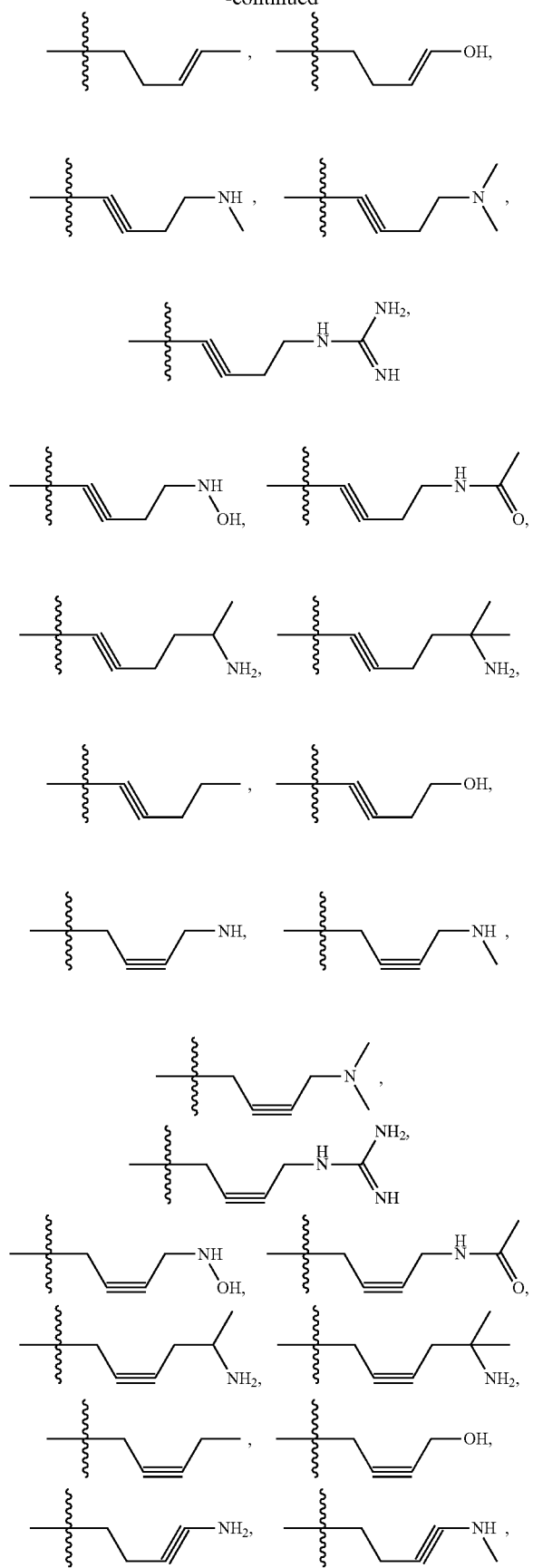
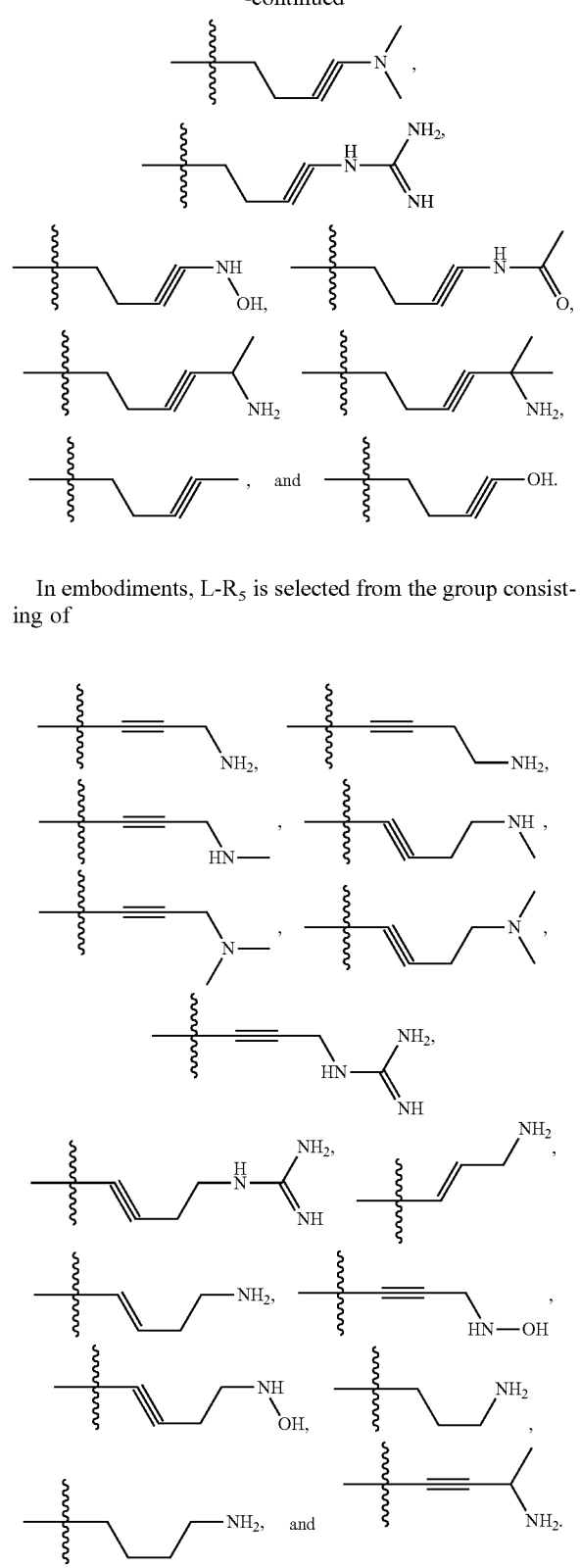
In embodiments, L-R$_5$ is selected from the group consisting of
In one embodiment, the present disclosure is directed to a compound of Formula (I), or a salt (e.g., a pharmaceutically acceptable salt) thereof, and has a structure selected from the group consisting of those structures in Table 1.

TABLE 1

| Compound No. | Structure | Name[1] |
|---|---|---|
| 1 | 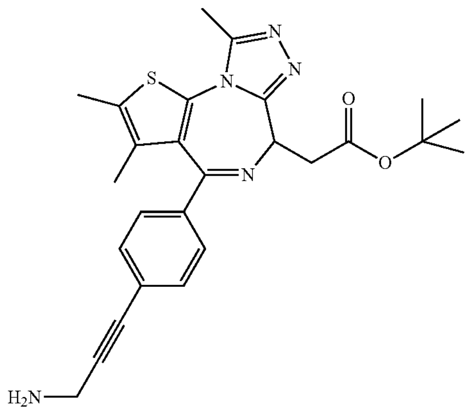 [SMILES: Cc1sc2c(c1C)C(c1ccc(C#CCN)cc1)=NC(CC(=O)OC(C)(C)C)c1nnc(C)n1-2] | tert-butyl 2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate |
| 1a | 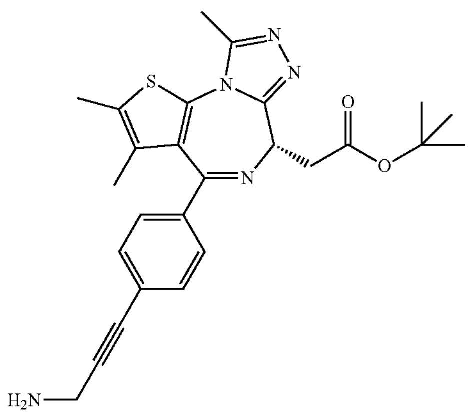 [SMILES: Cc1sc2c(c1C)C(c1ccc(C#CCN)cc1)=N[C@@H](CC(=O)OC(C)(C)C)c1nnc(C)n1-2] | tert-butyl (S)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate |
| 1b | 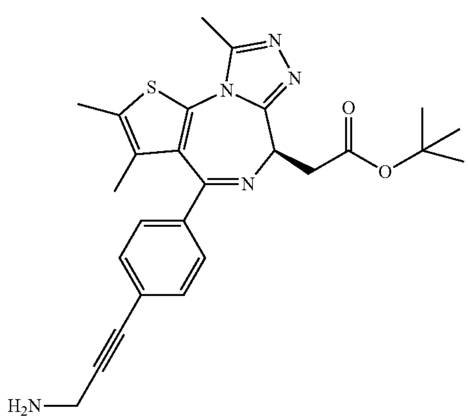 [SMILES: Cc1sc2c(c1C)C(c1ccc(C#CCN)cc1)=N[C@H](CC(=O)OC(C)(C)C)c1nnc(C)n1-2] | tert-butyl (R)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 2 | 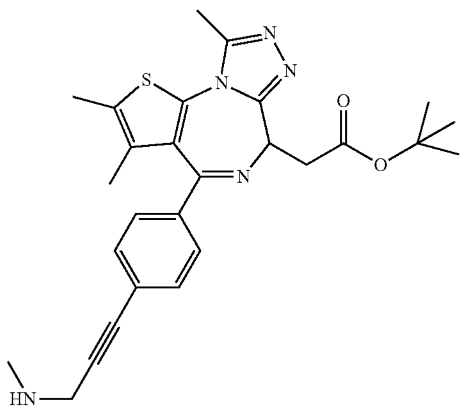 [SMILES: CNCC#Cc1ccc(C2=NC(CC(=O)OC(C)(C)C)c3nnc(C)n3-c3sc(C)c(C)c32)cc1] | tert-butyl 2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate |
| 2a | 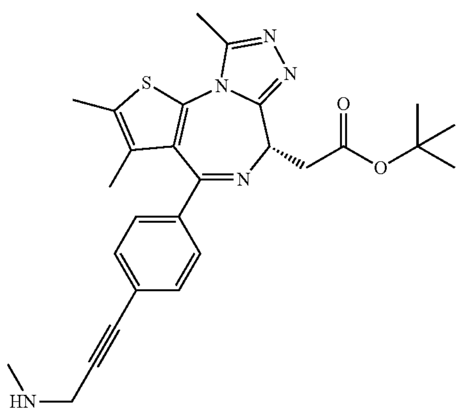 [SMILES: CNCC#Cc1ccc(C2=N[C@@H](CC(=O)OC(C)(C)C)c3nnc(C)n3-c3sc(C)c(C)c32)cc1] | tert-butyl (S)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate |
| 2b | 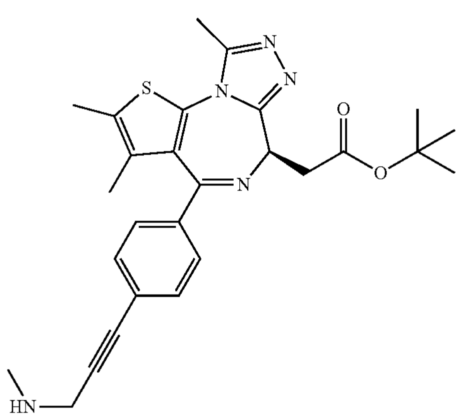 [SMILES: CNCC#Cc1ccc(C2=N[C@H](CC(=O)OC(C)(C)C)c3nnc(C)n3-c3sc(C)c(C)c32)cc1] | tert-butyl (R)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate |

TABLE 1-continued
| Compound No. | Structure | Name[1] |
|---|---|---|
| 3 | 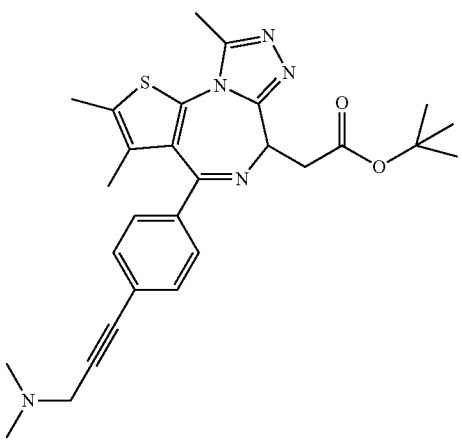 [SMILES: Cc1sc2c(c1C)C(c1ccc(C#CCN(C)C)cc1)=NC(CC(=O)OC(C)(C)C)c1nnc(C)n1-2] | tert-butyl 2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate |
| 3a | 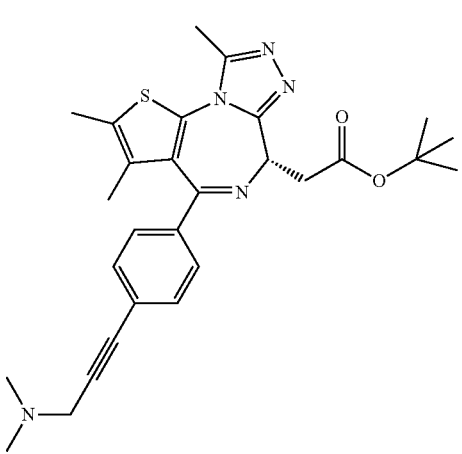 [SMILES: Cc1sc2c(c1C)C(c1ccc(C#CCN(C)C)cc1)=N[C@@H](CC(=O)OC(C)(C)C)c1nnc(C)n1-2] | tert-butyl (S)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate |
| 3b | 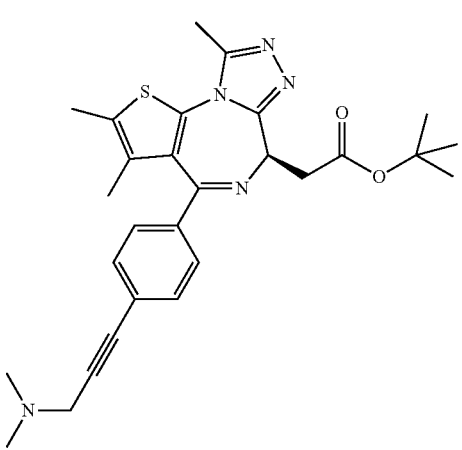 [SMILES: Cc1sc2c(c1C)C(c1ccc(C#CCN(C)C)cc1)=N[C@H](CC(=O)OC(C)(C)C)c1nnc(C)n1-2] | tert-butyl (R)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name |
|---|---|---|
| 4 | 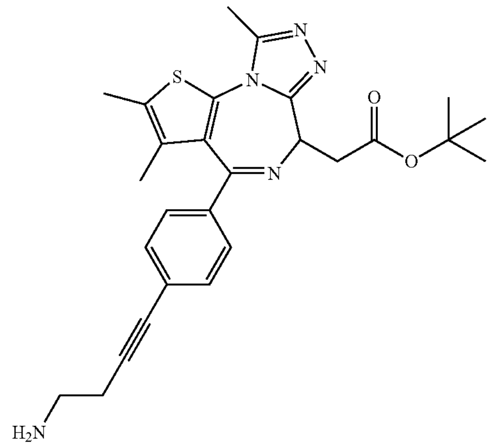 | tert-butyl 2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate |
| 4a | 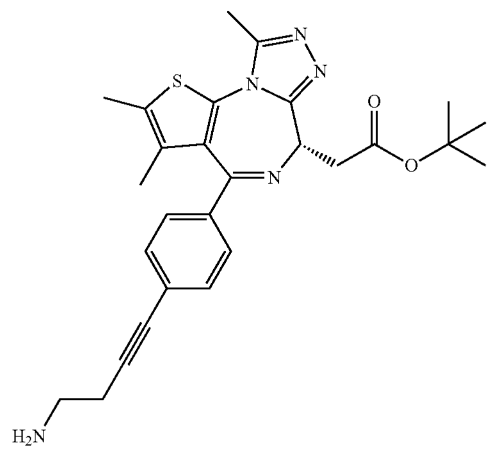 [SMILES: Cc1sc2c(c1C)C(c1ccc(C#CCCN)cc1)=NC(CC(=O)OC(C)(C)C)c1nnc(C)n1-2] | tert-butyl (S)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate |
| 4b | 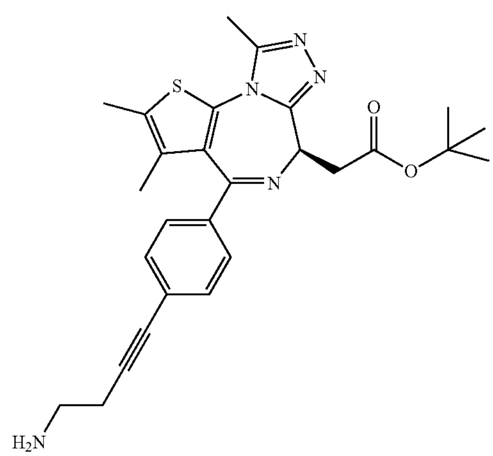 [SMILES: Cc1sc2c(c1C)C(c1ccc(C#CCCN)cc1)=N[C@H](CC(=O)OC(C)(C)C)c1nnc(C)n1-2] | tert-butyl (R)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate |

TABLE 1-continued
| Compound No. | Structure | Name[1] |
|---|---|---|
| 5 | 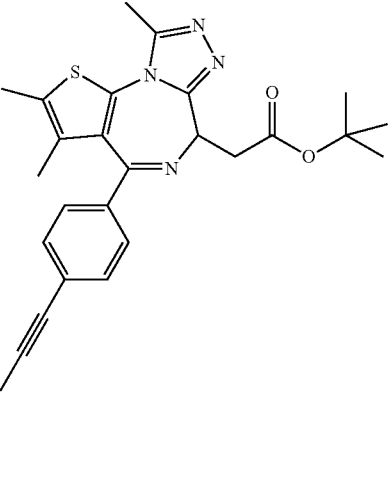 | tert-butyl 2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate |
| 5a | 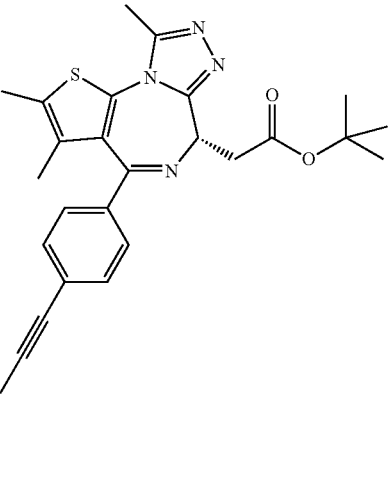 | tert-butyl (S)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate |
| 5b | 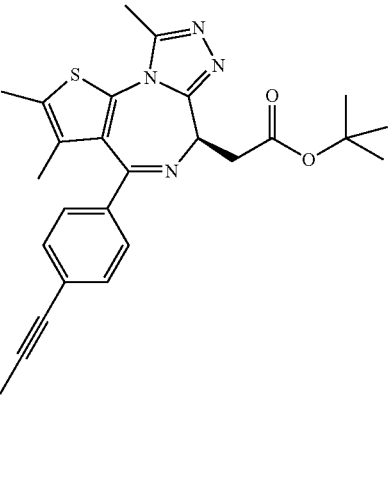 | tert-butyl (R)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 6 | 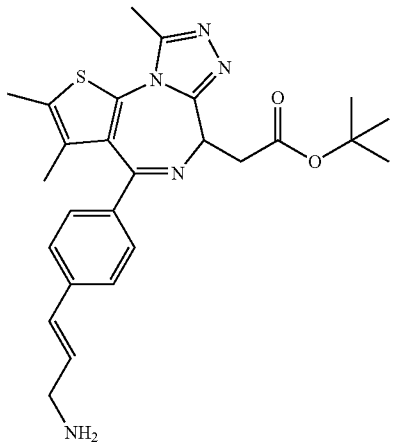 | tert-butyl (E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate |
| 6a | 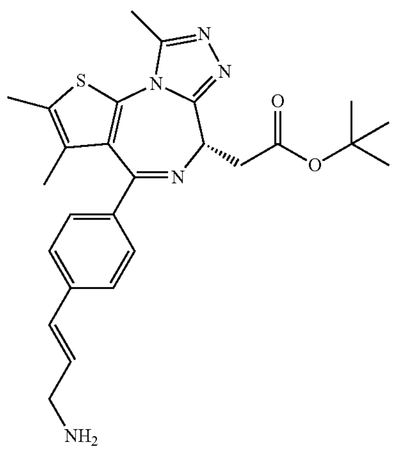 [SMILES: Cc1sc2c(c1C)C(c1ccc(/C=C/CN)cc1)=NC(CC(=O)OC(C)(C)C)c1nnc(C)n1-2] | tert-butyl (S,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate |
| 6b | 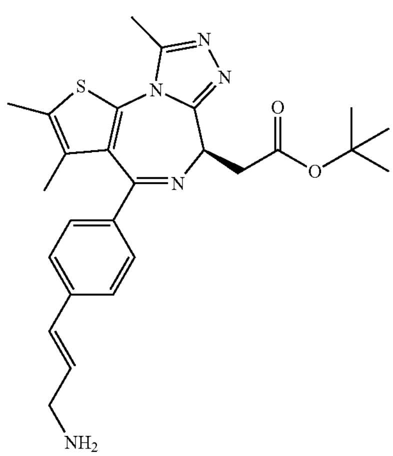 [SMILES: Cc1sc2c(c1C)C(c1ccc(/C=C/CN)cc1)=N[C@H](CC(=O)OC(C)(C)C)c1nnc(C)n1-2] | tert-butyl (R,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 7 | 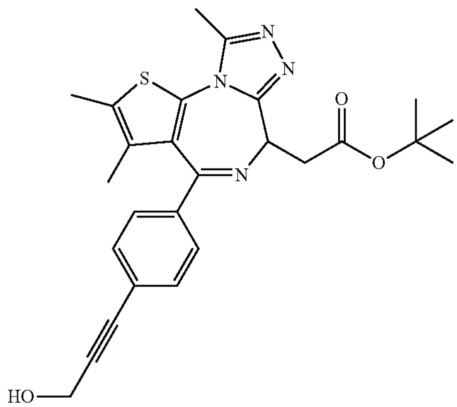 [SMILES: Cc1sc2c(c1C)C(c1ccc(C#CCO)cc1)=NC(CC(=O)OC(C)(C)C)c1nnc(C)n1-2] | tert-butyl 2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate |
| 7a | 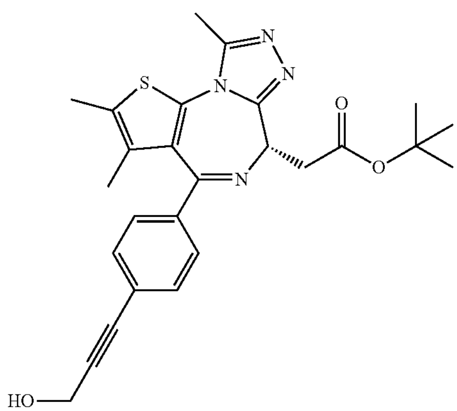 | tert-butyl (S)-2-(4-(4-(3-hydroxyprop-1-yn-1-yl)phenyl)-2,3,9-trimethyl-6H-thieno[3,2-f][1,2,4]triazolo[4,3-a][1,4] diazepin-6-yl)acetate |
| 7b | 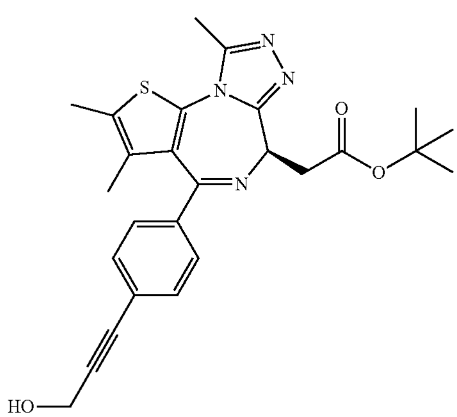 [SMILES: Cc1sc2c(c1C)C(c1ccc(C#CCO)cc1)=N[C@H](CC(=O)OC(C)(C)C)c1nnc(C)n1-2] | tert-butyl (R)-2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate |

| Compound No. | Structure | Name |
|---|---|---|
| 8 | 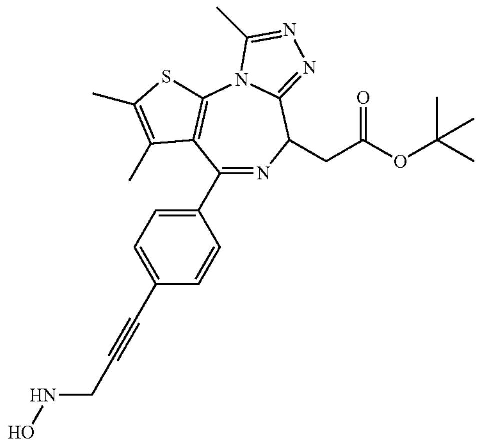 [SMILES: Cc1sc2c(c1C)C(c1ccc(C#CCNO)cc1)=NC(CC(=O)OC(C)(C)C)c1nnc(C)n1-2] | tert-butyl 2-(4-(4-(3-(hydroxyamino)prop-1-yn-1-yl)phenyl)-2,3,9-trimethyl-6H-thieno[3,2-f][1,2,4]triazolo[4,3-a][1,4]diazepin-6-yl)acetate |
| 8a | 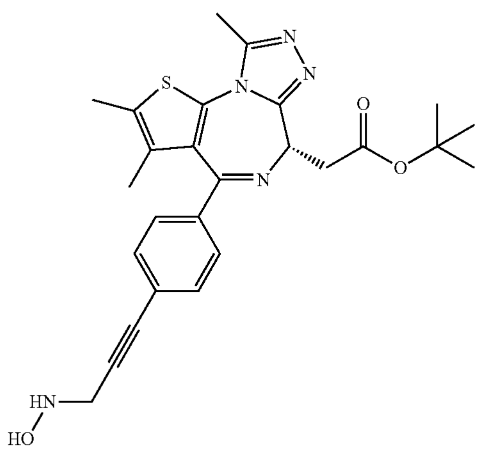 [SMILES: Cc1sc2c(c1C)C(c1ccc(C#CCNO)cc1)=N[C@@H](CC(=O)OC(C)(C)C)c1nnc(C)n1-2] | tert-butyl (S)-2-(4-(4-(3-(hydroxyamino)prop-1-yn-1-yl)phenyl)-2,3,9-trimethyl-6H-thieno[3,2-f][1,2,4]triazolo[4,3-a][1,4]diazepin-6-yl)acetate |
| 8b | 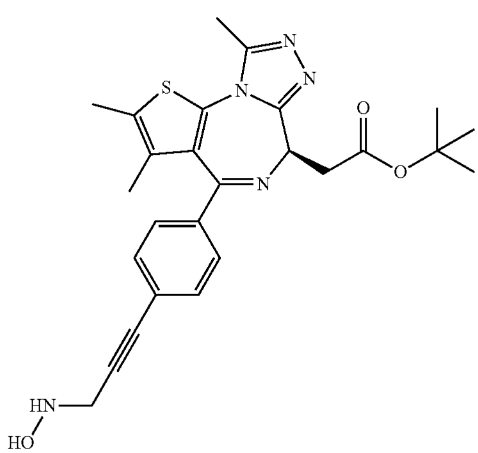 [SMILES: Cc1sc2c(c1C)C(c1ccc(C#CCNO)cc1)=N[C@H](CC(=O)OC(C)(C)C)c1nnc(C)n1-2] | tert-butyl (R)-2-(4-(4-(3-(hydroxyamino)prop-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 9 | 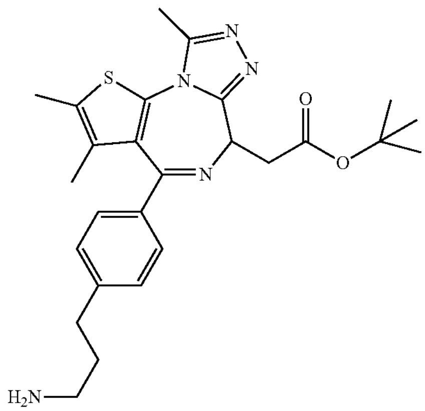 [SMILES: Cc1sc2c(c1C)C(c1ccc(CCCN)cc1)=NC(CC(=O)OC(C)(C)C)c1nnc(C)n1-2] | tert-butyl 2-(4-(4-(3-aminopropyl)phenyl)-2,3,9-trimethyl-6H-thieno[3,2-f][1,2,4]triazolo[4,3-a][1,4]diazepin-6-yl)acetate |
| 9a | 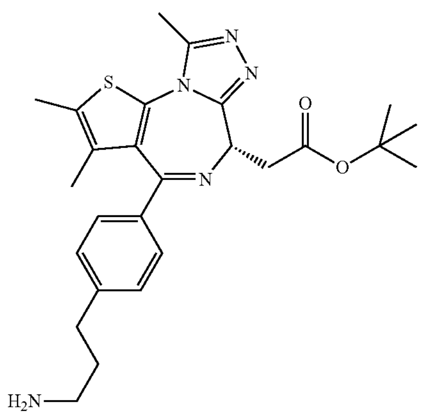 [SMILES: Cc1sc2c(c1C)C(c1ccc(CCCN)cc1)=N[C@@H](CC(=O)OC(C)(C)C)c1nnc(C)n1-2] | tert-butyl (S)-2-(4-(4-(3-aminopropyl)phenyl)-2,3,9-trimethyl-6H-thieno[3,2-f][1,2,4]triazolo[4,3-a][1,4]diazepin-6-yl)acetate |
| 9b | 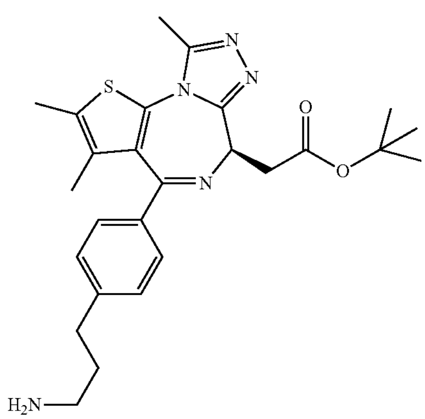 [SMILES: Cc1sc2c(c1C)C(c1ccc(CCCN)cc1)=N[C@H](CC(=O)OC(C)(C)C)c1nnc(C)n1-2] | tert-butyl (R)-2-(4-(4-(3-aminopropyl)phenyl)-2,3,9-trimethyl-6H-thieno[3,2-f][1,2,4]triazolo[4,3-a][1,4]diazepin-6-yl)acetate |

TABLE 1-continued
| Compound No. | Structure | Name[1] |
|---|---|---|
| 10 | 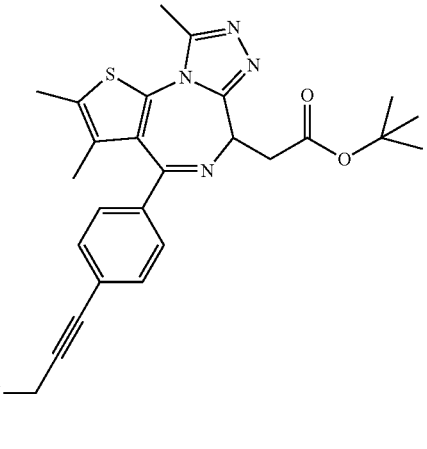 | tert-butyl 2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate |
| 10a | 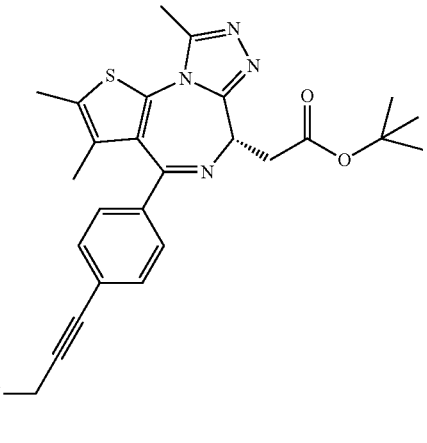 | tert-butyl (S)-2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate |
| 10b | 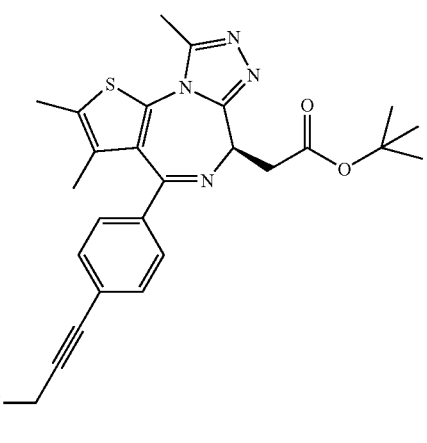 | tert-butyl (R)-2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 11 | 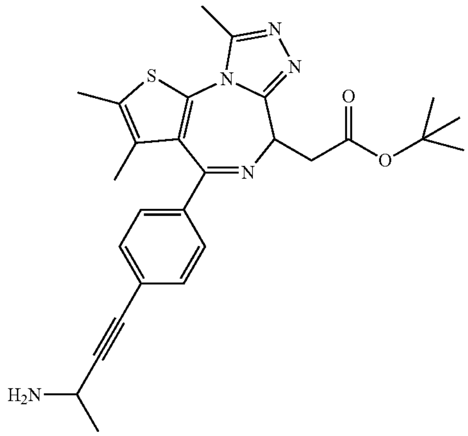 [SMILES: Cc1sc2c(c1C)C(c1ccc(C#CC(C)N)cc1)=NC(CC(=O)OC(C)(C)C)c1nnc(C)n1-2] | tert-butyl 2-(4-(4-(3-aminobut-1-yn-1-yl)phenyl)-2,3,9-trimethyl-6H-thieno[3,2-f][1,2,4]triazolo[4,3-a][1,4]diazepin-6-yl)acetate |
| 11a | 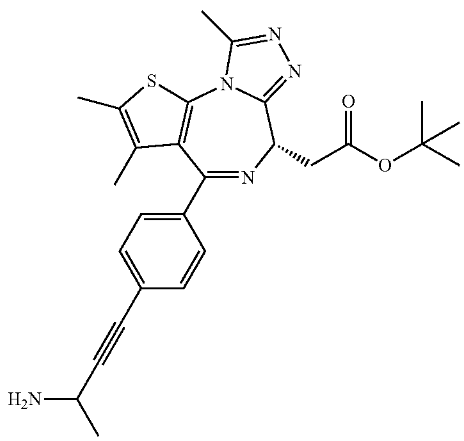 [SMILES: Cc1sc2c(c1C)C(c1ccc(C#CC(C)N)cc1)=N[C@@H](CC(=O)OC(C)(C)C)c1nnc(C)n1-2] | tert-butyl 2-((6S)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate |
| 11b | 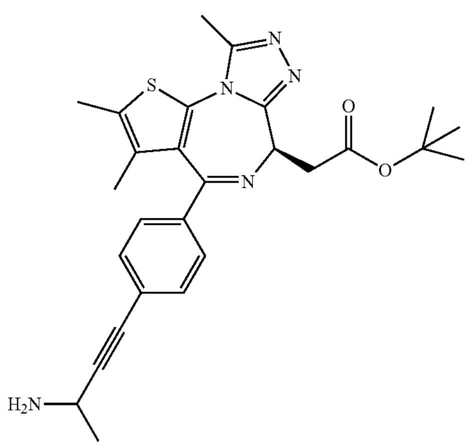 [SMILES: Cc1sc2c(c1C)C(c1ccc(C#CC(C)N)cc1)=N[C@H](CC(=O)OC(C)(C)C)c1nnc(C)n1-2] | tert-butyl 2-((6R)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 12 | 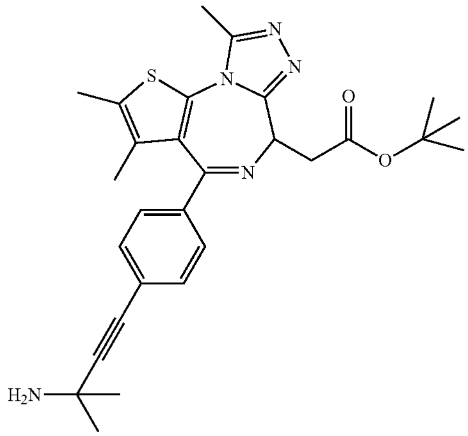 [SMILES: Cc1sc2c(c1C)C(c1ccc(C#CC(C)(C)N)cc1)=NC(CC(=O)OC(C)(C)C)c1nnc(C)n1-2] | tert-butyl 2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate |
| 12a | 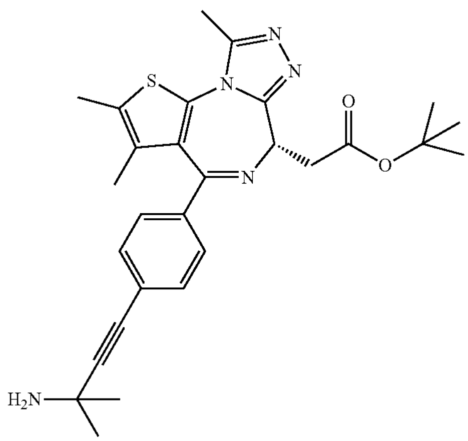 [SMILES: Cc1sc2c(c1C)C(c1ccc(C#CC(C)(C)N)cc1)=N[C@@H](CC(=O)OC(C)(C)C)c1nnc(C)n1-2] | tert-butyl (S)-2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate |
| 12b | 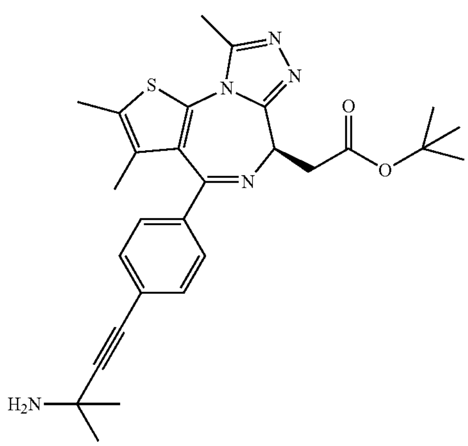 [SMILES: Cc1sc2c(c1C)C(c1ccc(C#CC(C)(C)N)cc1)=N[C@H](CC(=O)OC(C)(C)C)c1nnc(C)n1-2] | tert-butyl (R)-2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 13 | 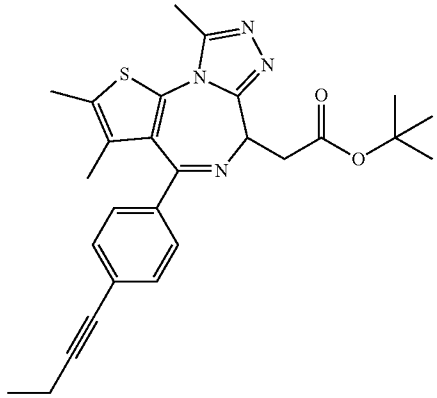 [SMILES: CCC#Cc1ccc(C2=NC(CC(=O)OC(C)(C)C)c3nnc(C)n3-c3sc(C)c(C)c32)cc1] | tert-butyl 2-(4-(4-(but-1-yn-1-yl)phenyl)-2,3,9-trimethyl-6H-thieno[3,2-f][1,2,4]triazolo[4,3-a][1,4]diazepin-6-yl)acetate |
| 13a | 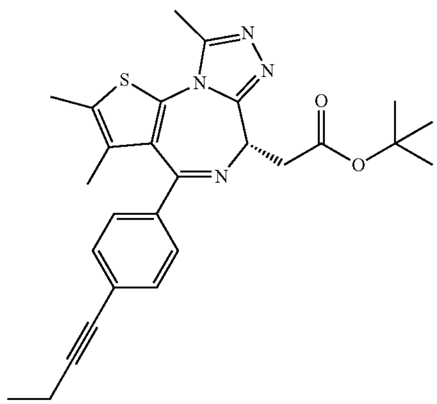 [SMILES: CCC#Cc1ccc(C2=N[C@@H](CC(=O)OC(C)(C)C)c3nnc(C)n3-c3sc(C)c(C)c32)cc1] | tert-butyl (S)-2-(4-(4-(but-1-yn-1-yl)phenyl)-2,3,9-trimethyl-6H-thieno[3,2-f][1,2,4]triazolo[4,3-a][1,4]diazepin-6-yl)acetate |
| 13b | 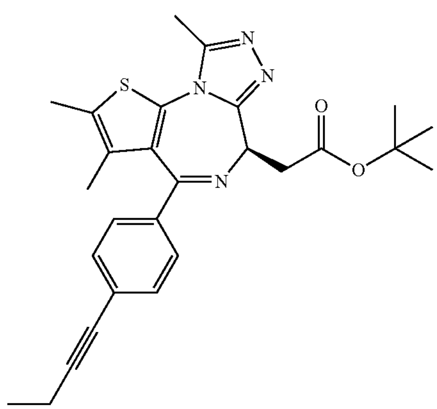 [SMILES: CCC#Cc1ccc(C2=N[C@H](CC(=O)OC(C)(C)C)c3nnc(C)n3-c3sc(C)c(C)c32)cc1] | tert-butyl (R)-2-(4-(4-(but-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 14 | 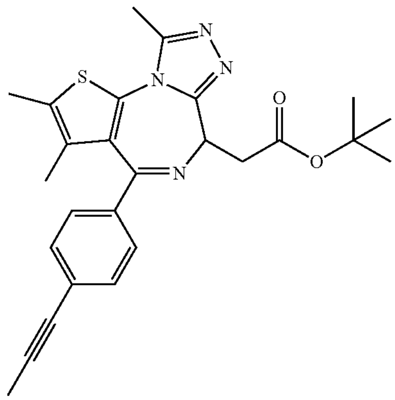 [SMILES: CC#Cc1ccc(C2=NC(CC(=O)OC(C)(C)C)c3nnc(C)n3-c3sc(C)c(C)c32)cc1] | tert-butyl 2-(2,3,9-trimethyl-4-(4-(prop-1-yn-1-yl)phenyl)-6H-thieno[3,2-f][1,2,4]triazolo[4,3-a][1,4]diazepin-6-yl)acetate |
| 14a | 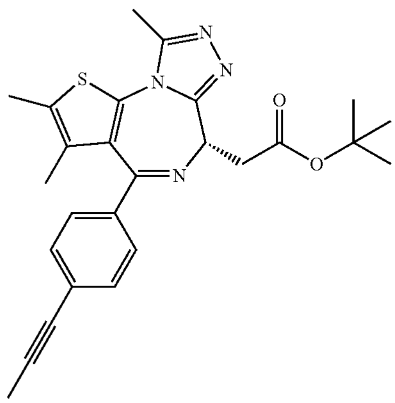 [SMILES: CC#Cc1ccc(C2=N[C@@H](CC(=O)OC(C)(C)C)c3nnc(C)n3-c3sc(C)c(C)c32)cc1] | tert-butyl (S)-2-(2,3,9-trimethyl-4-(4-(prop-1-yn-1-yl)phenyl)-6H-thieno[3,2-f][1,2,4]triazolo[4,3-a][1,4]diazepin-6-yl)acetate |
| 14b | 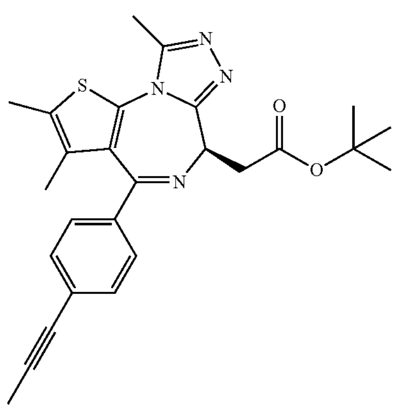 [SMILES: CC#Cc1ccc(C2=N[C@H](CC(=O)OC(C)(C)C)c3nnc(C)n3-c3sc(C)c(C)c32)cc1] | tert-butyl (R)-2-(2,3,9-trimethyl-4-(4-(prop-1-yn-1-yl)phenyl)-6H-thieno[3,2-f][1,2,4]triazolo[4,3-a][1,4]diazepin-6-yl)acetate |
| 16 | 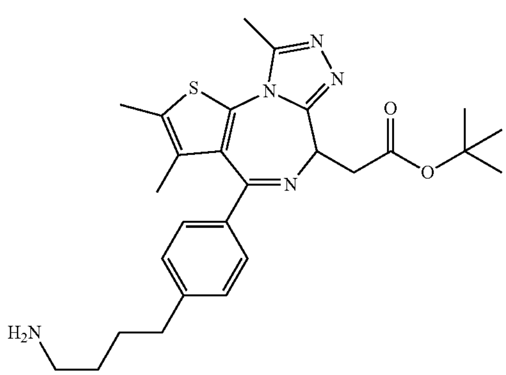 [SMILES: Cc1sc2c(c1C)C(c1ccc(CCCCN)cc1)=NC(CC(=O)OC(C)(C)C)c1nnc(C)n1-2] | tert-butyl 2-(4-(4-(4-aminobutyl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 16a | 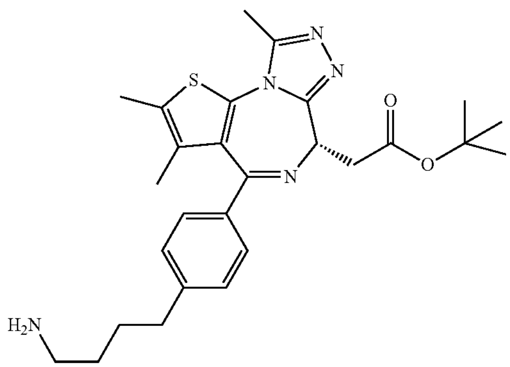 [SMILES: Cc1sc2c(c1C)C(c1ccc(CCCCN)cc1)=N[C@@H](CC(=O)OC(C)(C)C)c1nnc(C)n1-2] | tert-butyl (S)-2-(4-(4-(4-aminobutyl)phenyl)-2,3,9-trimethyl-6H-thieno[3,2-f][1,2,4]triazolo[4,3-a][1,4]diazepin-6-yl)acetate |
| 16b | 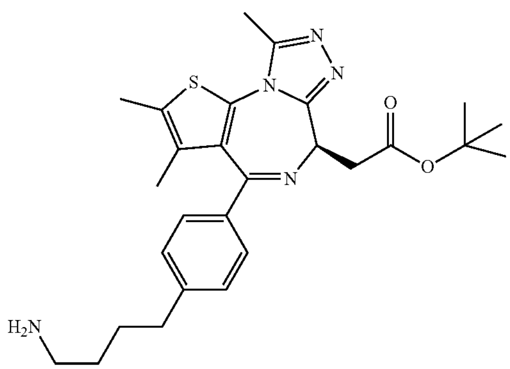 [SMILES: Cc1sc2c(c1C)C(c1ccc(CCCCN)cc1)=N[C@H](CC(=O)OC(C)(C)C)c1nnc(C)n1-2] | tert-butyl (R)-2-(4-(4-(4-aminobutyl)phenyl)-2,3,9-trimethyl-6H-thieno[3,2-f][1,2,4]triazolo[4,3-a][1,4]diazepin-6-yl)acetate |
| 17 | 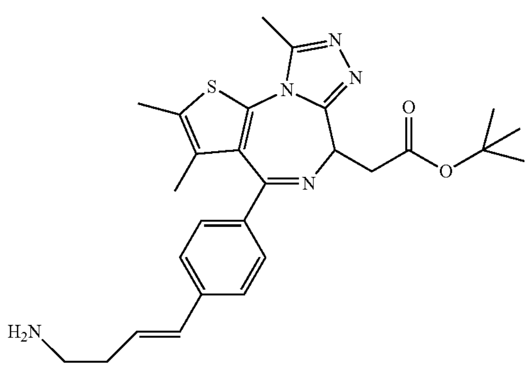 | tert-butyl (E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate |
| 17a | 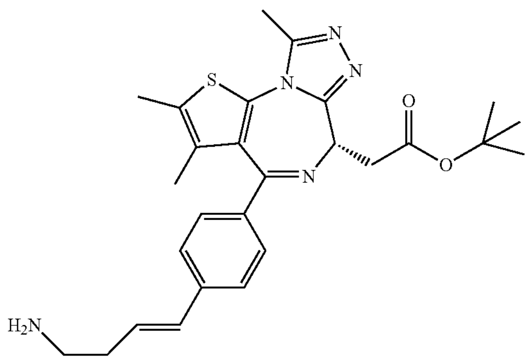 [SMILES: Cc1sc2c(c1C)C(c1ccc(/C=C/CCN)cc1)=N[C@@H](CC(=O)OC(C)(C)C)c1nnc(C)n1-2] | tert-butyl (S,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 17b | 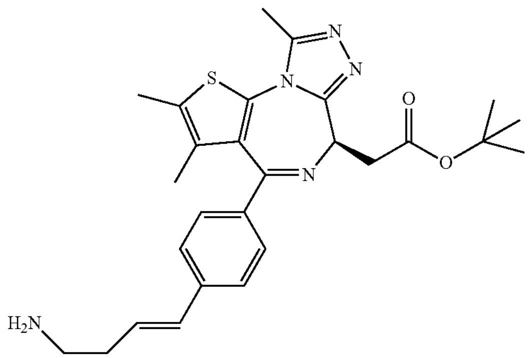 [SMILES: Cc1sc2c(c1C)C(c1ccc(/C=C/CCN)cc1)=N[C@H](CC(=O)OC(C)(C)C)c1nnc(C)n1-2] | tert-butyl (R,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate |
| 18 | 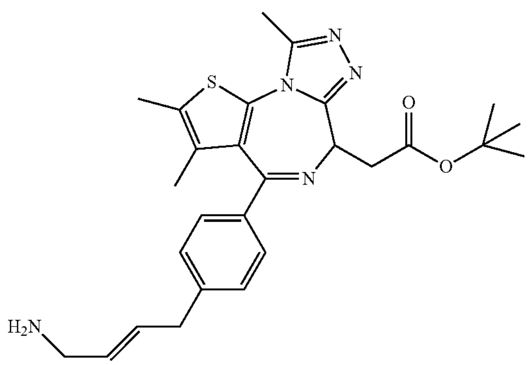 [SMILES: Cc1sc2c(c1C)C(c1ccc(C/C=C/CN)cc1)=NC(CC(=O)OC(C)(C)C)c1nnc(C)n1-2] | tert-butyl (E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate |
| 18a | 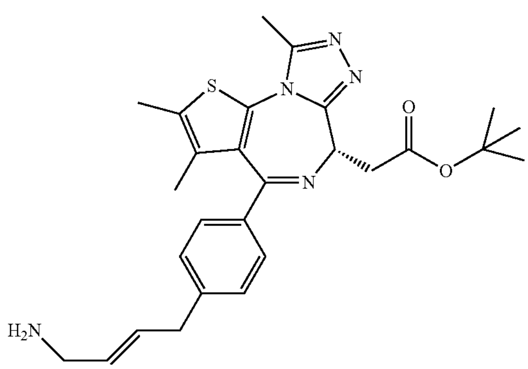 [SMILES: Cc1sc2c(c1C)C(c1ccc(C/C=C/CN)cc1)=N[C@@H](CC(=O)OC(C)(C)C)c1nnc(C)n1-2] | tert-butyl (S,E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate |
| 18b | 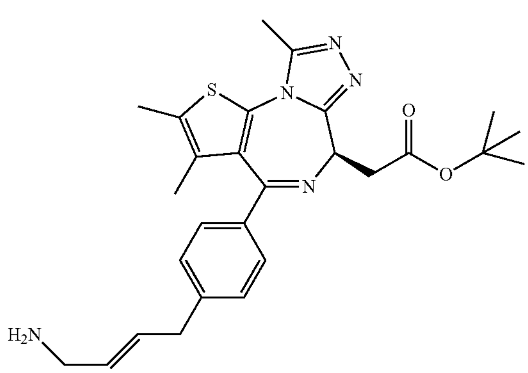 [SMILES: Cc1sc2c(c1C)C(c1ccc(C/C=C/CN)cc1)=N[C@H](CC(=O)OC(C)(C)C)c1nnc(C)n1-2] | tert-butyl (R,E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 19 | 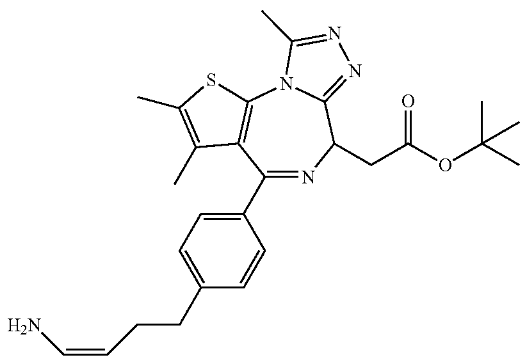 | tert-butyl (Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate |
| 19a | 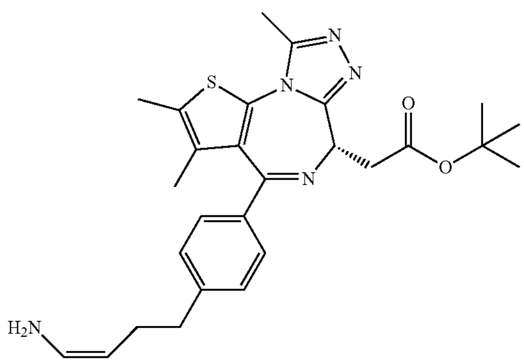 [SMILES: Cc1sc2c(c1C)C(c1ccc(CC/C=C\N)cc1)=N[C@@H](CC(=O)OC(C)(C)C)c1nnc(C)n1-2] | tert-butyl (S,Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate |
| 19b | 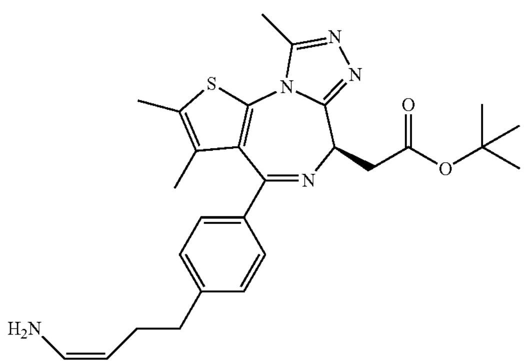 [SMILES: Cc1sc2c(c1C)C(c1ccc(CC/C=C\N)cc1)=N[C@H](CC(=O)OC(C)(C)C)c1nnc(C)n1-2] | tert-butyl (R,Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate |
| 20 | 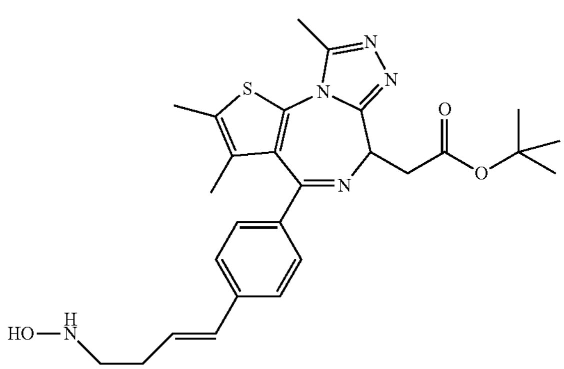 [SMILES: Cc1sc2c(c1C)C(c1ccc(/C=C/CCNO)cc1)=NC(CC(=O)OC(C)(C)C)c1nnc(C)n1-2] | tert-butyl (E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 20a | 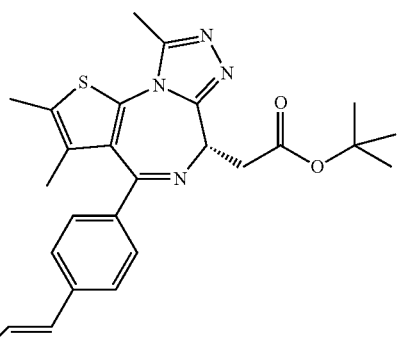 | tert-butyl (S,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate |
| 20b | 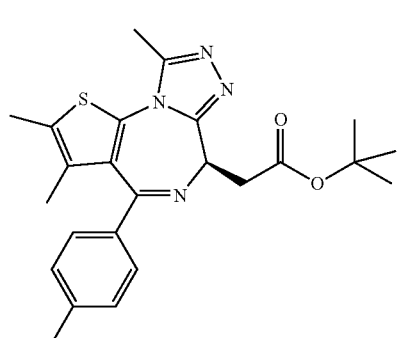 | tert-butyl (R,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate |
| 21 | 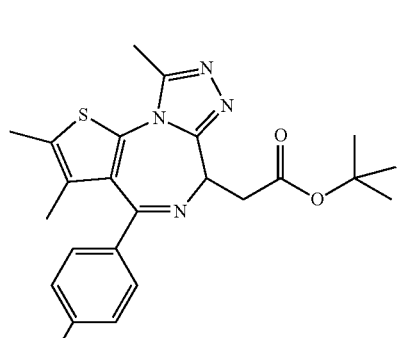 | tert-butyl (E)-2-(4-(4-(4-(hydroxyamino)but-2-en-1-yl)phenyl)-2,3,9-trimethyl-6H-thieno[3,2-f][1,2,4]triazolo[4,3-a][1,4]diazepin-6-yl)acetate |
| 21a | 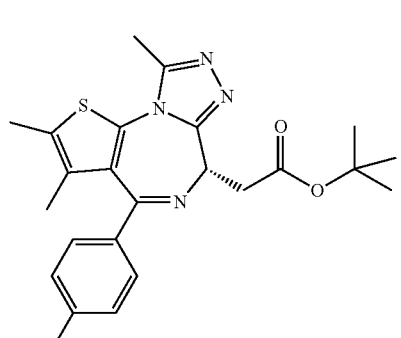 | tert-butyl (R,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name |
|---|---|---|
| 21b | 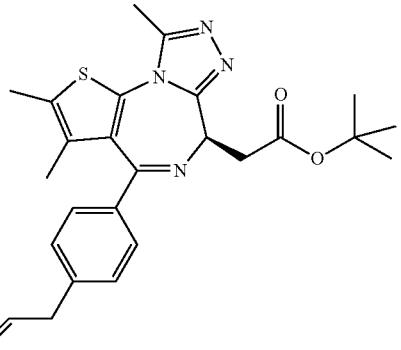 | tert-butyl (R,E)-2-(4-(4-(4-(hydroxyamino)but-2-en-1-yl)phenyl)-2,3,9-trimethyl-6H-thieno[3,2-f][1,2,4]triazolo[4,3-a][1,4]diazepin-6-yl)acetate |
| 22 | 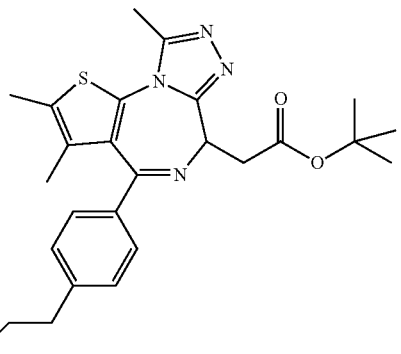 | tert-butyl (Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate |
| 22a | 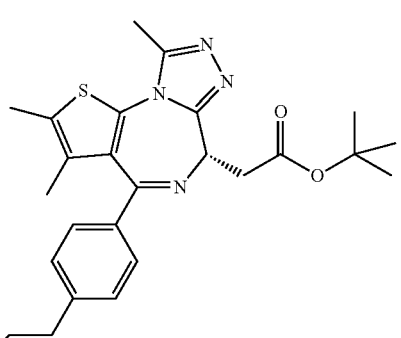 | tert-butyl (S,Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate |
| 22b | 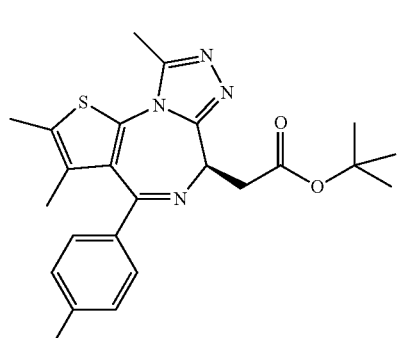 | tert-butyl (R,Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 23 | 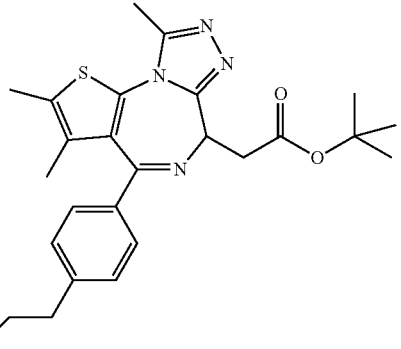 | tert-butyl 2-(4-(4-(4-(hydroxyamino)butyl)phenyl)-2,3,9-trimethyl-6H-thieno[3,2-f][1,2,4]triazolo[4,3-a][1,4]diazepin-6-yl)acetate |
| 23a | 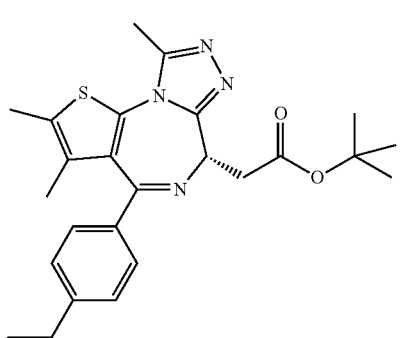 | tert-butyl (S)-2-(4-(4-(4-(hydroxyamino)butyl)phenyl)-2,3,9-trimethyl-6H-thieno[3,2-f][1,2,4]triazolo[4,3-a][1,4]diazepin-6-yl)acetate |
| 23b | 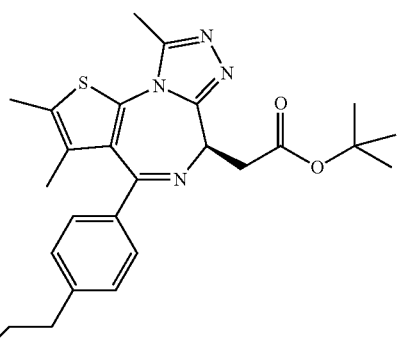 | tert-butyl (R)-2-(4-(4-(4-(hydroxyamino)butyl)phenyl)-2,3,9-trimethyl-6H-thieno[3,2-f][1,2,4]triazolo[4,3-a][1,4]diazepin-6-yl)acetate |
| 24 | 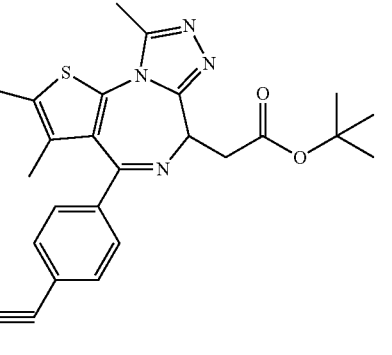 | tert-butyl 2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name |
|---|---|---|
| 24a | 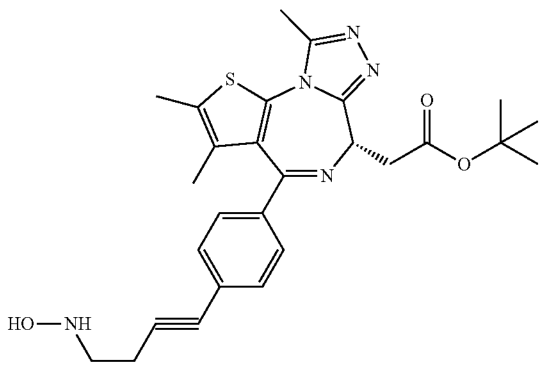 [SMILES: Cc1sc2c(c1C)C(c1ccc(C#CCCNO)cc1)=N[C@@H](CC(=O)OC(C)(C)C)c1nnc(C)n1-2] | tert-butyl (S)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate |
| 24b | 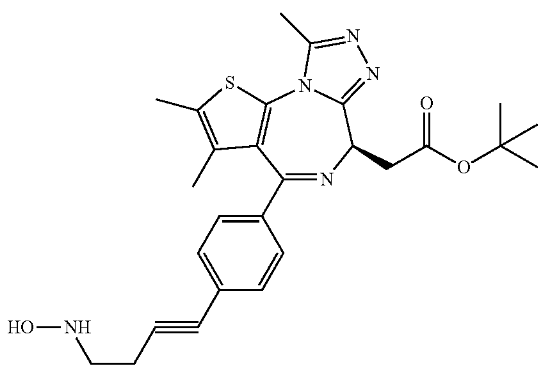 [SMILES: Cc1sc2c(c1C)C(c1ccc(C#CCCNO)cc1)=N[C@H](CC(=O)OC(C)(C)C)c1nnc(C)n1-2] | tert-butyl (R)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate |
| 25 | 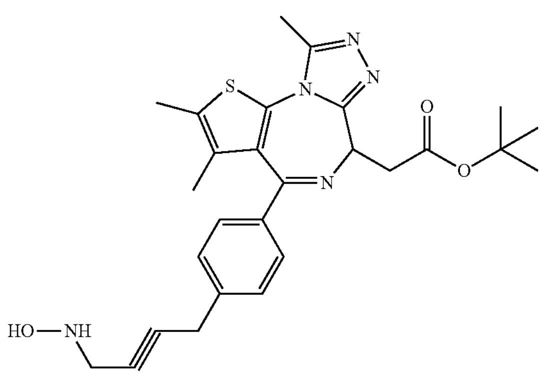 [SMILES: Cc1sc2c(c1C)C(c1ccc(CC#CCNO)cc1)=NC(CC(=O)OC(C)(C)C)c1nnc(C)n1-2] | tert-butyl 2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate |
| 25a | 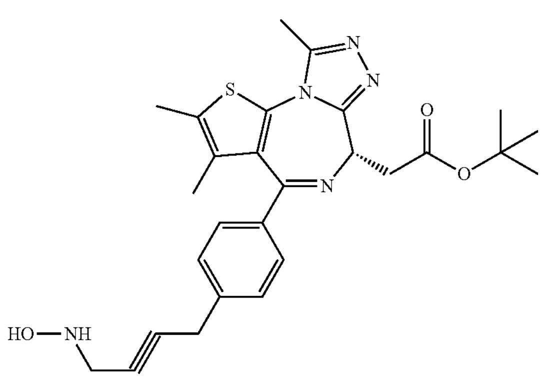 [SMILES: Cc1sc2c(c1C)C(c1ccc(CC#CCNO)cc1)=N[C@@H](CC(=O)OC(C)(C)C)c1nnc(C)n1-2] | tert-butyl (S)-2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 25b | 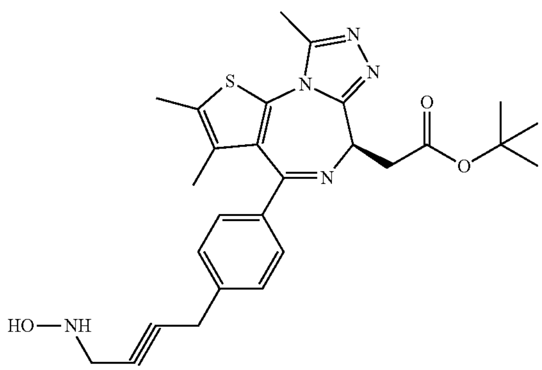 [SMILES: Cc1sc2c(c1C)C(c1ccc(CC#CCNO)cc1)=N[C@H](CC(=O)OC(C)(C)C)c1nnc(C)n1-2] | tert-butyl (R)-2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate |
| 26 | 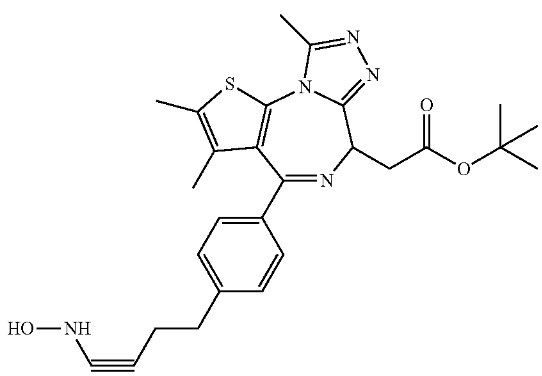 [SMILES: Cc1sc2c(c1C)C(c1ccc(CCC#CNO)cc1)=NC(CC(=O)OC(C)(C)C)c1nnc(C)n1-2] | tert-butyl 2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate |
| 26a | 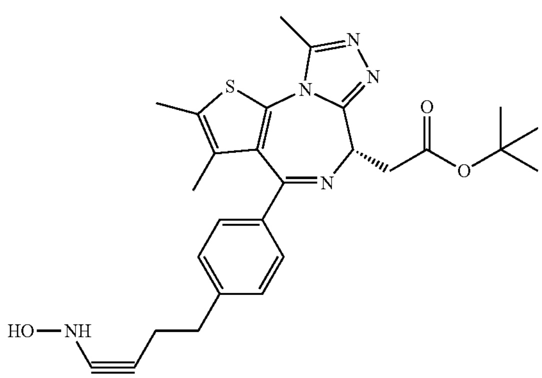 [SMILES: Cc1sc2c(c1C)C(c1ccc(CCC#CNO)cc1)=N[C@@H](CC(=O)OC(C)(C)C)c1nnc(C)n1-2] | tert-butyl (S)-2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate |
| 26b | 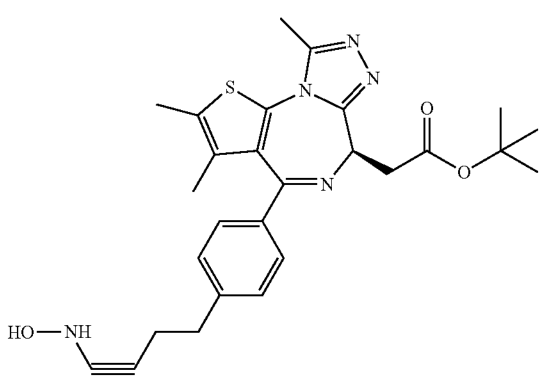 [SMILES: Cc1sc2c(c1C)C(c1ccc(CCC#CNO)cc1)=N[C@H](CC(=O)OC(C)(C)C)c1nnc(C)n1-2] | tert-butyl (R)-2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 27 | 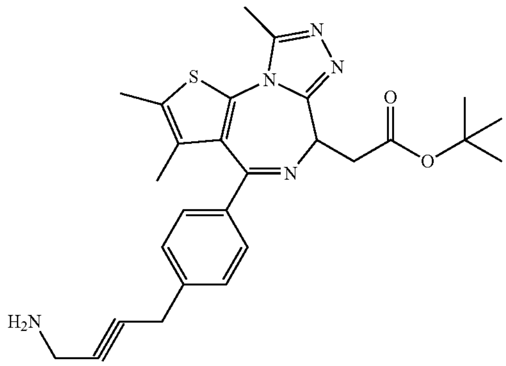 [SMILES: Cc1sc2c(c1C)C(c1ccc(CC#CCN)cc1)=NC(CC(=O)OC(C)(C)C)c1nnc(C)n1-2] | tert-butyl 2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate |
| 27a | 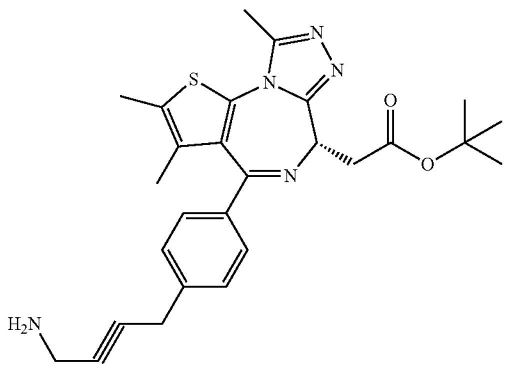 [SMILES: Cc1sc2c(c1C)C(c1ccc(CC#CCN)cc1)=N[C@@H](CC(=O)OC(C)(C)C)c1nnc(C)n1-2] | tert-butyl (S)-2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate |
| 27b | 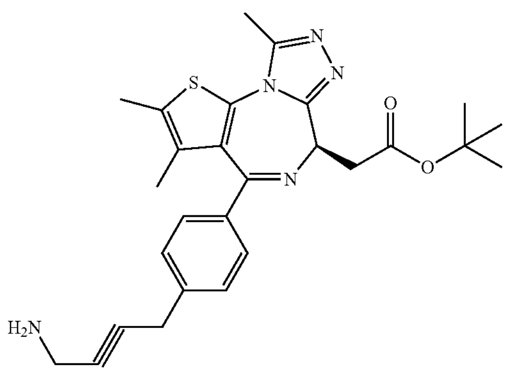 [SMILES: Cc1sc2c(c1C)C(c1ccc(CC#CCN)cc1)=N[C@H](CC(=O)OC(C)(C)C)c1nnc(C)n1-2] | tert-butyl (R)-2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate |
| 28 | 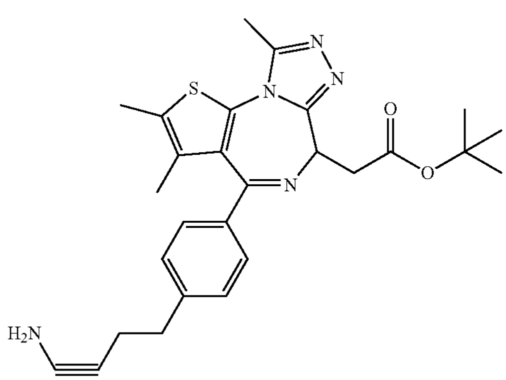 [SMILES: Cc1sc2c(c1C)C(c1ccc(CCC#CN)cc1)=NC(CC(=O)OC(C)(C)C)c1nnc(C)n1-2] | tert-butyl 2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate |

TABLE 1-continued

| Compound No. | Structure | Name[1] |
|---|---|---|
| 28a | 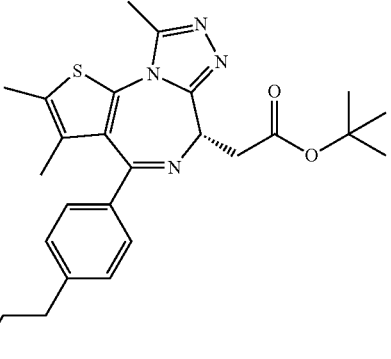 | tert-butyl (S)-2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate |
| 28b | 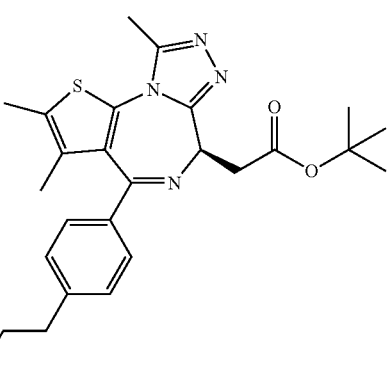 | tert-butyl (R)-2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate |

[1]Compound names were auto-generated using ChemDraw ® software version 17.0.0.206.

In one embodiment, the present disclosure is directed to a compound selected from the group consisting of

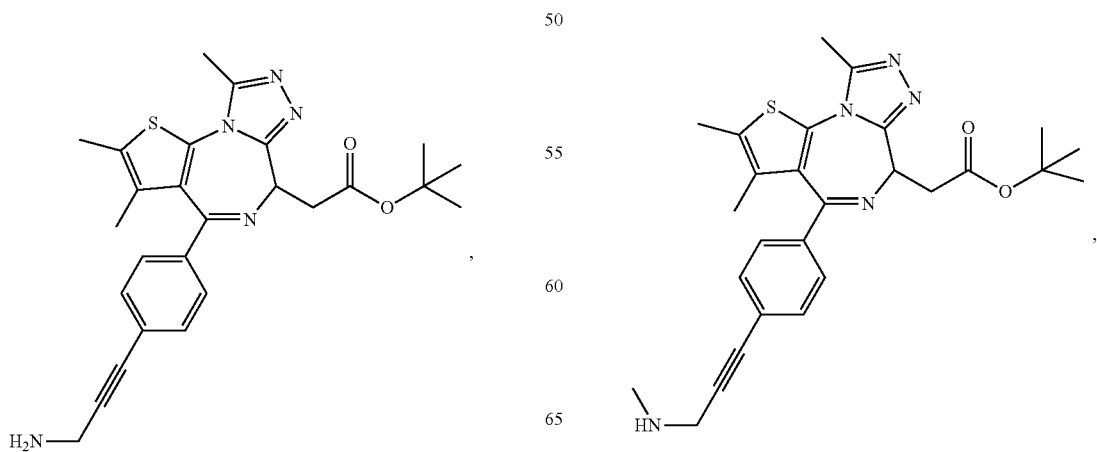

105
-continued
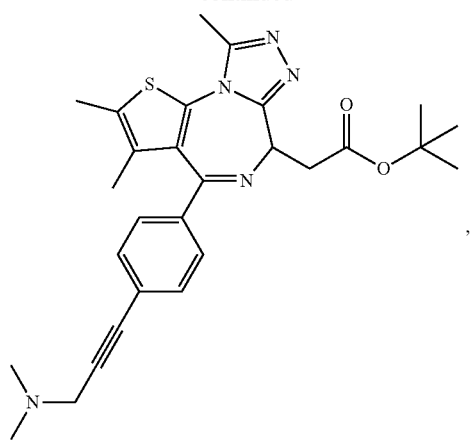
,
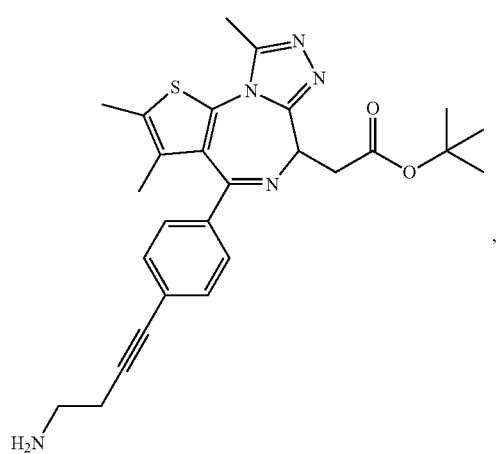
,
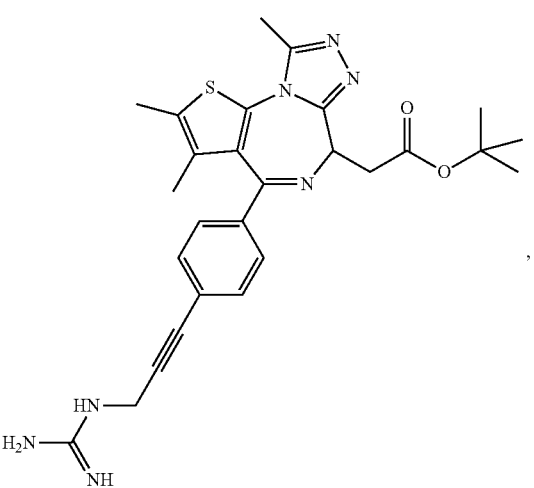
,
106
-continued
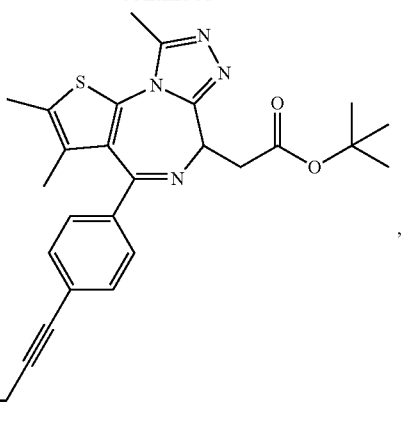
,
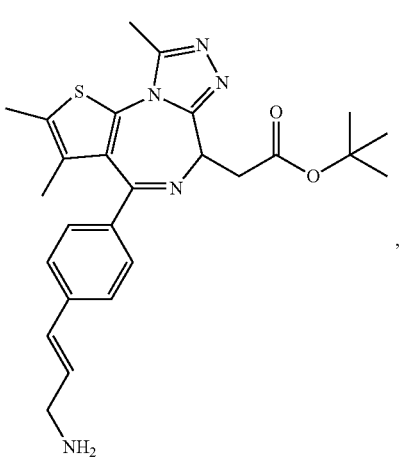
,
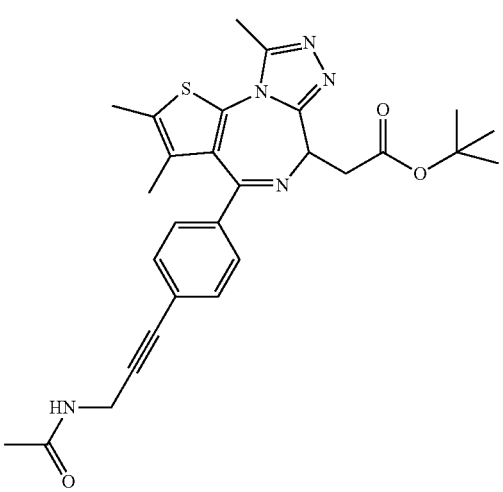
, 107
-continued
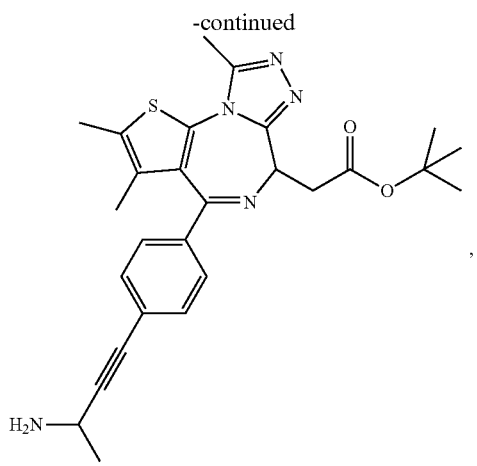
,
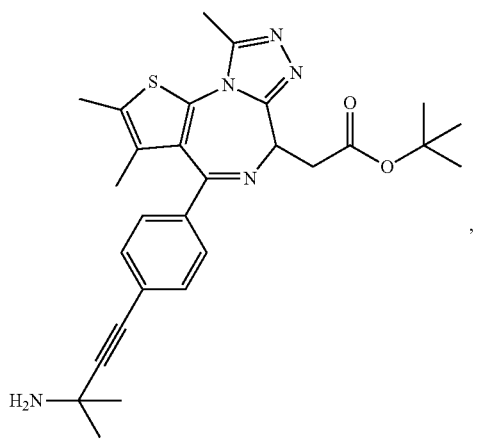
,
108
-continued
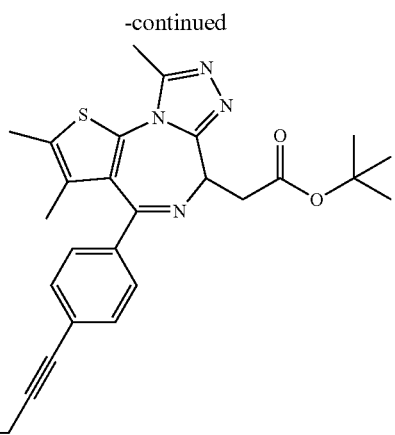
,
or a salt (e.g., a pharmaceutically acceptable salt) or an enantiomer thereof.
In one embodiment, the present disclosure is directed to a compound selected from the group consisting of:
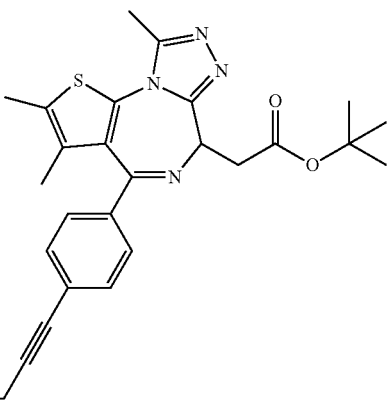
,
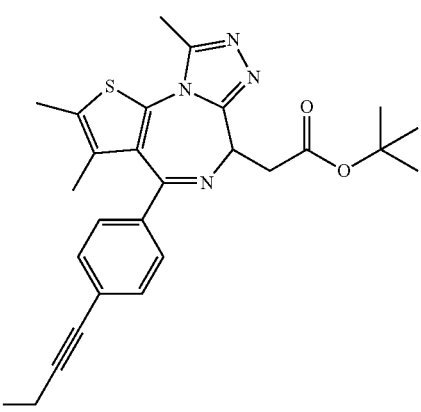
, and

109
-continued
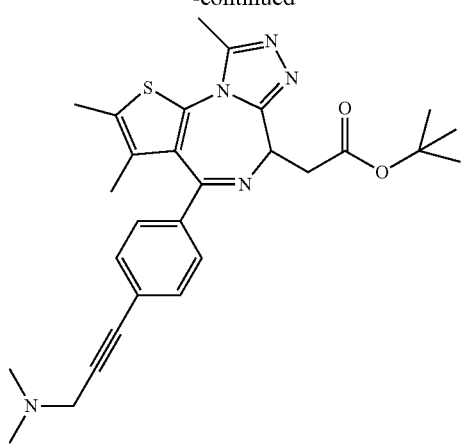
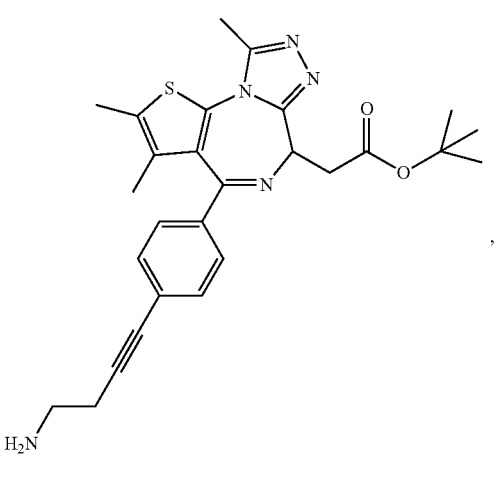
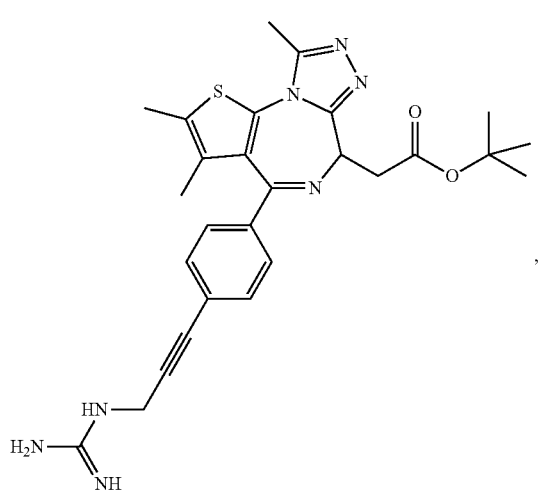
110
-continued
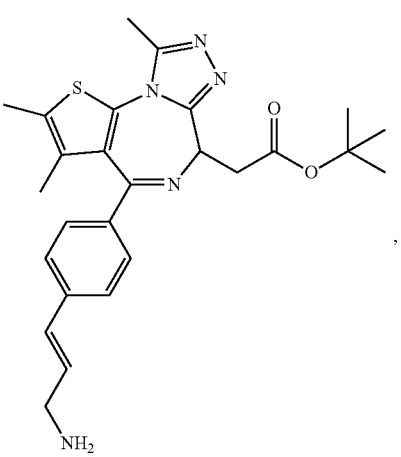
, and
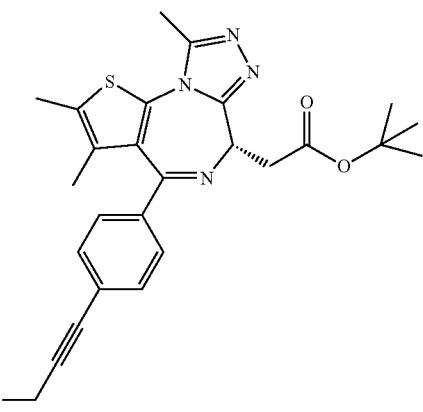
or a salt (e.g., a pharmaceutically acceptable salt) or an enantiomer thereof.
In one embodiment, the present disclosure is directed to a compound selected from the group consisting of:

111
-continued
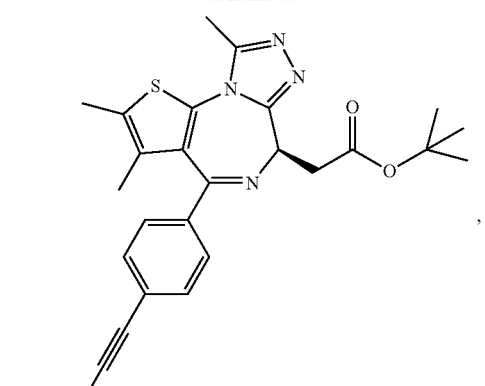
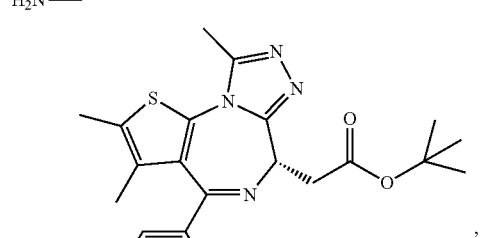
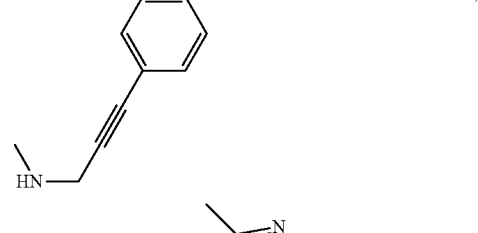
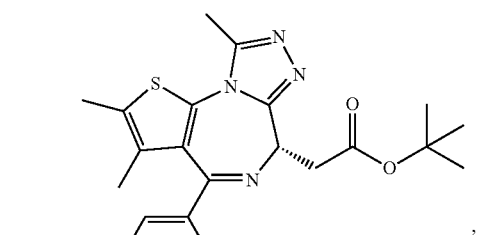
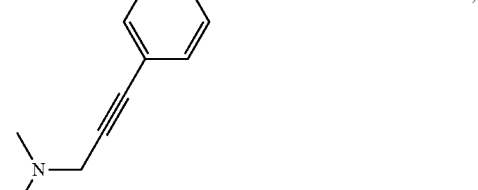
112
-continued
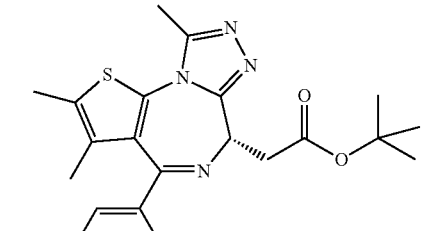
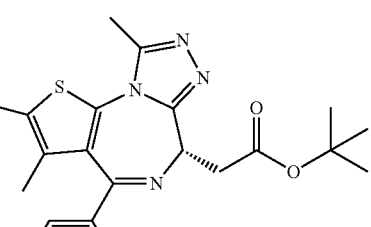
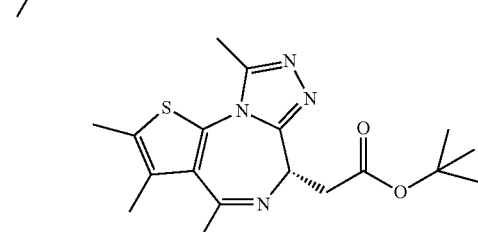
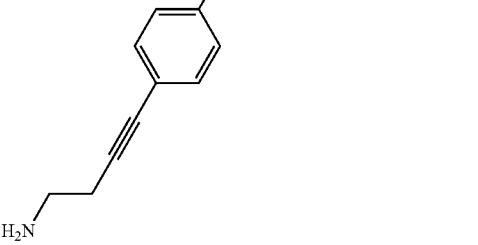
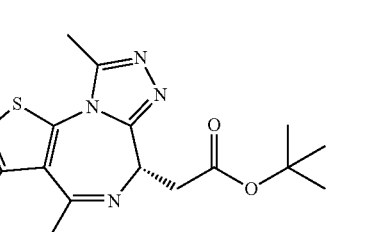
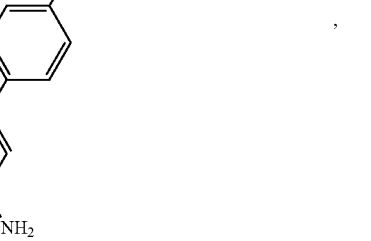

113
-continued
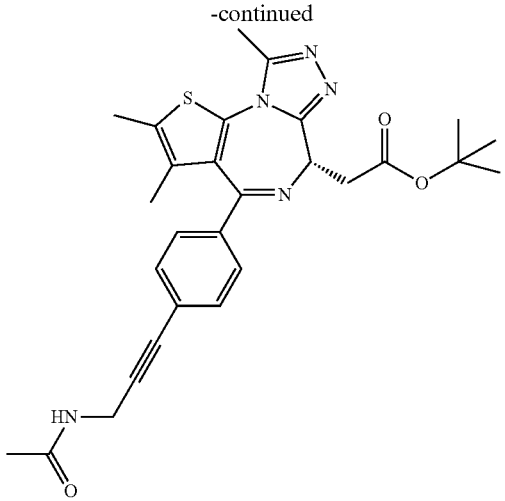
114
-continued
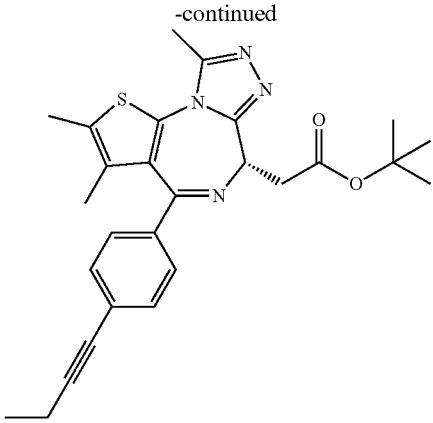
, and
, or a salt (e.g., a pharmaceutically acceptable salt) thereof.
In one embodiment, the present disclosure is directed to a compound selected from the group consisting of:

115
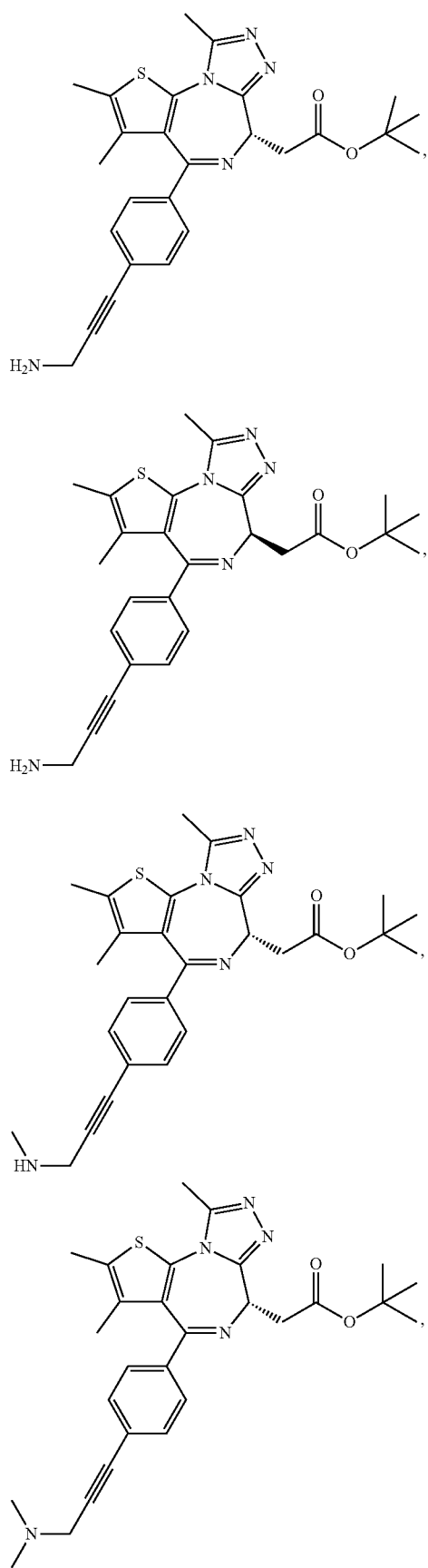
116
-continued
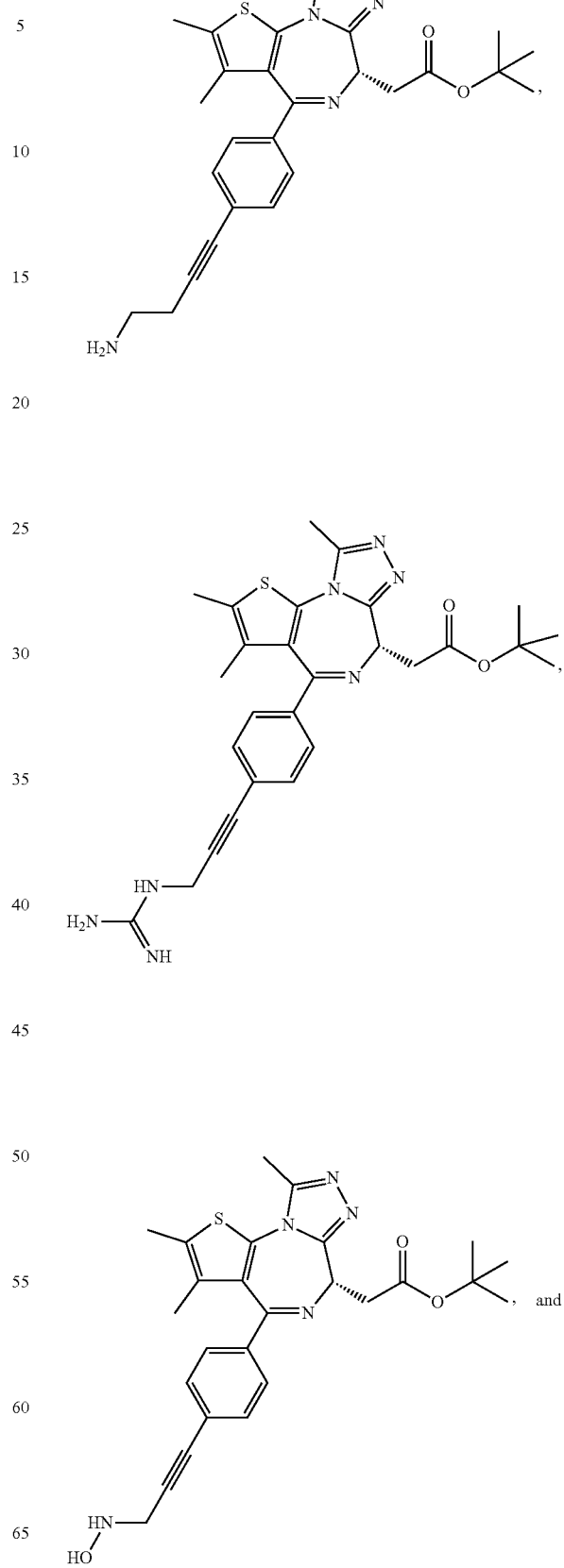

-continued

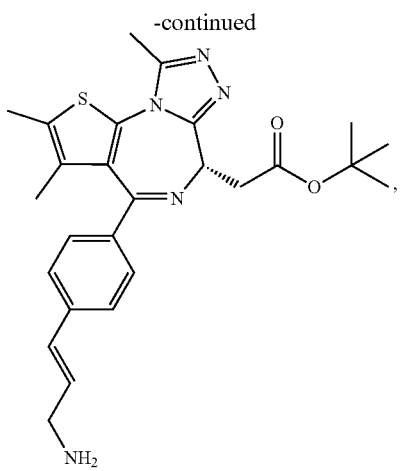

or a pharmaceutically acceptable salt thereof.

Referring now to a compound of the present disclosure, as described herein, these can exist in solid or liquid form. In the solid state, the compound may exist in crystalline or noncrystalline form, or as a mixture thereof. The skilled artisan will appreciate that pharmaceutically acceptable solvates may be formed from crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The subject matter described herein includes such solvates.

The skilled artisan will further appreciate that certain compounds described herein that exist in crystalline form, including the various solvates thereof, may exhibit polymorphism (i.e. the capacity to occur in different crystalline structures). These different crystalline forms are typically known as "polymorphs." The subject matter disclosed herein includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds described herein or a salts thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined hereinabove.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds as disclosed herein and salts (e.g., pharmaceutically acceptable salts) thereof that contain the aforementioned isotopes and/or other isotopes of other atoms are within the scope of the subject matter disclosed herein. Isotopically-labelled compounds are disclosed herein, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are commonly used for their ease of preparation and detectability. $^{11}C$ and $^{18}F$ isotopes are useful in PET (positron emission tomography), and $^{125}I$ isotopes are useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I can generally be prepared by carrying out the procedures disclosed in the Schemes and/or in the Examples below, by substituting a readily available isotopically labelled reagent for a non-isotopically labelled reagent.

III. Formulations

In an additional aspect, the description provides therapeutic or pharmaceutical compositions comprising an effective amount of at least one of the compounds as described herein, including, e.g., at least one compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, and combinations thereof. Pharmaceutical compositions comprising an effective amount of at least one compound according to the present disclosure, and optionally one or more of the compounds otherwise described herein, in effective amounts, in combination with a pharmaceutically effective amount of a carrier, additive or excipient, and optionally an additional bioactive agent, represents a further aspect of the disclosure.

In certain embodiments, the compositions comprise pharmaceutically acceptable salts, in particular, acid or base addition salts of compounds as described herein. The acids that are used to prepare the pharmaceutically acceptable acid addition salts of the aforementioned base compounds include those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compositions as described herein may in certain embodiments be administered in single or divided unit doses by the oral, parenteral or topical routes. Administration of the compounds may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, by inhalation spray, rectally, vaginally, or via an implanted reservoir, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound according to the present disclosure, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but may also be administered in suppository and transdermal or other topical forms. Intramuscular injections in liposomal form may also be used to control or sustain the release of compound at an injection site.

Thus in one aspect, pharmaceutical formulations of compounds as described herein can be prepared for parenteral administration with a pharmaceutically acceptable parenteral vehicle and in a unit dosage injectable form. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. A compound of the present disclosure, having the desired degree of purity, is optionally mixed with one or more pharmaceutically acceptable excipients (Remington's Pharmaceutical Sciences (1980) 16th edition, Osol, A. Ed.), in the form of a lyophilized formulation for reconstitution or an aqueous solution.

The compositions of the present disclosure may be formulated in a conventional manner using one or more pharmaceutically acceptable carriers and may also be administered in controlled-release formulations. The compounds of the disclosure can be formulated in accordance with standard pharmaceutical practice as a pharmaceutical composition. According to this aspect, there is provided a pharmaceutical composition comprising a compound of the present disclosure, e.g., a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, in association with one or more pharmaceutically acceptable excipients.

A typical formulation is prepared by mixing the compounds of the disclosure with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the compound is being applied. Other pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the compound of the present disclosure or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The pharmaceutical compositions may be in the form of a sterile injectable preparation, such as a sterile injectable aqueous or oleaginous suspension. In particular, formulations to be used for in vivo administration must be sterile. Such sterilization is readily accomplished by filtration through sterile filtration membranes. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables, as well as natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compositions of the present disclosure ordinarily can be stored as a solid composition, a lyophilized formulation or as an aqueous solution.

The pharmaceutical compositions comprising a compound of the present disclosure can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the disorder. Such amount is preferably below the amount that is toxic to the host or renders the host significantly more susceptible to unwanted side effects.

The compound of the present disclosure can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present disclosure can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

The active compound (e.g., a compound of the present disclosure or a salt thereof) is included in the pharmaceutically acceptable carrier or diluent in an amount sufficient to deliver to a patient a therapeutically effective amount for the desired indication, without causing serious toxic effects in the patient treated. A preferred dose of the active compound for the herein-mentioned conditions is in the range from about 10 ng/kg to 300 mg/kg, preferably 0.1 to 100 mg/kg per day, more generally 0.5 to about 25 mg per kilogram body weight of the recipient/patient per day. One typical daily dosage might range from about 1 μg/kg to 100 mg/kg or more, depending on the factors mentioned above. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.00001-0.01 mM, or in other embodiments, about 0.1-30 mM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted overtime according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s)(such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally or by any other desired route.

IV. Indications and Methods of Treatment

It is contemplated that the compounds disclosed herein may be used to treat various diseases or disorders. Generally, the disease or disorder to be treated is a hyperproliferative disease such as cancer.

In one embodiment, the present disclosure is directed to the use of a compound of the present disclosure (e.g., a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof) for the inhibition of a bromodomain (in vitro or in vivo). In one embodiment, the bromodomain is a bromodomain-containing protein 4 (BRD4).

In certain embodiments, the present disclosure is directed to a method of treating a disease or disorder in a subject (e.g., a human subject) in need thereof, comprising administering to the subject (e.g., a human subject) an effective amount of a compound of the present disclosure (e.g., a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb)), or a salt (e.g., a pharmaceutically acceptable salt) thereof, or a pharmaceutical composition of the present disclosure that comprises said compound or salt and one or more pharmaceutically acceptable excipients.

In one embodiment, the disease or disorder is a bromodomain-mediated disorder. Thus, another embodiment includes a method for treating a bromodomain-mediated disorder in a subject in need thereof, comprising administering to the subject an effective amount of a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, or a pharmaceutical composition of the present disclosure that comprises said compound or salt and one or more pharmaceutically acceptable excipients. Bromodomain-mediated disorders include, but are not limited to those disorders described herein.

Another embodiment is directed to a method of degrading a bromodomain-containing protein in a cell, the method comprising exposing the cell to a composition comprising an effective amount of a compound of the present disclosure (e.g., a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof), wherein the compound effectuates the degradation of the bromodomain-containing protein. The term "degrading", when used in connection with degrading a bromodomain-containing protein in a cell, means the level of the protein in the cell is reduced. In one particular embodiment, the bromodomain-containing protein is a BRD4. The cell may be, for example, any animal cell, including human cells.

Another embodiment includes a method of treating cancer in an subject comprising administering to the subject an effective amount of a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, or a pharmaceutically acceptable composition comprising said compound or salt.

Another embodiment includes a method of treating cancer in an subject comprising administering to the subject an effective amount of (a) a compound of Formula (I), (Ia), (Ib), (II), (IIa), (IIb), (III), (IIIa), (IIIb), (IV), (IV-1), (IVa), (IVb), (IV-1a), (IV-11b), (V), (Va), (Vb), (VI), (VI-1), (VIa), (VIb), (VI-1a), (VI-1b), (VII), (VIIa), (VIIb), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, and (b) a cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, a compound of the present disclosure or a salt thereof is used in a method of treating solid tumor, e.g., ovarian.

In an embodiment, a compound of the present disclosure or a salt thereof is used in a method of treating ovarian, breast and pancreatic cancers. The cancer may be associated with the expression or activity of a MUC16/CA125/O772P polypeptide. See, e.g., WO 2007/001851; U.S. Pat. Nos. 7,989,595; 8,449,883; 7,723,485; Chen et al (2007) *Cancer Res.* 67(10): 4924-4932; Junutula, et al., (2008) *Nature Biotech.*, 26(8):925-932.

In certain embodiments, a compound of the present disclosure or a salt thereof is used in a method of treating cancer, e.g., breast or gastric cancer, more specifically HER2 positive breast or gastric cancer, wherein the method comprises administering such compound to a patient in need of such treatment.

Another embodiment includes a method of increasing efficacy of a cancer treatment in a subject comprising administering to the subject an effective amount of a compound of the present disclosure or a salt (e.g., a pharmaceutically acceptable salt) thereof and a cytotoxic agent.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

A compound of the present disclosure or a salt thereof may be administered by any route appropriate to the condition to be treated. The compound will typically be administered parenterally, i.e. infusion, subcutaneous, intramuscular, intravenous, intradermal, intrathecal and epidural.

Bromodomain-Mediated Disorders

A "bromodomain-mediated disorder" is characterized by the participation of one or more bromodomains (e.g., BRD4) in the inception, manifestation of one or more symptoms or disease markers, severity, or progression of a disorder. Bromodomains include, but are not limited to ASH1L, ATAD2, ATAD2B, BAZ1A, BAZ1B, BAZ2A, BAZ2B, BPTF, BRD1, BRD2, BRD3, BRD4, BRD7, BRD8, BRD9, BRDT, BRPF1, BRPF3, BRWD1, BRWD3, CECR2, CRE-BBP (aka, CBP), EP300, GCN5L2, KIAA2026, MLL, MLL4, PBRM, PCAF, PHIP, SMARCA2, SMARCA4, SP100, SP110, SP140, SP140L, TAF1, TAF1L, TRIM24, TRIM28, TRIM33, TRIM66, ZMYND8, and ZMYND11.

Bromodomain-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

Bromodomain-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis *nodosa*, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Bromodomain-mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radio-contrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

Bromodomain inhibitors may also be used to provide male contraception.

Co-Administration

A compound of the present disclosure can be used either alone or in combination with other agents in a therapy. For instance, a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, may be co-administered with at least one additional therapeutic agent. Such combination therapies noted above encompass combined administration (where two or more therapeutic agents are included in the same or separate formulations), and separate administration, in which case, administration of the compound of the present disclosure can occur prior to, simultaneously (e.g., concurrently), and/or following, administration of the additional therapeutic agent and/or adjuvant. A compound of the present disclosure or a salt thereof can also be used in combination with radiation therapy.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of coadministered compounds or compositions are found in the subject at a given time.

In an additional aspect, the description provides combination therapies comprising an effective amount of a compound as described herein in combination with an additional bioactive agent. The term "bioactive agent" is used to describe an agent, other than a compound as described herein, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc. In certain embodiments, the compound as described herein, the additional bioactive agent or both are present in an effective amount or, in certain embodiments, a synergistically effective amount.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C$_{11}$, CHIR-258); 3-[5-(methylsulfonylpiperadinemethyl)-indolyl-quinolone, vatalanib, AG-013736, AVE-0005, the acetate salt of [D-Ser(Bu$^t$)$_6$,Azgly$^{10}$] or pyro-Glu-His-Trp-Ser-Tyr-D-Ser(But)-Leu-Arg-Pro-Azgly-NH$_2$ acetate [C$_{59}$H$_{84}$N$_{18}$O$_{14}$·(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafamib, BMS-214662, tipifamib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

For treating an inflammatory disease or an autoimmune disease, a compound of the present disclosure or a salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-IRI, siL-6R), an antiinflammatory cytokine (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCIO-469, VX-702, AMG-548, VX-740, Roflumilast, IC-485, CDC-801, SIP1 agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-IRI, siL-IRII, siL-6R), and an antiinflammatory cytokine (e.g. IL-4, IL-10, IL-11, IL-13 or TGF).

For treating Crohn's disease, a compound of the present disclosure or a salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of the present disclosure or a salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-1ra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of the present disclosure or a salt thereof may be co-administered with a corticosteroid; prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3)(Interferon Sciences/Fujimoto), interferon-(Alfa Wassermann/J&J), interferon 1A-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g.

TNF, LT, IL-1, IL-2, IL-6, IL-7, IL-8, IL-12, IL-23, IL-15, IL-16, EMAP-II, GM-CSF, FGF, or PDGF).

The term "anti-HIV agent" or "additional anti-HIV agent" includes, for example, nucleoside reverse transcriptase inhibitors (NRTI), other non-nucleoeside reverse transcriptase inhibitors (i.e., those which are not representative of the present disclosure), protease inhibitors, fusion inhibitors, among others, exemplary compounds of which may include, for example, 3TC(Lamivudine), AZT (Zidovudine), (–)-FTC, ddI (Didanosine), ddC (zalcitabine), abacavir (ABC), tenofovir (PMPA), D-D4FC(Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure or salts thereof include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4''-dimethoxy-5',5''-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), 5Cl3PhS-2Indo1CONH2 (5-chloro-3-(phenylsulfinyl)-2'-indolecarboxamide), AAP-BHAP (U-104489 or PNU-104489), Capravirine (AG-1549, 5-1153), atevirdine (U-87201E), aurin tricarboxylic acid (SD-095345), 1-[(6-Cyano-2-indoyly)carbonyl]-4-[3-(isopropylamino)-2-pyridinyl]piperazine (piperazine1 pyridine 4 indolyl derivative), 1-[5-[[N-(methyl)methylsulfonylamino]-2-indolylcarbonyl-4-[3-(isopropylamino)-2-pyridinyl]piperazine (piperazine 1pyridine 5 indolyl derivative), 1-[3-(Ethylamino)-2-[pyridinyl]-4-[(5-hydroxy-2-indolyl)carbonyl]piperazine, 1-[(6-Formyl-2-indoyly) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]hiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo [2,3-a]isoindol-5(9bH)-one, Tivirapine (R86183), UC-38 and UC-84, among others.

For treating AIDS a compound of the present disclosure or a salt thereof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or a pharmaceutically acceptable salt thereof may also be co-administered with methotrexate, cyclosporine, FK506, rapamycin, mycophenolate mofetil, leflunomide, an SIPI agonist, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-IRI, siL-IRII, or siL-6R), or an antiinflammatory cytokine (e.g. IL-4, IL-10, IL-13 or TGF).

A compound of form the present disclosure or a salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNS03, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, an anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of the present disclosure or a salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of the present disclosure or a salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of the present disclosure or a salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of the present disclosure or a salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of the present disclosure or a salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of the present disclosure or a salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); a n inhibitor of PDE4, or a purine synthesis inhibitor (e.g. Cellcept®). For example, a compound of formula (I) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-Ira).

A compound of the present disclosure or a salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of the present disclosure or a salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of the present disclosure or a salt thereof can also be co-administered with LIP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™).

For treating type II diabetes, hepatic steatosis, insulin resistance, metabolic syndrome or a related disorder, a compound of the present disclosure or a salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of the present disclosure or a salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

Administration

A compound of the present disclosure or a salt thereof (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

For the prevention or treatment of disease, the appropriate dosage of a compound of the present disclosure or a salt thereof (when used alone or in combination with one or more other additional therapeutic agents) will depend on the type of disease to be treated, the type of compound, the severity and course of the disease, whether the compound or a salt thereof is administered for preventive or therapeutic purposes, previous therapy, the patient's clinical history and response to the compound, and the discretion of the attending physician. The compound of the present disclosure or a salt thereof is suitably administered to the patient at one time or over a series of treatments. Depending on the type and severity of the disease, about 10 ng/kg to 300 mg/kg (e.g. 0.1 mg/kg-10 mg/kg) of a compound of the present disclosure or a salt thereof can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of a compound of the present disclosure or a salt thereof would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses). An initial higher loading dose, followed by one or more lower doses may be administered. However, other dosage regimens may be useful. The progress of this therapy is easily monitored by conventional techniques and assays.

V. Articles of Manufacture

In another aspect, described herein are articles of manufacture, for example, a "kit", containing materials useful for the treatment of the diseases and disorders described above is provided. The kit comprises a container comprising a compound of the present disclosure or a salt thereof. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products.

Suitable containers include, for example, bottles, vials, syringes, blister pack, etc. A "vial" is a container suitable for holding a liquid or lyophilized preparation. In one embodiment, the vial is a single-use vial, e.g. a 20-cc single-use vial with a stopper. The container may be formed from a variety of materials such as glass or plastic. The container may hold a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, or a formulation thereof which is effective for treating the condition and may have a sterile access port (for example, the container may be an intravenous solution bag or a vial having a stopper pierceable by a hypodermic injection needle).

At least one active agent in the composition is a compound of the present disclosure or a salt thereof. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of the present disclosure or a salt thereof can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound or a salt thereof and, if present, the second pharmaceutical formulation. For example, if the kit comprises a first composition comprising a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, and a second pharmaceutical formulation, the kit may further comprise directions for the simultaneous, sequential or separate administration of the first and second pharmaceutical compositions to a patient in need thereof.

In an embodiment, the kits are suitable for the delivery of solid oral forms of a compound of the present disclosure or a salt thereof, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of the present disclosure, e.g., a compound of Formula (I), (Ia), (Ib), (II), (IIa), (IIb), (III), (IIIa), (IIIb), (IV), (IV-1), (IVa), (IVb), (IV-1a), (IV-1b), (V), (Va), (Vb), (VI), (VI-1), (VIa), (VIb), (VI-1a), (VI-1b), (VII), (VIIa), (VIIb), (VIII), (VIIIa), (VIIIb), (IX), (IX-1), (IXa), (IXb), (IX-1a), (IX-1b), (X), (Xa) or (Xb), or a salt (e.g., a pharmaceutically acceptable salt) thereof, contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a compound of the present disclosure or a salt thereof and a second therapeutic agent, the kit may comprise a container for containing the separate compositions such as a divided bottle or a divided foil packet; however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

The following examples are offered by way of illustration and not by way of limitation.

Abbreviations

ACN—acetonitrile
$Ac_2O$—acetic anhydride
AIBN—2,2'-Azobis(2-methylpropionitrile)
ATP—adenosine triphosphate
Boc—tert-butyloxycarbonyl
BrettPhos—2-(Dicyclohexylphosphino)3,6-dimethoxy-2',4',6'-triisopropyl-1,1'-biphenyl
BrettPhos Pd-G3-[(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate
$Cy_2NMe$—N,N-Dicyclohexylmethylamine
DCM—dichloromethane
DIEA—N,N-diisopropylethylamine
DMA—dimethylacetamide
DMF—dimethylformamide
DMFA or DMF-DMA—dimethylformamide dimethyl acetal
DMSO—dimethylsulfoxide
$Et_3N$—triethylamine
$Et_2NH$—diethylamine
EtOAc—ethyl acetate
EtOH—ethanol
FA—formic acid
FBS—fetal bovine serum
HEPES—4-(2-hydroxyethyl)piperazine-1-ethanesulfonic acid
HOAc—acetic acid
HPLC—high performance liquid chromatography
KOAc—potassium acetate
LC—liquid chromatography
LCMS—liquid chromatography mass spectrometry
Me—methyl
MeI—methyl iodide
MeOH—methanol
MeOLi—lithium methoxide
$MeSO_2Na$—sodium methanesulphinate
MsCl—methanesulfonyl chloride
MTBE—methyl tert-butyl ether
MW—microwave
$NaBH(OAc)_3$—sodium triacetoxyborohydride
NBS—N-bromosuccinimide
NIS—N-iodosuccinimide
NMP—N-methyl-2-pyrrolidone
NMR—nuclear magnetic resonance
PBS—phosphate buffered saline
Pd/C—palladium on carbon
$Pd(Cy*Phine)_2Cl_2$—Bis[dicyclohexyl(2,4,6-triisopropyl-[1,1':3',1''-terphenyl]-2-yl)phosphane]palladium(II) dichloride
$Pd_2(dba)_3$—Tris(dibenzylideneacetone)dipalladium(0)
$Pd(dppf)Cl_2$—[1,1'-Bis(diphenylphosphino)ferrocene]dichloropalladium(II)
$Pd(Ph_3P)_4$—Tetrakis(triphenylphosphine)palladium(0)
PE—petroleum ether
Ph—phenyl
Phth—phthalimide
RT—retention time
SAR—structure activity relationship
SFC—supercritical fluid chromatography
SPhos—2-Dicyclohexylphosphino-2',6'-dimethoxybiphenyl
TBAF—tetrabutylammonium fluoride
TBSCl—tert-butyldimethylsilyl chloride
t-Bu—tert-butyl
$[t-Bu_3PH]^+BF_4^-$—tri-tert-butylphosphonium tetrafluoroborate
t-BuONO—tert-butyl nitrite
TCEP—tris(2-carboxyethyl)phosphine
TFA—trifluoroacetic acid
THF—tetrahydrofuran
TLC—thin layer chromatography
TMS—tetramethylsilane
Ts—tosyl
UV—ultraviolet LCMS Methods Method A: Experiments were performed using a MK RP18e 25-2 mm column, at a flow rate of 1.5 mL/min, and a mass spectrometer using ESI as ionization source. The solvent A was 1.5 mL of TFA in 4 L of water, and solvent B was 0.75 mL of TFA in 4 L of acetonitrile. The gradient consisted of 5-95% solvent B over 0.7 minutes, hold at 95% for 0.4 minutes. LC column temperature was 50° C. UV absorbance was collected at 220 nm and 254 nm.

SFC Methods

Method 1: SFC was performed using a Chiralpak® AD-3 column. The mobile phase was ethanol with 0.1% ethanol amine, with a 5-40% gradient and flow rate of 2.5 ml/min.

Compound A tert-butyl (S)-2-(4-(4-chlorophenyl)-2,3,9-trimethyl-6H-thieno[3,2-f][1,2,4]triazolo[4,3-a][1,4]diazepin-6-yl)acetate

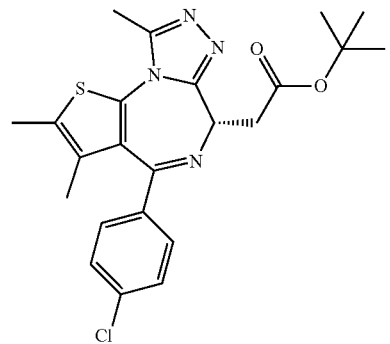 [SMILES: Cc1sc2c(c1C)C(c1ccc(Cl)cc1)=N[C@@H](CC(=O)OC(C)(C)C)c1nnc(C)n1-2]

141

Compound A is known in the art as "JQ1", and is described in Filippakopoulos et al. "Selective inhibition of BET bromodomains," Nature (2010), 468, 1067-1073; Romero, et al., J. Med. Chem. 59, 1271-1298 (2016).

Compound B tert-butyl (S)-2-(4-(4-iodophenyl)-2,3,9-trimethyl-6H-thieno[3,2-f][1,2,4]triazolo[4,3-a][1,4]diazepin-6-yl)acetate

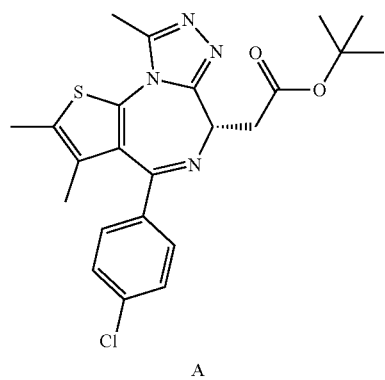

A

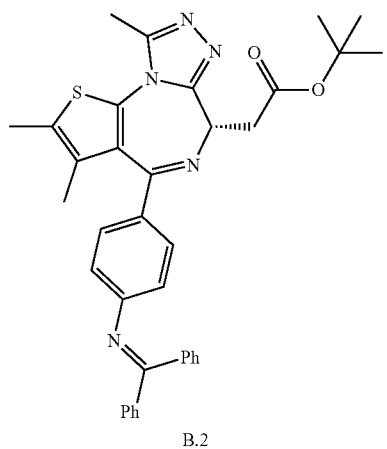

B.2

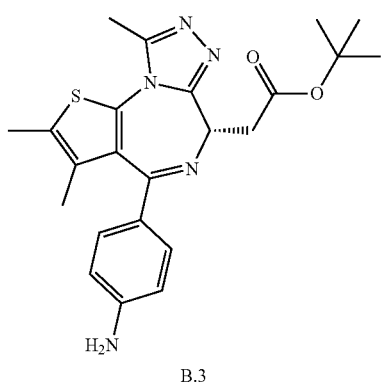

B.3

142

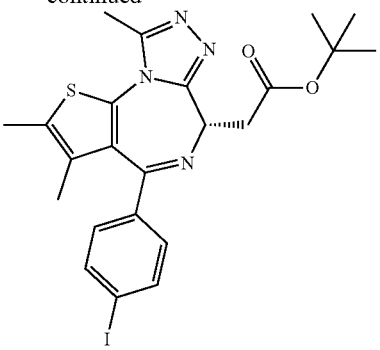

B

Step 1: tert-butyl (S)-2-(4-(4-((diphenylmethylene)amino)phenyl)-2,3,9-trimethyl-6H-thieno[3,2-f][1,2,4]triazolo[4,3-a][1,4]diazepin-6-yl)acetate

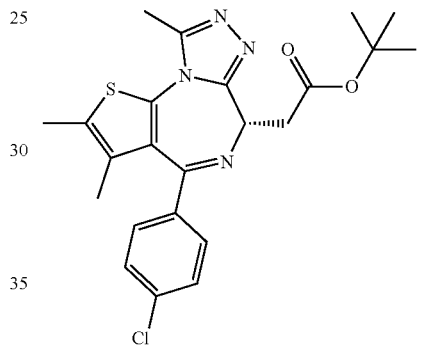

A

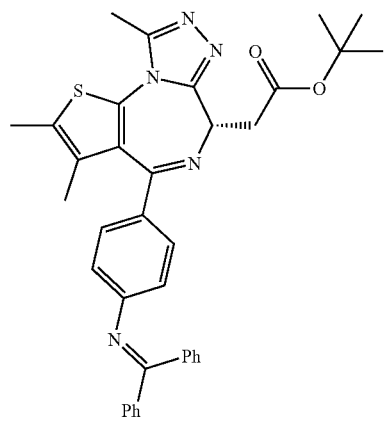

B.2

A mixture of Compound A (1.00 g, 0.44 mmol), Compound B.1 (0.600 g, 0.66 mmol), Pd$_2$(dba)$_3$ (0.20 g, 0.04 mmol), SPhos (0.09 g, 0.04 mmol), Cs$_2$CO$_3$ (2.1 g, 1.31 mmol) in toluene (10.0 mL) was stirred for 16 hours at 110° C. N$_2$. The solvent was concentrated under vacuum. The residue was purified by flash column chromatography (0-100% EtOAc in petroleum, Rf=0.5) to afford the desired product (Compound B.2)(1.3 g, 98.5%) as a yellow oil. LCMS (Method A): RT=0.875 min, m/z=602.3 [M+1]$^+$.

Step 2: tert-butyl (S)-2-(4-(4-aminophenyl)-2,3,9-trimethyl-6H-thieno[3,2-f][1,2,4]triazolo[4,3-a][1,4]diazepin-6-yl)acetate

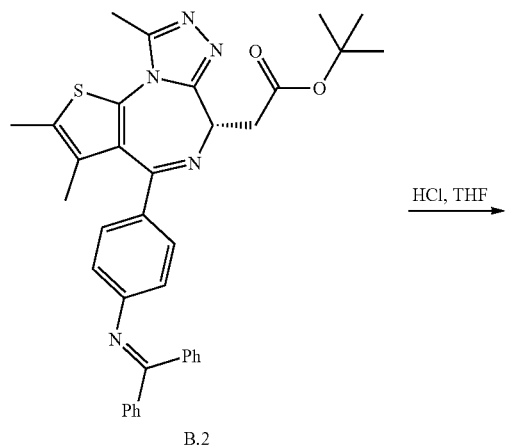

Step 3: tert-butyl (S)-2-(4-(4-iodophenyl)-2,3,9-trimethyl-6H-thieno[3,2-f][1,2,4]triazolo[4,3-a][1,4]diazepin-6-yl)acetate

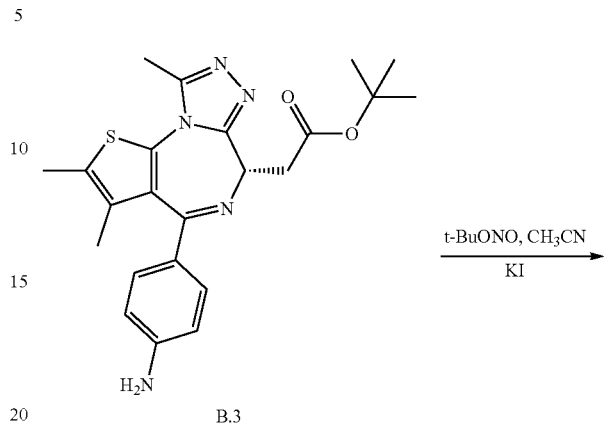

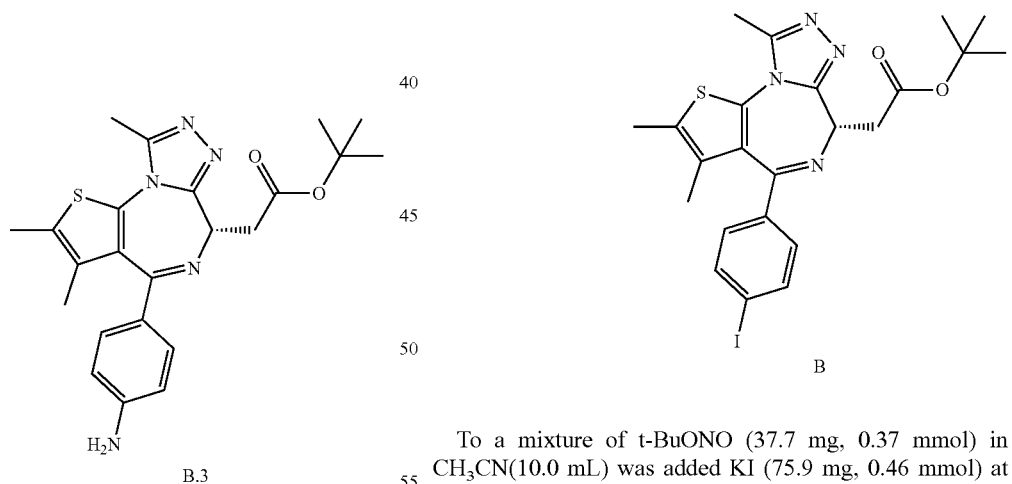

A mixture of Compound B.2 (1.30 g, 2.16 mmol) in THF (50.0 mL) and HCl (1.0 M, 26.0 mL) was stirred at 20° C. for 1 hour. Organic solvent was removed under vacuum and the aqueous solution was adjusted to pH=7.0 by saturated NaHCO$_3$ solution, and extracted with EtOAc (10.0 mL×4). The combined organic layer was dried over Na$_2$SO$_4$, filtered, concentrated, and purified by chromatography (0-5% MeOH in DCM) to afford the desired product (Compound B.3)(770.0 mg, 81.6%) as a yellow solid. LCMS (Method A): RT=0.595 min, m/z=438.2 [M+1]$^+$.

To a mixture of t-BuONO (37.7 mg, 0.37 mmol) in CH$_3$CN(10.0 mL) was added KI (75.9 mg, 0.46 mmol) at 20° C. The mixture was stirred at 65° C., and Compound B.3 (100.0 mg, 0.23 mmol) was added to the above mixture and the mixture was stirred at 65° C. for 18 hours. Another batch of t-BuONO (75.4 mg, 0.73 mmol) and KI (75.9 mg, 0.46 mmol) was added and stirred at 65° C. for another 2 hours. The reaction was quenched with water (15 mL), and the mixture was extracted with EtOAc (20 mL×3). The organic layer was washed with brine (10 mL×2), dried over Na$_2$SO$_4$, concentrated, and purified by prep-TLC(5% MeOH in DCM, Rf=0.5) to give desired product (Compound B)(103.2 mg, 82%) as a yellow solid. LCMS (Method A): RT=0.827 min, m/z=549.1 [M+1]$^+$.

Examples 1a and 1b tert-butyl 2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate (2 single stereoisomers)

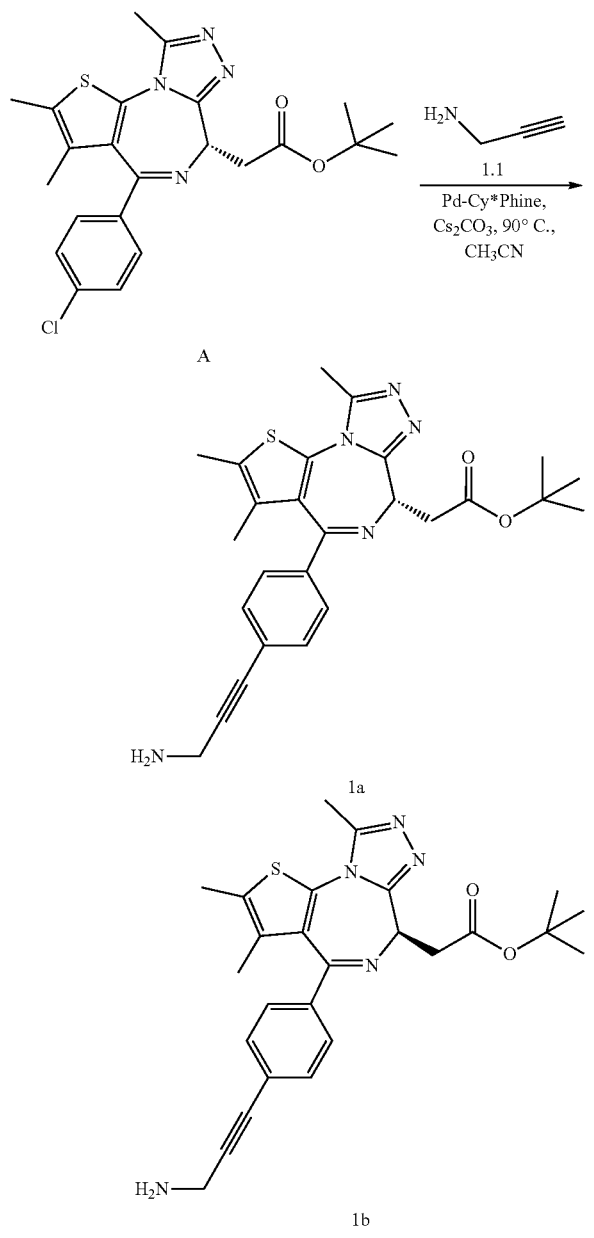

Example 2 tert-butyl (S)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate

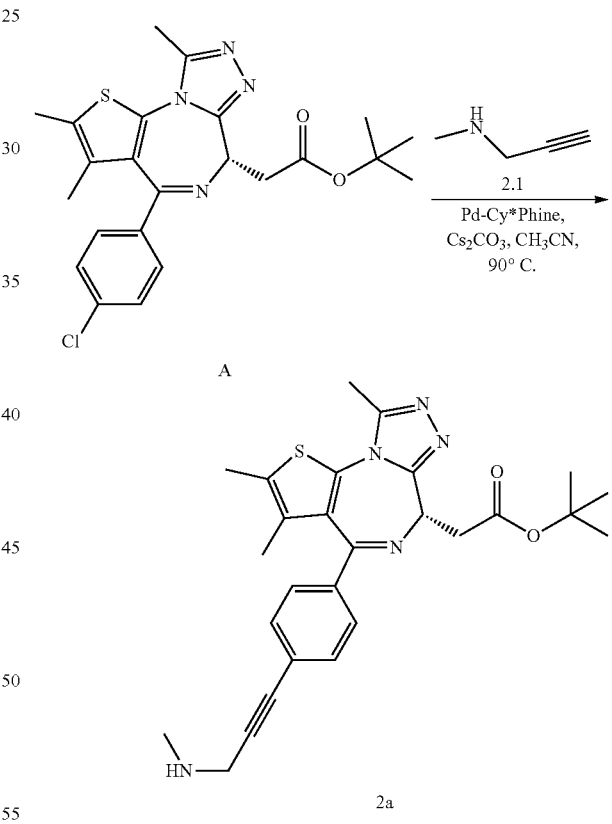

To a mixture of Compound A (1.200 g, 2.63 mmol) in acetonitrile (12 mL) was added Pd-Cy*Phine (similar transformations described in Eur. J Org. Chem., 2014, Vol. 32, pp. 7184-7192)(168.44 mg, 0.1300 mmol), Cs$_2$CO$_3$ (2.566 g, 7.88 mmol) and Compound 1.1 (723.17 mg, 13.13 mmol). The mixture was stirred at 90° C. in under microwave irradiation for 1 hour. The reaction mixture was filtered and purified by flash column chromatography (0-8% MeOH in DCM, Rf=0.3) to afford the racemic product, which were separated by prep-SFC (0.1% NH$_3$H$_2$O/EtOH, 40%) to give tert-butyl (R)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate (Compound 1b) (peak 1 on SFC, 89 mg, 7.1%) as a yellow solid and tert-butyl (S)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate (Compound 1a)(peak 2 on SFC, 350 mg, 27%) as a yellow solid.

Compound 1a: LCMS (Method A): RT=0.772 min, m/z=498.0 [M+23]+; 1H NMR (400 MHz, CDCl$_3$) δ 7.41 (s, 4H), 4.57 (t, J=7.6 Hz, 1H), 3.79 (s, 2H), 3.57-3.55 (m, 2H), 2.67 (s, 3H), 2.41 (s, 3H), 1.67 (s, 3H), 1.50 (s, 9H). SFC(Method 1, 2 uL) ee=99%, RT=7.088.

Compound 1b: LCMS (Method A): RT=0.773 min, m/z=498.1 [M+23]+; 1H NMR (400 MHz, CDCl3) δ 7.41 (s, 4H), 4.57 (t, J=7.6 Hz, 1H), 3.70 (s, 2H), 3.57-3.55 (m, 2H), 2.67 (s, 3H), 2.41 (s, 3H), 1.68 (s, 3H), 1.48 (s, 9H). SFC(Method 1, 2 uL) ee=91%, RT=5.304 min.

To a mixture of Compound A (30.0 mg, 0.0700 mmol) in acetonitrile (3.0 mL) was added Pd-Cy*Phine (4.21 mg, 0.0033 mmol), Cs$_2$CO$_3$ (64.17 mg, 0.200 mmol) and Compound 2.1 (22.68 mg, 0.330 mmol). The mixture was stirred at 90° C. under microwave irradiation for 1 hour. The reaction mixture was filtered and purified by prep-TLC(10% MeOH in DCM, Rf=0.5) to afford tert-butyl (S)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate (Compound 2a) (16.96 mg, 50%) as a yellow solid. LCMS (Method A): R$_T$=0.785 min, m/z=512.0 [M+23]$^+$; $^1$H NMR (400 MHz, CDCl$_3$) δ 7.42 (s, 4H), 4.57 (t, J=7.6 Hz, 1H), 3.70 (s, 2H), 3.57-3.55 (m, 2H), 2.68 (s, 3H), 2.60 (s, 3H), 2.41 (s, 3H), 1.68 (s, 3H), 1.51 (s, 9H).

Example 3 tert-butyl (S)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate

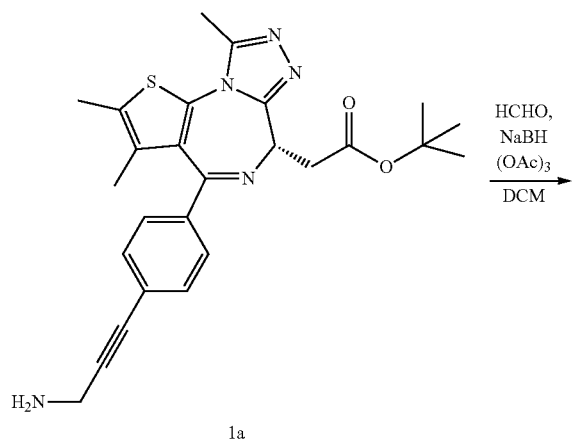

To a stirred solution of Compound 1a (25.0 mg, 0.0500 mmol) in MeOH (0.5000 mL) and DCM (4.0 mL) was added 37% HCHO (1.0 mL) and HOAc (1 drops, cat.). After it was stirred for 10 minutes, NaBH(OAc)$_3$ (111.4 mg, 0.530 mmol) was added, and the mixture was stirred at 20° C. for 1 hour. The mixture was concentrated and purified by prep-HPLC (ACN 18-48/0.225% FA in water) to give tert-butyl (S)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate (Compound 3a)(16.98 mg, 64.1%) as a white solid. LCMS (Method A): RT=0.735 min, m/z=504.1 [M+1]$^+$; $^1$H NMR (400 MHz, CDCl$_3$) δ 7.42 (s, 4H), 4.57 (t, J=7.2 Hz, 1H), 3.57-3.55 (m, 2H), 3.51 (s, 2H), 2.68 (s, 3H), 2.40 (s, 9H), 1.68 (s, 3H), 1.51 (s, 9H).

Example 4 tert-butyl (S)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate

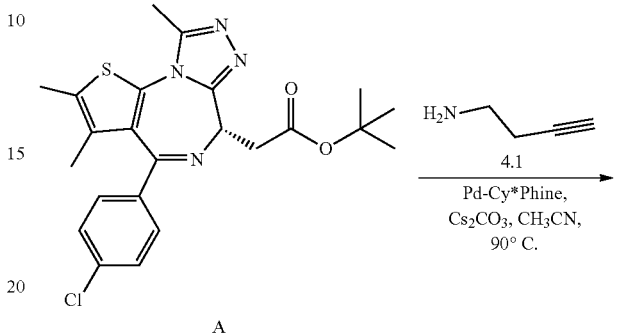

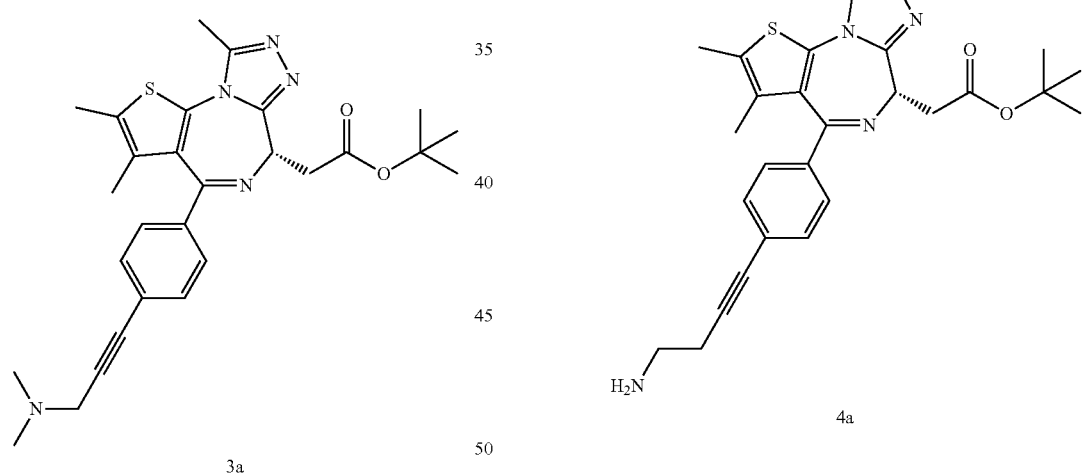

To a mixture of Compound A (80.0 mg, 0.180 mmol) in acetonitrile (3.0 mL) was added Pd-Cy*Phine (11.23 mg, 0.0100 mmol), Cs$_2$CO$_3$ (171.11 mg, 0.530 mmol) and Compound 4.1 (60.49 mg, 0.880 mmol). The mixture was stirred at 90° C. under microwave irradiation for 2 hours. The reaction mixture was concentrated in vacuo and purified by prep-TLC(20% MeOH in DCM, Rf=0.5) and prep-HPLC (acetonitrile 23-53%/0.225% FA in water) to afford tert-butyl (S)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate (Compound 4a)(8.45 mg, 10% yield) as a white solid. LCMS (Method A): RT=0.651 min, m/z=490.0 [M+1]+; $^1$H NMR (400 MHz, CDCl$_3$) δ 7.37 (brs, 4H), 4.55-4.52 (m, 1H), 3.57-3.46 (m, 3H), 3.03 (brs, 3H), 2.69 (brs, 2H), 2.64 (s, 3H), 2.37 (s, 3H), 1.64 (s, 3H), 1.47 (s, 9H).

Example 5 tert-butyl (S)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate

Example 6 tert-butyl (S,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate

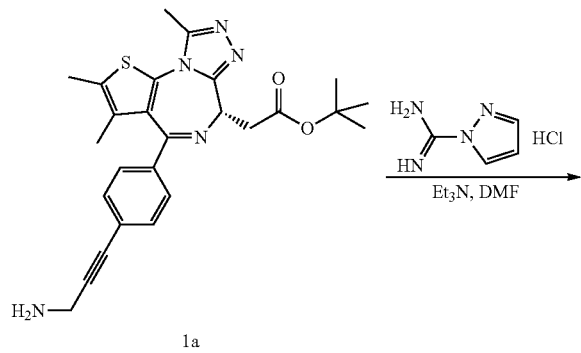

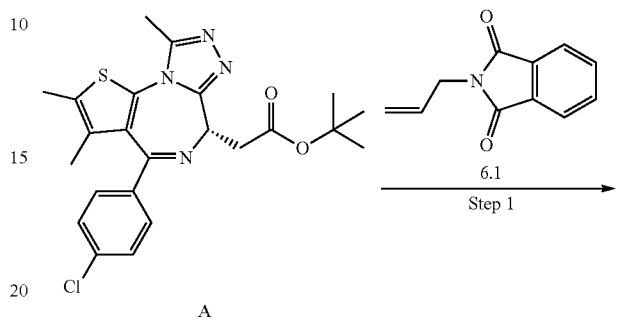

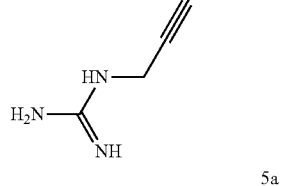

5a

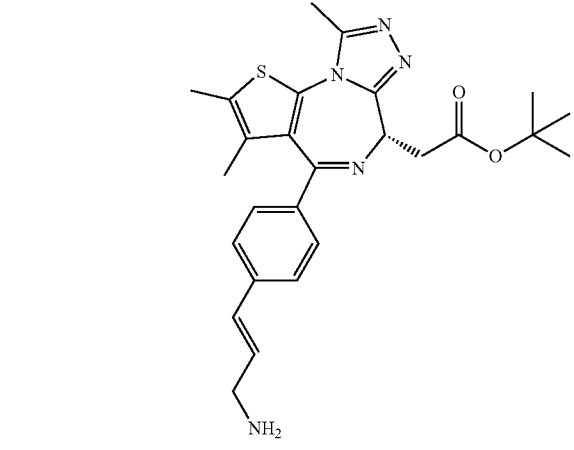

To a solution of Compound 1a (25.0 mg, 0.0500 mmol) and 1H-pyrazole-1-carboximidamide hydrochloride (11.56 mg, 0.080 mmol) in DMF (1.0 mL) was added DIEA (20.38 mg, 0.160 mmol) at 25° C. The reaction mixture was stirred at 25° C. for 12 hours. The reaction mixture was filtered and the resulting residue was purified by prep-HPLC(acetonitrile 27-47/0.225% FA in water) to afford tert-butyl (S)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate (Compound 5a) (5 mg, 18%) as a white solid. LCMS (Method A): $R_T$=0.750 min, m/z=518.5 [M+1]$^+$.

Step 1: Compound 6.2

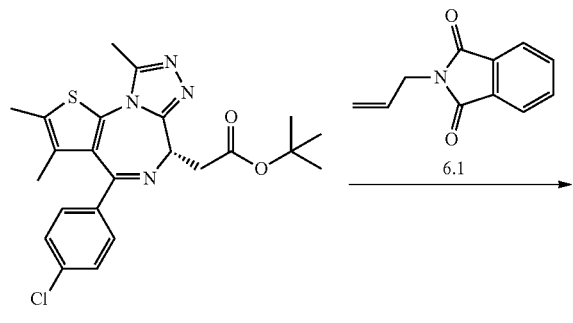

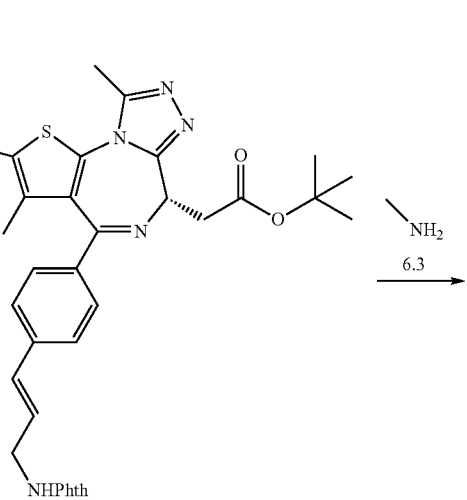

Step 2: tert-butyl (S,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate

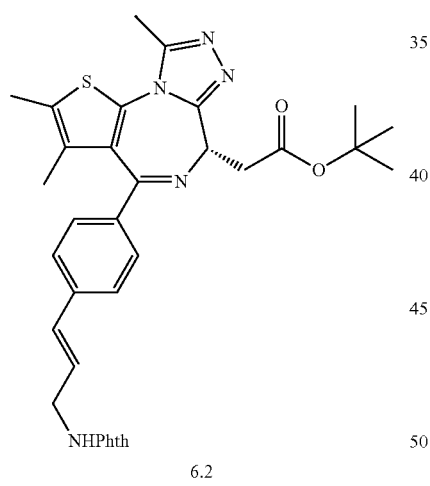

6.2

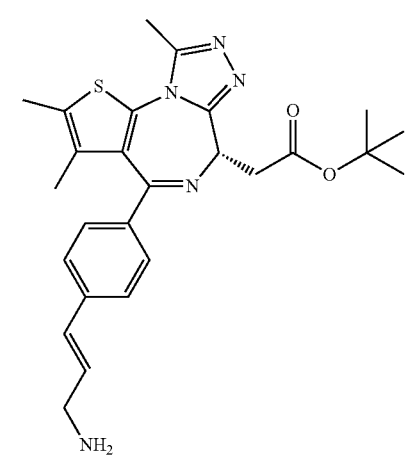

6a

To a solution of Pd$_2$(dba)$_3$ (12.0 mg, 0.01 mmol) in NMP (3.0 mL) was added Compound A (30.0 mg, 0.07 mmol), [t-Bu$_3$PH]$^+$BF$_4^-$ (38.5 mg, 0.20 mmol), Compound 6.1 (36.9 mg, 0.20 mmol) and Cy$_2$NMe (15.2 mg, 0.05 mmol). The mixture was stirred at 160° C. for 20 minutes under microwave irradiation. Then the mixture was filtered, concentrated, and diluted with water (10.0 mL). The resulting solution was extracted with EtOAc (10 mL×3) and the combined organic layer was dried over anhydrous Na$_2$SO$_4$ and concentrated. The residue was purified by column chromatography (0-50% EtOAc in PE, Rf=0.5) to afford the desired product (Compound 6.2)(43.0 mg, 99.2%) as a red solid. LCMS (Method A): RT=0.804 min, m/z 608.3 [M+1]$^+$.

A solution of Compound 6.2 (31 mg, 0.06 mmol) in CH$_3$NH$_2$/THF (2.0 mol/L, 10 mL) was stirred for 16 hours at 80° C. The mixture was concentrated, and purified by prep-HPLC (CN$_3$CN 20-50/0.1% FA in water) to afford the desired product tert-butyl (S,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate (Compound 6a)(6.6 mg, 27%) as a white solid. LCMS (10-80, AB, 7.0 min): RT=2.630 min, m/z 478.1 [M+H]$^+$; $^1$H NMR (400 MHz, CDCl$_3$): δ 7.41-7.33 (m, 4H), 6.59-6.55 (m, 1H), 6.33 (brs, 1H), 4.57-4.54 (t, J=7.2 Hz, 1H), 3.55-3.54 (m, 4 H), 2.66 (s, 3H), 2.40 (s, 3H), 1.67 (s, 3H), 1.48 (s, 9H). SFC(OJ-H_1_5_40_2.5 ML_10 MIN): RT=3.385 min, ee=89.8%.

Example 7 tert-butyl (S)-2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate

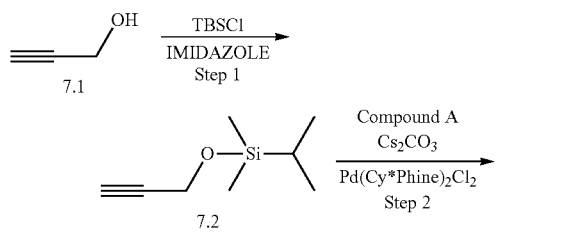

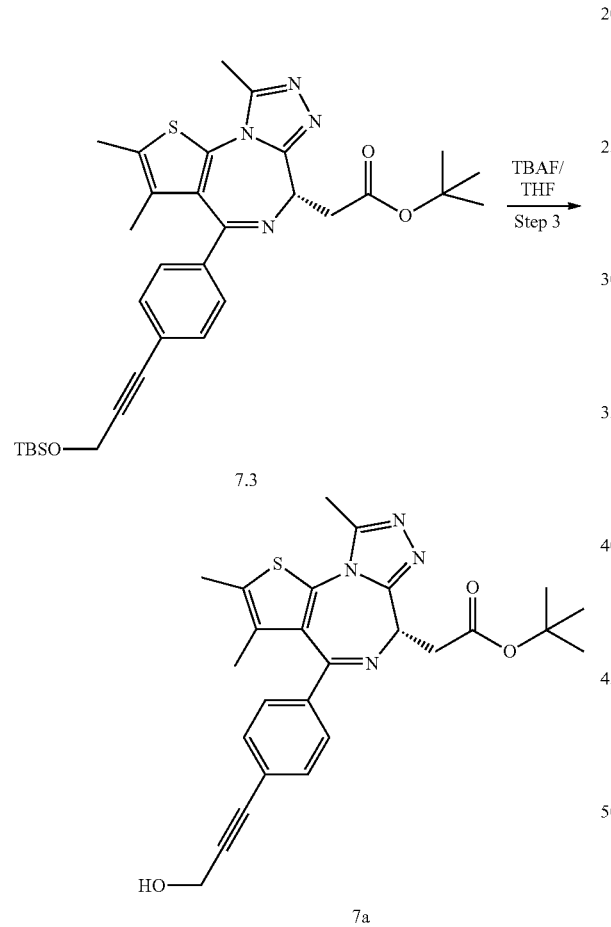

A mixture of Compound 7.1 (1.2 g, 21.41 mmol), TBSCl (4.84 g, 32.11 mmol) and imidazole (4.37 g, 64.22 mmol) in DCM (15 mL) was stirred at 25° C. for 12 hours. The mixture was quenched with water (20 mL) and the mixture was extracted with EtOAc (20 mL×3). The organic layer was washed with brine (30 mL×2), concentrated and purified by column chromatography (0-5% EtOAc in petroleum ether, Rf=0.7) to give Compound 7.2 (2.00 g, 55%) as a light yellow oil. $^1$H NMR (400 MHz, CDCl$_3$) δ 4.9 (d, J=3.6 Hz, 2H), 0.90 (s, 9H), 0.10 (m, 6H).

Step 2: tert-butyl (S)-2-(4-(4-(3-((tert-butyldimethylsilyl)oxy)prop-1-yn-1-yl)phenyl)-2,3,9-trimethyl-6H-thieno[3,2-f][1,2,4]triazolo[4,3-a][1,4]diazepin-6-yl)acetate

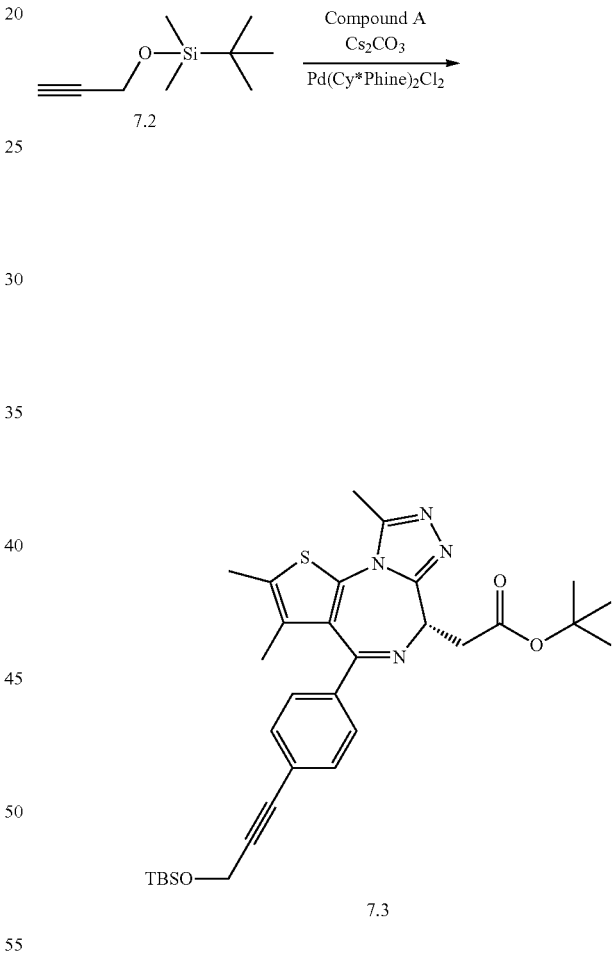

Step 1: tert-butyldimethyl(prop-2-yn-1-yloxy)silane

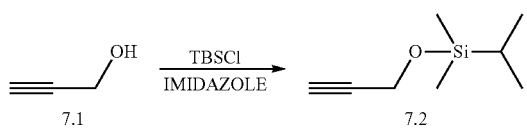

To a solution of Compound A (300.0 mg, 0.6600 mmol) in acetonitrile (4.0 mL was added Cs$_2$CO$_3$ (641.67 mg, 1.97 mmol), Compound 7.2 (559.05 mg, 3.28 mmol) and Pd(Cy*Phine)$_2$Cl$_2$ (42.11 mg, 0.0300 mmol), and the mixture was stirred at 100° C. under N$_2$ for 1.5 hours. The reaction mixture was filtered, water (10 mL) was added, and extracted with EtOAc (10 mL×2). The organic layers were concentrated and purified by column chromatography (0-10% MeOH in DCM, Rf=0.5) to afford Compound 7.3 (270 mg, 70%) as a yellow solid. LCMS (Method A): R$_T$=1.187 min, m/z=591.3[M+1]$^+$.

Step 3: tert-butyl (S)-2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate

Example 8 tert-butyl (S)-2-(4-(4-(3-(hydroxyamino)prop-1-yn-1-yl)phenyl)-2,3,9-trimethyl-6H-thieno[3,2-f][1,2,4]triazolo[4,3-a][1,4]diazepin-6-yl)acetate

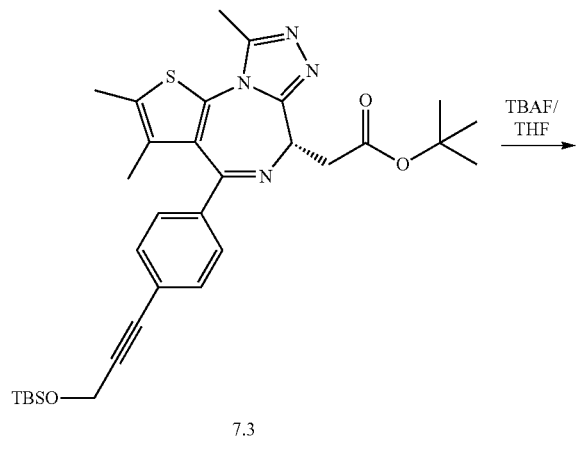

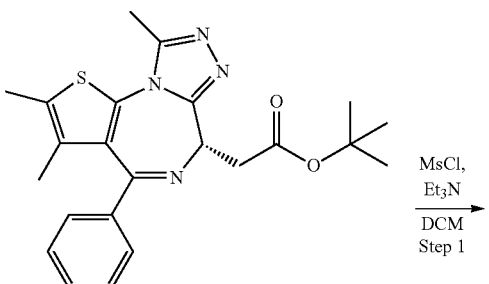

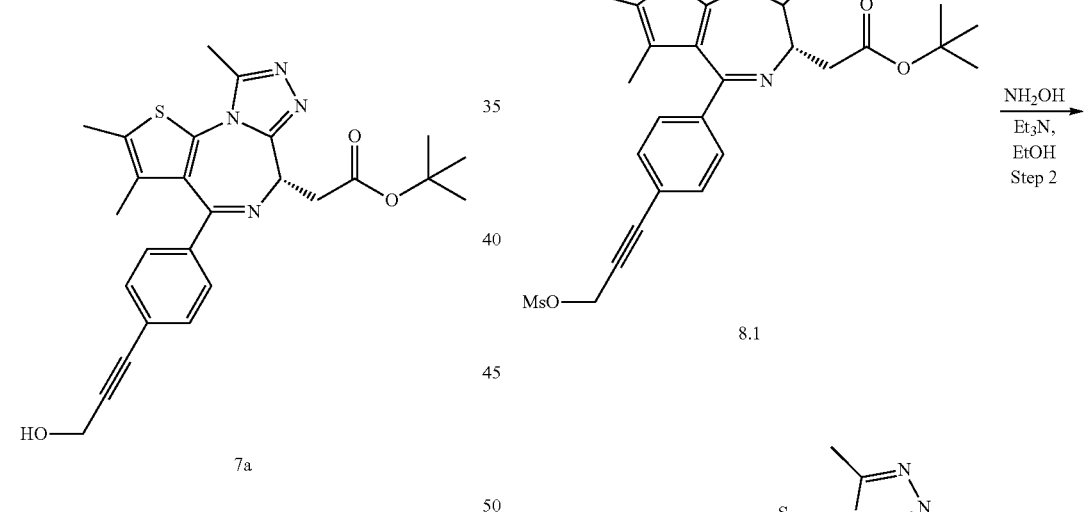

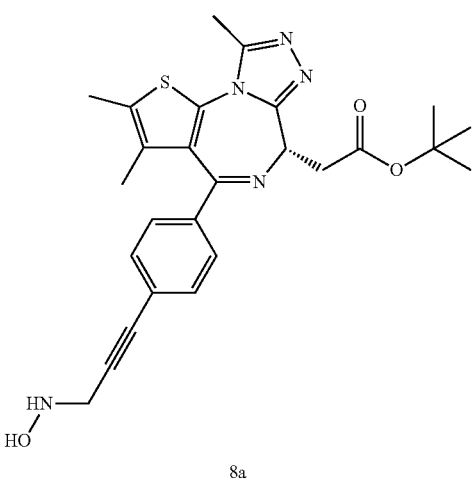

To a solution of Compound 7.3 (270.0 mg, 0.460 mmol) in THF (3.0 mL) was added a solution of TBAF in THF (2.28 mL, 2.28 mmol). The mixture was stirred at 25° C. for 2 hours. The mixture was concentrated and dissolved EtOAc (20 mL), and washed with water (10 mL×3). The organic layer was dried over anhydrous sodium sulfate, concentrated, and purified by prep-HPLC(acetonitrile 47-67/0.225% FA in water) to give the desired product tert-butyl (S)-2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate (Compound 7a)(100 mg, 46%) as a white solid. LCMS (Method A): RT=0.881 min, m/z=477.2 [M+H]+; $^1$H NMR (400 MHz, DMSO-d6): δ 7.47 (d, J=8.4 Hz, 2H), 7.41 (d, J=8.4 Hz, 2H), 5.37 (t, J=5.6 Hz, 1H), 4.44-4.40 (m, 1H), 4.30 (d, J=5.6 Hz, 2H), 3.30-3.26 (m, 2H), 2.60 (s, 3H), 2.42 (s, 3H), 1.63 (s, 3H), 1.42 (s, 9H).

157

Step 1: tert-butyl (S)-2-(2,3,9-trimethyl-4-(4-(3-((methylsulfonyl)oxy)prop-1-yn-1-yl)phenyl)-6H-thieno[3,2-f][1,2,4]triazolo[4,3-a][1,4]diazepin-6-yl)acetate

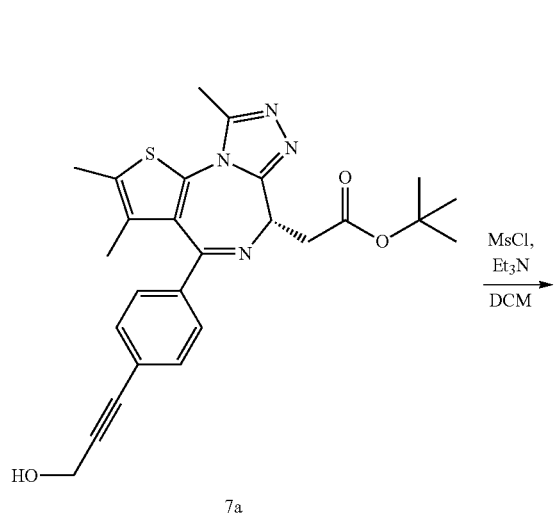

7a

To a mixture of Compound 7a (140.0 mg, 0.2900 mmol) in DCM (10 mL) was added Et₃N(148.62 mg, 1.47 mmol) and MsCl (310.0 mg, 2.71 mmol). After the mixture was stirred at 25° C. for 1 hour, it was diluted with DCM (30 mL) and washed with water (10 mL×3). The organic layer was dried over anhydrous sodium sulfate, and concentrated to give Compound 8.1 (160 mg, 98%) as yellow oil, which was used in next step directly. LCMS (Method A): RT=0.935 min, m/z=555.1 [M+1]⁺.

158

Step 2: tert-butyl (S)-2-(4-(4-(3-(hydroxyamino)prop-1-yn-1-yl)phenyl)-2,3,9-trimethyl-6H-thieno[3,2-f][1,2,4]triazolo[4,3-a][1,4]diazepin-6-yl)acetate

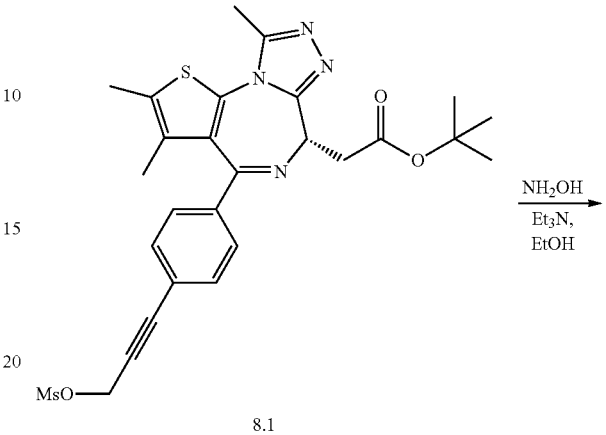

8.1

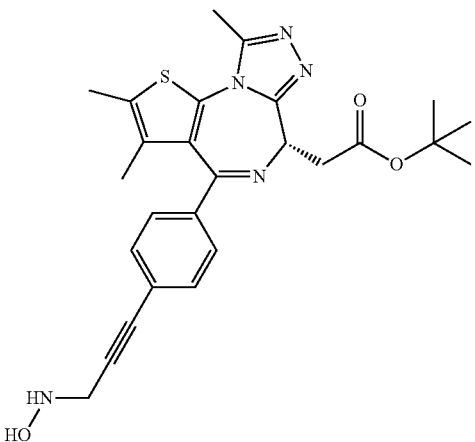

8a

To a mixture of Compound 8.1 (160.0 mg, 0.290 mmol) in EtOH (10 mL) was added hydroxylamine (40.09 mg, 0.580 mmol) and Et₃N(87.57 mg, 0.870 mmol). The mixture was stirred at 90° C. for 1 hour. The mixture was concentrated and diluted with EtOAc (30 mL) and washed water (10 mL). The organic layer was concentrated and purified by prep-HPLC (acetonitrile 0-40/0.1% HCl in water) to afford the desired product tert-butyl (S)-2-(4-(4-(3-(hydroxyamino)prop-1-yn-1-yl)phenyl)-2,3,9-trimethyl-6H-thieno[3,2-f][1,2,4]triazolo[4,3-a][1,4]diazepin-6-yl)acetate (Compound 8a)(6.37 mg, 4%) as a white solid. LCMS (Method A):R$_T$=0.809 min, m/z=492.3 [M+H]⁺; ¹H NMR (400 MHz, CDCl₃) δ 7.45 (d, J=8.0 Hz, 2H), 7.41 (d, J=8.0 Hz, 2H), 5.25-4.71 (br, 2H), 4.62 (t, J=7.6 Hz, 1H), 4.26 (s, 2H), 3.60-3.54 (m, 2H), 2.71 (s, 3H), 2.44 (s, 3H), 1.67 (s, 3H), 1.48 (s, 9H).

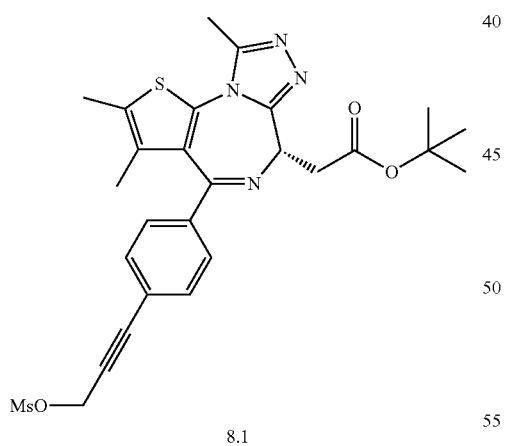

8.1

Example 9 tert-butyl (S)-2-(4-(4-(3-aminopropyl)phenyl)-2,3,9-trimethyl-6H-thieno[3,2-f][1,2,4]triazolo[4,3-a][1,4]diazepin-6-yl)acetate

Example 10 tert-butyl (S)-2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate

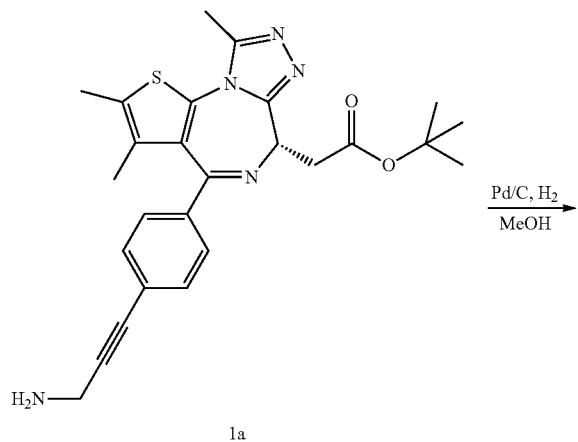

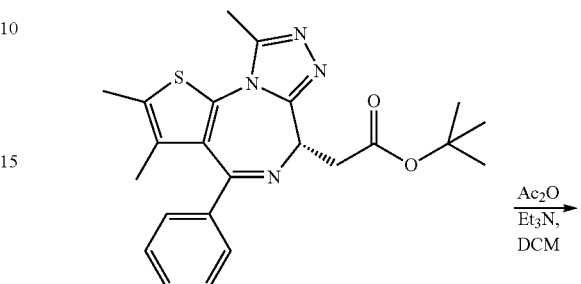

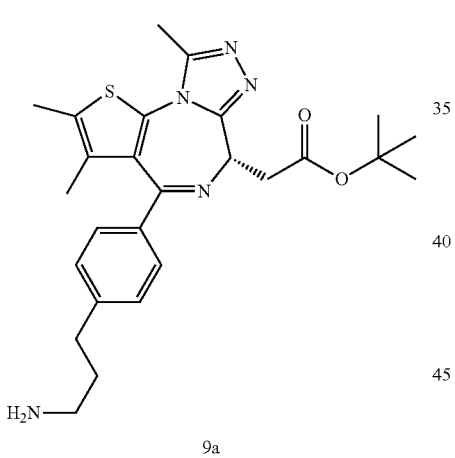

9a

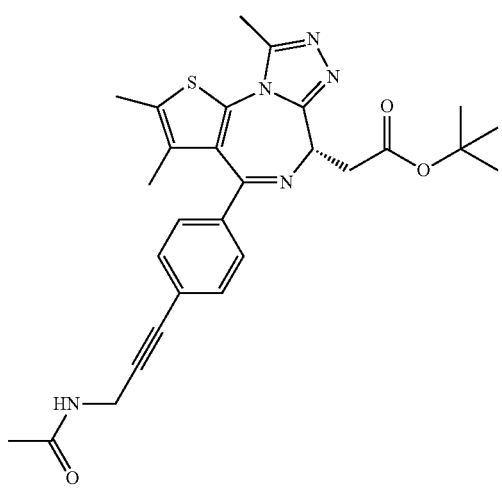

10a

To solution of Compound 1a (100.0 mg, 0.2100 mmol) in anhydrous MeOH (6.0 mL) was added 10% Pd/C(112 mg). The reaction mixture was stirred at 20° C. under $H_2$ atmosphere for 0.5 hours. The catalyst was filtered and the filtrate was concentrated in vacuo. The residue was separated by SFC(Supercritical $CO_2$/EtOH-0.1% $NH_3H_2O$=30%; 60 mL/min), and then purified by prep-HPLC(Xtimate C18 150*25 mm*5 um, acetonitrile 20-50/0.225% FA in water) to afford tert-butyl (S)-2-(4-(4-(3-aminopropyl)phenyl)-2,3,9-trimethyl-6H-thieno[3,2-f][1,2,4]triazolo[4,3-a][1,4]diazepin-6-yl)acetate (Compound 9a)(27 mg, 24%) as a white solid. LCMS (Method A): RT=0.897 min, m/z=480.5 [M+1]+; 1H NMR (400 MHz, CDCl3) δ 8.39 (brs, 1H), 7.35 (d, J=7.6 Hz, 2H), 7.13 (d, J=8.0 Hz, 2H), 6.79 (brs, 3H), 4.56-4.52 (m, 1H), 3.57-3.46 (m, 2H), 2.76 (brs, 2H), 2.67-2.63 (m, 5H), 2.39 (s, 3H), 1.90 (brs, 2H), 1.65 (s, 3H), 1.48 (s, 9H).

A solution of Compound 1a (15.0 mg, 0.0300 mmol) in DCM (6.0 mL) was added $Ac_2O$ (9.66 mg, 0.0900 mmol) and $Et_3N$(9.57 mg, 0.0900 mmol). The mixture was stirred at 25° C. for 2 hours. The reaction mixture was concentrated and purified by prep-TLC (10% MeOH in DCM, Rf=0.6) to give tert-butyl (S)-2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate (Compound 10a)(12.63 mg, 77%) as a white solid. LCMS (Method A): RT=0.805 min, m/z=518.1 [M+1]+; 1H NMR (400 MHz, CDCl3) δ 7.41 (s, 4H), 5.75 (brs, 1H), 4.57 (t, J=7.2 Hz, 1H), 4.30-4.28 (m, 2H), 3.57-3.55 (m, 2H), 2.68 (s, 3H), 2.41 (s, 3H), 2.04 (s, 3H), 1.51 (s, 9H). SFC(OD_ETOH (DEA)_5_40_2.8 ML_8 MIN) ee=95%, $R_T$=3.642 min.

Example 11 tert-butyl 2-((6S)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate

Example 12 tert-butyl (S)-2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate

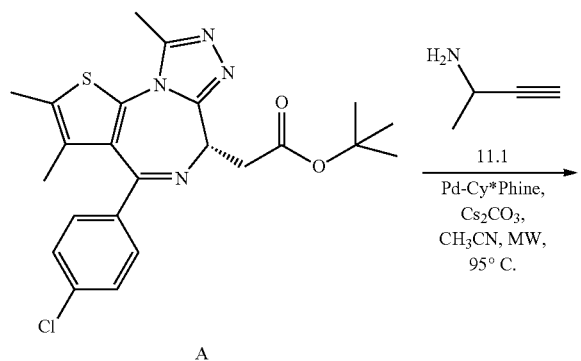

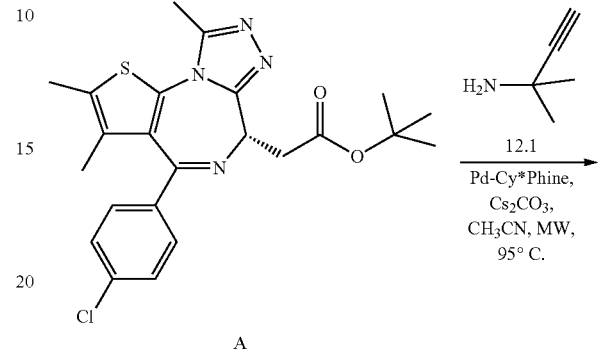

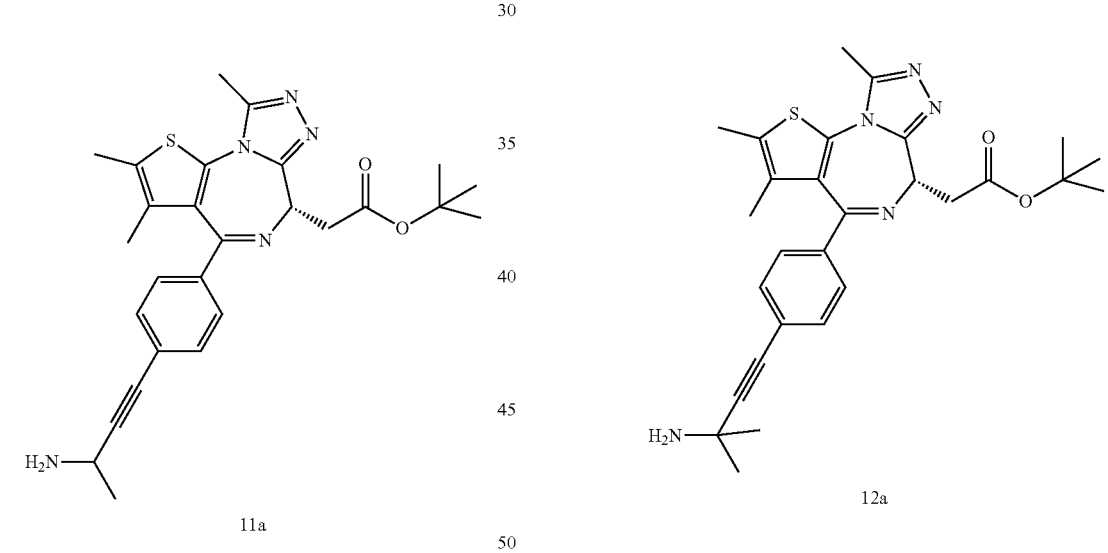

To a mixture of Compound A (30.0 mg, 0.0700 mmol) in acetonitrile (2.0 mL) was added Pd-Cy*Phine (4.21 mg, 0.0033 mmol), $Cs_2CO_3$ (64.17 mg, 0.2000 mmol) and Compound 11.1 (22.68 mg, 0.3300 mmol). The mixture was stirred at 95° C. under microwave irradiation for 1.5 hours. The reaction mixture was filtered and purified by prep-TLC (5% methanol in DCM, Rf=0.5) and prep-HPLC(acetonitrile 22-52/0.225% FA in water) to afford tert-butyl 2-((6S)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate (Compound 11a)(10.3 mg, 32%) as a white solid. LCMS (Method A): RT=0.666 min, m/z=490.1 [M+1]$^+$; 1H NMR (400 MHz, CDCl$_3$) δ 7.42-7.38 (m, 4H), 4.57 (t, J=7.6 Hz, 1H), 4.00-3.95 (m, 1H), 3.57-3.54 (m, 2H), 2.68 (s, 3H), 2.41 (s, 3H), 1.67 (s, 3H), 1.53-1.46 (m, 12H).

To a mixture of Compound A (30.0 mg, 0.0700 mmol) in acetonitrile (2.0 mL) was added Pd-Cy*Phine (4.21 mg, 0.0033 mmol), $Cs_2CO_3$ (64.17 mg, 0.200 mmol) and Compound 12.1 (27.29 mg, 0.3300 mmol). The mixture was stirred at 95° C. under microwave irradiation for 1.5 hours. The reaction mixture was filtered and purified by prep-TLC (5% MeOH in DCM, Rf=0.5) and prep-HPLC(acetonitrile 22-52/0.225% FA in water) to afford tert-butyl (S)-2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate (Compound 12a)(13.77 mg, 38%) as a white solid. LCMS (Method A): RT=0.662 min, m/z=504.2 [M+1]$^+$; 1H NMR (400 MHz, CDCl$_3$) δ 7.42-7.37 (m, 4H), 4.57 (t, J=7.6 Hz, 1H), 3.57-3.55 (m, 2H), 2.68 (s, 3H), 2.41 (s, 3H), 1.67 (s, 3H), 1.53-1.55 (m, 15H). SFC(AS_1_5_40_2.8 ML_8 MIN): RT=2.772 min, ee=98%.

Example 13 tert-butyl (S)-2-(4-(4-(but-1-yn-1-yl)phenyl)-2,3,9-trimethyl-6H-thieno[3,2-f][1,2,4]triazolo[4,3-a][1,4]diazepin-6-yl)acetate

Example 14 tert-butyl (S)-2-(2,3,9-trimethyl-4-(4-(prop-1-yn-1-yl)phenyl)-6H-thieno[3,2-f][1,2,4]triazolo[4,3-a][1,4]diazepin-6-yl)acetate

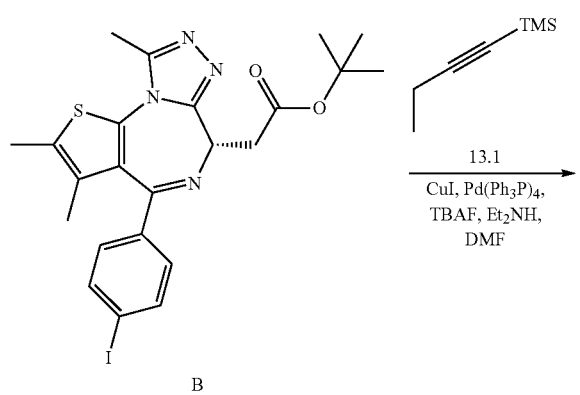

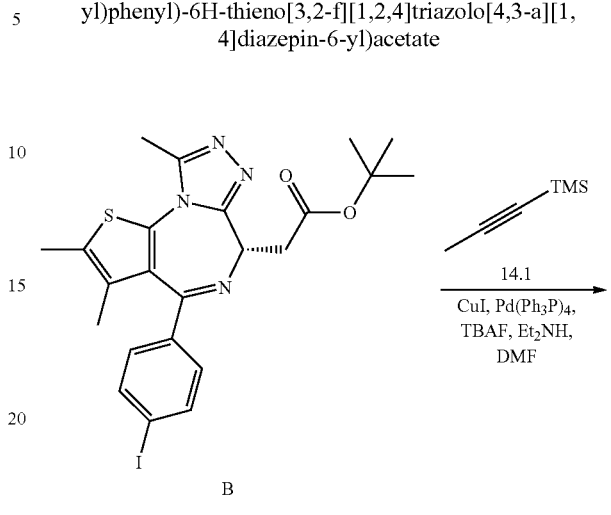

To a solution of Et$_2$NH(106.7 mg, 1.46 mmol), CuI (1.4 mg, 0.01 mmol) and Compound B (40.0 mg, 0.07 mmol) in THF (10 mL) was added Pd(Ph$_3$P)$_4$ (8.43 mg, 0.01 mmol) and TBAF (0.26 mL, 0.26 mmol), Compound 13.1 (27.6 mg, 0.22 mmol) at 25° C. The mixture was stirred for 12 hours under N$_2$. The reaction was concentrated and purified by prep-HPLC (CH$_3$CN 70-100/0.1% FA in water) to afford the desired product tert-butyl (S)-2-(4-(4-(but-1-yn-1-yl)phenyl)-2,3,9-trimethyl-6H-thieno[3,2-f][1,2,4]triazolo[4,3-a][1,4]diazepin-6-yl)acetate (Compound 13a)(6.9 mg, 20%) as a yellow solid. LCMS (10-80, AB, 7.0 min): RT=4.935 min, m/z=475.0 [M+1]$^+$; $^1$H NMR (400 MHz, CDCl$_3$): (7.38 (s, 4H), 4.56 (t, J=7.2 Hz, 1H), 3.60-3.50 (m, 2H), 2.68 (s, 3H), 2.46-2.41 (m, 5H), 1.67 (s, 3H), 1.50 (s, 9H), 1.24-1.22 (m, 3H). SFC(AD_50 MM_ETOH (DEA)_5_40_2.5 ML): RT=4.614 min, ee=98.9%.

To a solution of Et$_2$NH(106.7 mg, 1.46 mmol), CuI (1.4 mg, 0.01 mmol) and Compound B (40.0 mg, 0.07 mmol) in THF (10 mL) was added Pd(Ph$_3$P)$_4$ (8.4 mg, 0.01 mmol), TBAF (0.26 mL, 0.26 mmol) and Compound 14.1 (24.6 mg, 0.22 mmol) at 25° C. The mixture was stirred for 16 hours under N$_2$. The reaction mixture was concentrated and purified by prep-HPLC (CH$_3$CN 65-95/0.1% FA in water) to afford the desired product tert-butyl (S)-2-(2,3,9-trimethyl-4-(4-(prop-1-yn-1-yl)phenyl)-6H-thieno[3,2-f][1,2,4]triazolo[4,3-a][1,4]diazepin-6-yl)acetate (Compound 14a)(8.0 mg, 24%) as a yellow solid. LCMS (10-80, AB, 7.0 min): RT=4.595 min, m/z=461.0 [M+H]$^+$. $^1$H NMR (400 MHz, CDCl$_3$) δ 7.43-7.34 (m, 4H), 4.57 (t, J=6.4 Hz, 1H), 3.56-3.50 (m, 2H), 2.68 (s, 3H), 2.41 (s, 3H), 2.07 (s, 3H), 1.68 (s, 3H), 1.50 (s, 9H). SFC(AD_50 MM_ETOH (DEA)_5_40_2.5 ML): RT=1.566 min, ee=98.4%.

Example 15
methyl 4-(5-(3-aminoprop-1-yn-1-yl)-3-fluoropyridin-2-yl)-10-methyl-7-((methylsulfonyl)methyl)-11-oxo-3,4,10,11-tetrahydro-1H-1,4,10-triazadibenzo[cd,f]azulene-6-carboxylate (Compound 15)
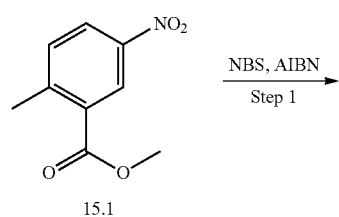
15.1
NBS, AIBN
Step 1
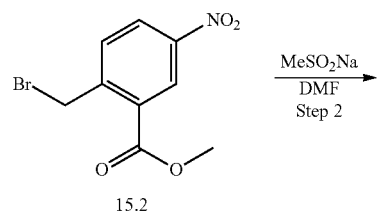
15.2
MeSO₂Na
DMF
Step 2
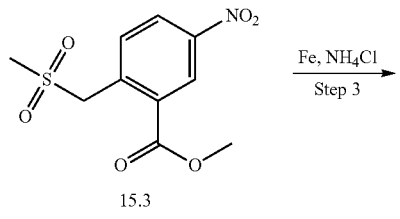
15.3
Fe, NH₄Cl
Step 3
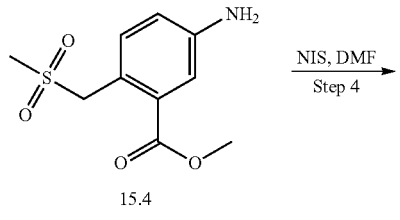
15.4
NIS, DMF
Step 4
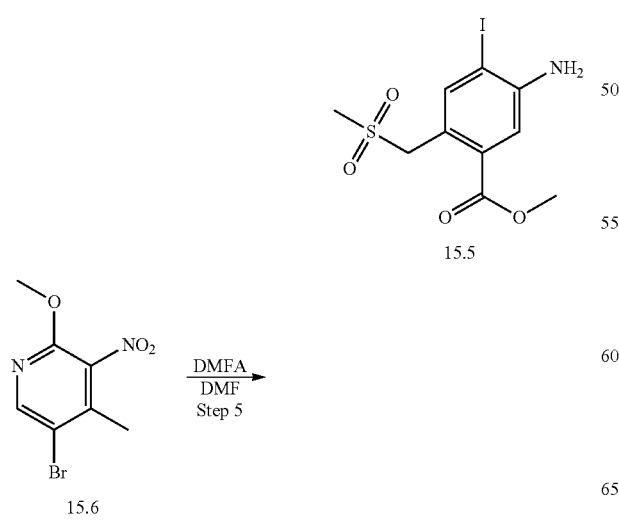
15.5
15.6
DMFA
DMF
Step 5
-continued
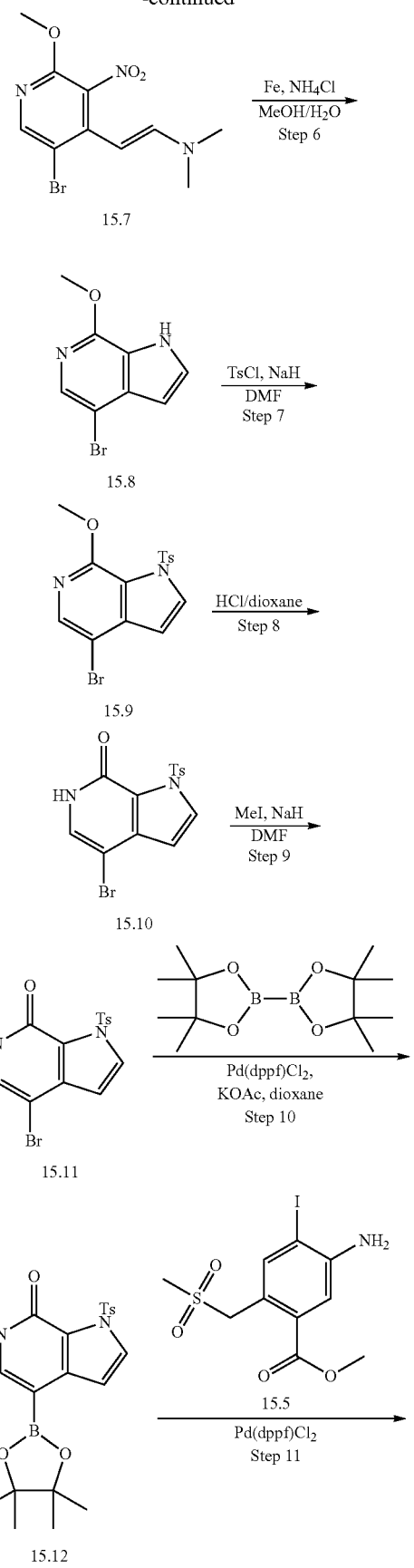
15.7
Fe, NH₄Cl
MeOH/H₂O
Step 6
15.8
TsCl, NaH
DMF
Step 7
15.9
HCl/dioxane
Step 8
15.10
MeI, NaH
DMF
Step 9
15.11
Pd(dppf)Cl₂, KOAc, dioxane
Step 10
15.12
15.5
Pd(dppf)Cl₂
Step 11

167
-continued

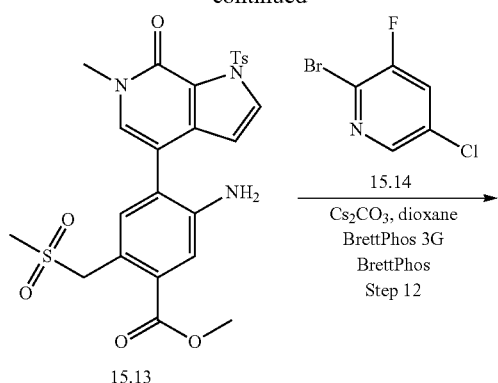

168
-continued

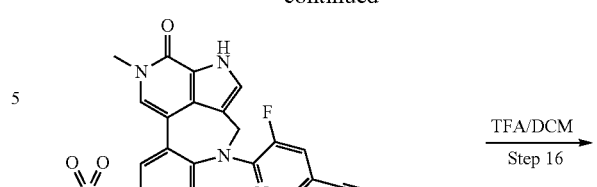

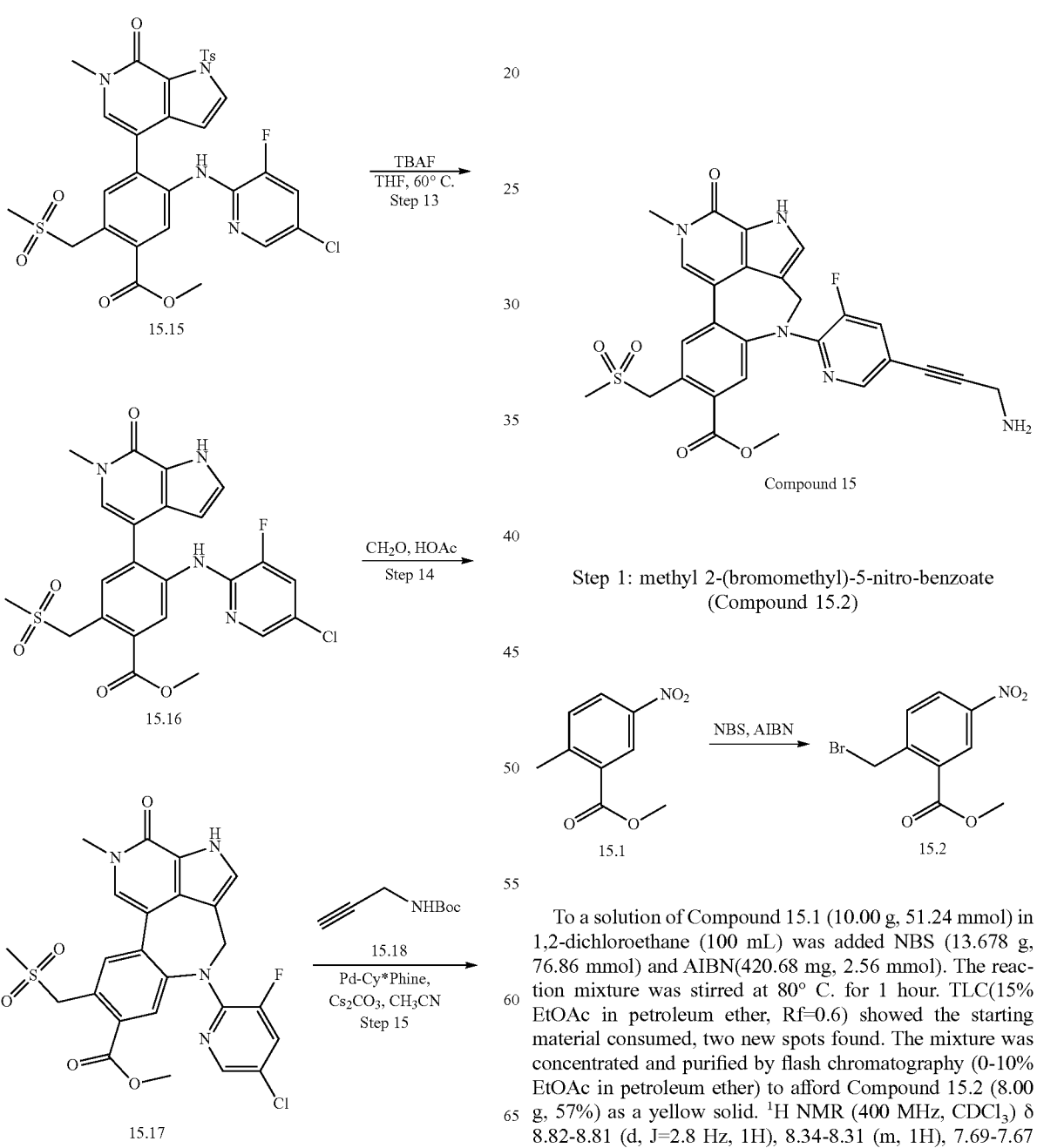

Step 1: methyl 2-(bromomethyl)-5-nitro-benzoate (Compound 15.2)

To a solution of Compound 15.1 (10.00 g, 51.24 mmol) in 1,2-dichloroethane (100 mL) was added NBS (13.678 g, 76.86 mmol) and AIBN(420.68 mg, 2.56 mmol). The reaction mixture was stirred at 80° C. for 1 hour. TLC(15% EtOAc in petroleum ether, Rf=0.6) showed the starting material consumed, two new spots found. The mixture was concentrated and purified by flash chromatography (0-10% EtOAc in petroleum ether) to afford Compound 15.2 (8.00 g, 57%) as a yellow solid. $^1$H NMR (400 MHz, CDCl$_3$) δ 8.82-8.81 (d, J=2.8 Hz, 1H), 8.34-8.31 (m, 1H), 7.69-7.67 (d, J=8.4 Hz, 1H), 4.99 (s, 2H), 4.00 (s, 3H).

Step 2: methyl 2-(methylsulfonylmethyl)-5-nitro-benzoate (Compound 15.3)

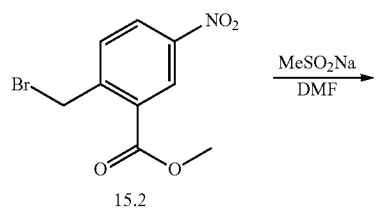

To a solution of Compound 15.2 (8.00 g, 29.19 mmol) in DMF (150 mL) was added MeSO$_2$Na (14.899 g, 145.95 mmol). The mixture was stirred at 60° C. for 1 hour. TLC (15% EtOAc in petroleum ether, Rf=0.5) showed the starting material consumed, two new spots was found. The mixture was quenched with water (100 mL), extracted with EtOAc (100 mL×2). The organic layer was washed with water (100 mL×3) and brine (100 mL×3), dried over Na$_2$SO$_4$, concentrated and purified by flash column chromatography (0-35% EtOAc in petroleum ether) to afford Compound 15.3 (7.500 g, 94%) as a yellow solid. $^1$H NMR (400 MHz, CDCl$_3$) δ 8.88 (d, J=2.8 Hz, 1H), 8.42-8.39 (m, 1H), 7.78-7.76 (d, J=8.4 Hz, 1H), 5.03 (s, 2H), 4.00 (s, 3H), 2.91 (s, 3H).

Step 3: methyl 5-amino-2-(methylsulfonylmethyl)benzoate (Compound 15.4)

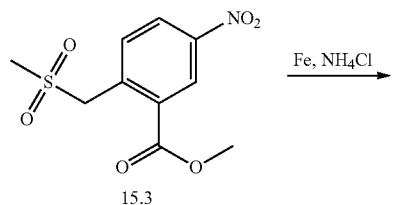

To a solution of Compound 15.3 (7.500 g, 27.45 mmol) in MeOH (150 mL) and water (20 mL) was added iron (7.664 g, 137.23 mmol) and NH$_4$C$_1$(7.340 g, 137.23 mmol), and the mixture was stirred at 75° C. for 16 hours. TLC(50% EtOAc in petroleum ether, Rf=0.4) showed the starting material consumed. The mixture was filtered and washed with MeOH (50 mL×3), the filtrate was concentrated and purified by flash column chromatography (50-85% EtOAc in petroleum ether, TLC:60% EtOAc in petroleum ether, Rf=0.5) to give Compound 15.4 (6.500 g, 97.3%) as a yellow solid. $^1$H NMR (400 MHz, DMSO-d6) δ 7.12 (d, J=8.4 Hz, 1H), 7.07 (d, J=2.4 Hz, 1H), 6.72-6.69 (m, 1H), 5.54 (s, 2H), 4.67 (s, 2H), 3.75 (s, 3H), 2.75 (s, 3H).

Step 4: methyl 5-amino-4-iodo-2-(methylsulfonylmethyl)benzoate (Compound 15.5)

To a solution of Compound 15.4 (2.500 g, 10.28 mmol) in DMF (30 mL) was added NIS (3.467 g, 15.41 mmol). The reaction mixture was stirred at 22° C. for 16 hours. TLC (50% EtOAc in petroleum ether, Rf=0.5) showed the starting material consumed. The mixture was quenched with Na$_2$S$_2$O$_3$ (aq. 20 mL) and NaHCO$_3$ (aq. 20 mL), then extracted with EtOAc (30 mL×2). The organic layer was washed with water (20 mL×3) and brine (20 mL×3), dried over Na$_2$SO$_4$, concentrated and purified by flash column chromatography (20%-50% EtOAc in petroleum ether, Rf=0.5) to afford Compound 15.5 (1.700 g, 44.8%) as a yellow solid. $^1$H NMR (400 MHz, CDCl$_3$) δ 7.78 (s, 1H), 7.31 (s, 1H), 4.68 (s, 2H), 4.33 (s, 2H), 3.87 (s, 3H), 2.77 (s, 3H).

Step 5: (E)-2-(5-bromo-2-methoxy-3-nitro-4-pyridyl)-N,N-dimethyl-ethenamine (Compound 15.7)

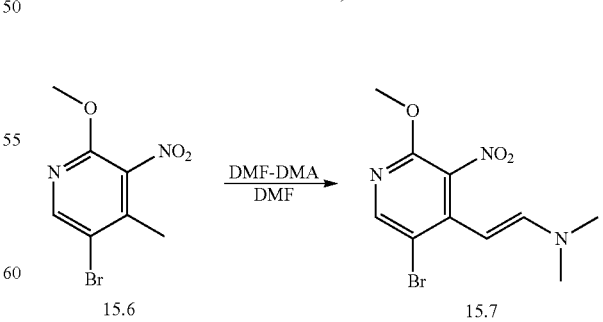

To a solution of Compound 15.6 (33.0 g, 133.58 mmol) and MeOLi (507.19 mg, 13.36 mmol) in DMF (250 mL) was added DMF-DMA (141.96 mL, 1068.6 mmol) at 100° C., and the reaction mixture was stirred at 100° C. for 16 hours.

TLC(15% EtOAc in petroleum ether, Rf=0.5) showed the starting material consumed. The mixture was cooled to 20° C., and quenched with water (60 mL) carefully. The resulting precipitate was collected by vacuum filtration, washed with water (50 mL×3) and dried to afford Compound 15.7 (37.0 g, 91.7%) as a red solid. The crude was used in the next step without further purification.

Step 6: 4-bromo-7-methoxy-1H-pyrrolo[2,3-c]pyridine (Compound 15.8)

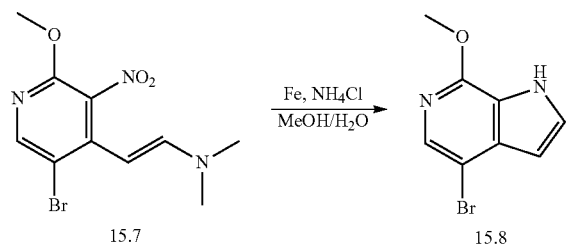

To a solution of Compound 15.7 (10.0 g, 33.1 mmol) in MeOH (50 mL) and water (10 mL) was added iron (9.24 g, 165.5 mmol) and NH$_4$Cl (8.85 g, 165.5 mmol), the mixture was stirred at 75° C. for 16 hours. TLC(20% EtOAc in petroleum ether Rf=0.5) showed the starting material consumed and the desired product found. The mixture was filtered and washed with MeOH (10 mL×3), the filtrate was concentrated and purified by column chromatography (0-15% EtOAc in petroleum ether) to give Compound 15.8 (3.3 g, 43.2%) as a white solid. LCMS (5-95_1.5 min): RT (220/254 nm)=0.598 min, [M+H]+ 226.9.

Step 7: 4-bromo-7-methoxy-1-(p-tolylsulfonyl)pyrrolo[2,3-c]pyridine (Compound 15.9)

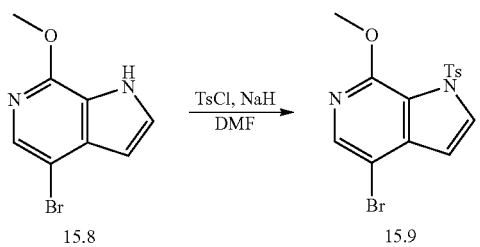

To a solution of NaH (858 mg, 21.45 mmol) in DMF (15 mL) was added Compound 15.8 (3.30 g, 14.3 mmol) at 0° C., and the mixture was stirred at 0° C. for 10 minutes. Then TsCl (5.452 g, 28.6 mmol) was added portion-wise, and the mixture was stirred at 0° C. under N$_2$ for 16 hours. TLC(30% EtOAc in petroleum ether Rf=0.6) showed the starting material consumed, and the desired product found. The mixture was quenched with water (10 mL), and the resulting precipitate was collected by vacuum filtration, washed with water (10 mL×3), and dried to afford Compound 15.9 (3.30 g, 60%) as a white solid which was used next step without further purification.

Step 8: 4-bromo-1-(p-tolylsulfonyl)-6H-pyrrolo[2,3-c]pyridin-7-one (Compound 15.10)

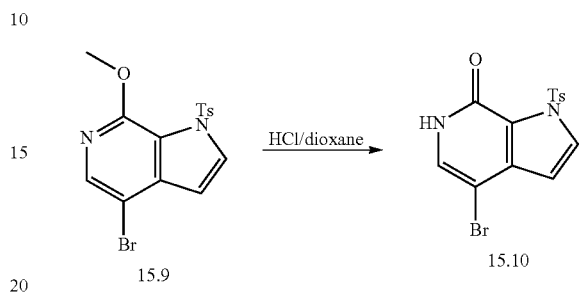

To a solution of Compound 15.9 (3.300 g, 8.65 mmol) in 1,4-dioxane (15 mL) was added a HCl solution in dioxane (4.0 M, 19.08 mL, 76.33 mmol). The solution was stirred at 40° C. for 16 hours. TLC(20% EtOAc in petroleum ether Rf=0.4) showed the starting material consumed, and the desired product found. The mixture was concentrated and MTBE (20 mL) was added. The resulting precipitate was collected by vacuum filtration, washed with MTBE (20 mL×2), and dried to give Compound 15.10 (3.00 g, 94%) as a beige solid. LCMS (5-95_1.5 min): RT (220/254 nm)=1.016 min, [M+H]$^+$ 368.9.

Step 9: 4-bromo-6-methyl-1-(p-tolylsulfonyl)pyrrolo[2,3-c]pyridin-7-one (Compound 15.11)

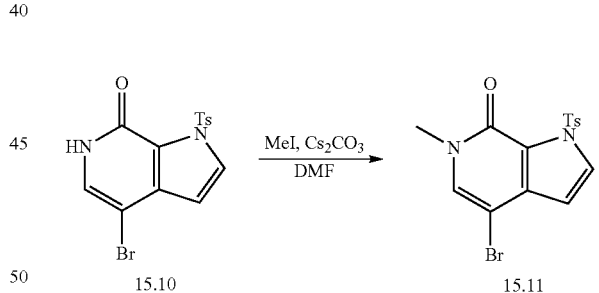

To a solution of Compound 15.10 (3.00 g, 8.17 mmol) in DMF (20 mL) was added Cs$_2$CO$_3$ (3.194 g, 9.8 mmol) under N$_2$ at 20° C., and the mixture was stirred at 20° C. for 30 minutes. MeI (1.80 mL, 28.6 mmol) was added and the solution was stirred at 20° C. for 3 hours. TLC(50% EtOAc in petroleum ether, Rf=0.5) showed the starting material consumed, and the desired product found. The mixture was quenched with water (50 mL), and the resulting precipitate was collected by vacuum filtration, washed with MTBE (50 mL×3), and dried to afford Compound 15.11 (2.50 g, 80%) as a white solid. LCMS (5-95_1.5 min): RT (220/254 nm)=0.95 min, [M+H]+ 383.

Step 10: 6-methyl-1-(p-tolylsulfonyl)-4-(4,4,5,5-tetramethyl-1,3,2-dioxaborolan-2-yl)pyrrolo[2,3-c]pyridin-7-one (Compound 15.12)

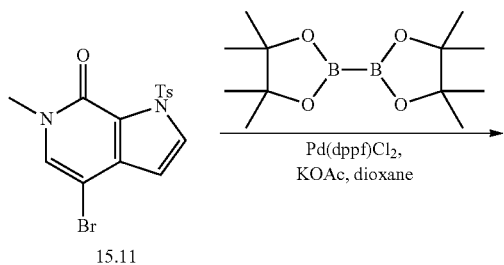

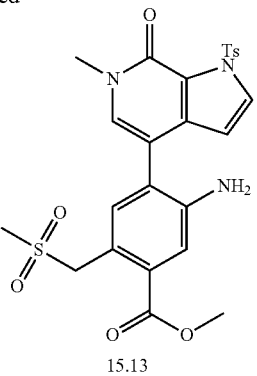

A mixture of Compound 15.12 (812.12 mg, 1.9 mmol), Pd(dppf)Cl$_2$ (115.7 mg, 0.1400 mmol), Compound 15.5 (500.0 mg, 1.35 mmol), NaHCO$_3$(284.45 mg, 3.39 mmol) in 1,4-dioxane (2.0 mL) and water (1.0 mL) was stirred at 90° C. under N$_2$ for 1 hour. The mixture was concentrated and purified by prep-TLC(5% MeOH in DCM, Rf=0.5) to afford Compound 15.13 (550 mg, 74.7%) as a yellow solid.

Step 12: methyl 5-((5-chloro-3-fluoropyridin-2-yl)amino)-4-(6-methyl-7-oxo-1-tosyl-6,7-dihydro-1H-pyrrolo[2,3-c]pyridin-4-yl)-2-((methylsulfonyl)methyl)benzoate (Compound 15.15)

A mixture of Compound 15.11 (2.00 g, 5.25 mmol), bis(pinacolato)diboron (3.330 g, 13.12 mmol), KOAc (1.287 g, 13.12 mmol), Pd(dppf)Cl$_2$ (433.7 mg, 0.520 mmol) in 1,4-dioxane (15 mL) was stirred at 90° C. under N$_2$ for 16 hours. TLC(50% EtOAc in petroleum ether, Rf=0.5) indicated the reaction was completed. The mixture was concentrated and purified by column chromatography (30%-50% EtOAc in petroleum ether) to afford Compound 15.12 (1.320 g, 57.6%) as a yellow oil. LCMS (5-95_1.5 min): RT (220/254 nm)=0.928 min, [M+H]+ 429.0.

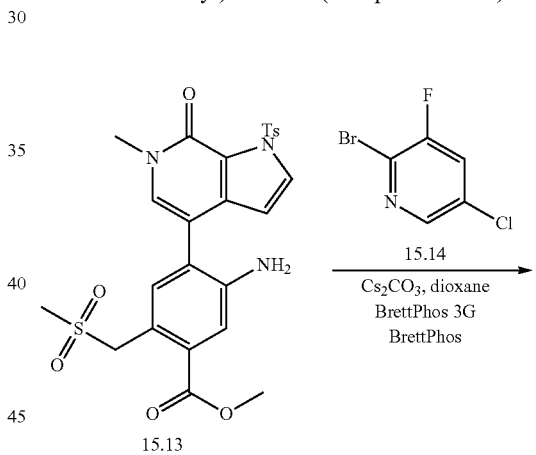

Step 11: methyl 5-amino-4-[6-methyl-7-oxo-1-(p-tolylsulfonyl)pyrrolo [2,3-c]pyridin-4-yl]-2-(methylsulfonylmethyl)benzoate (Compound 15.13)

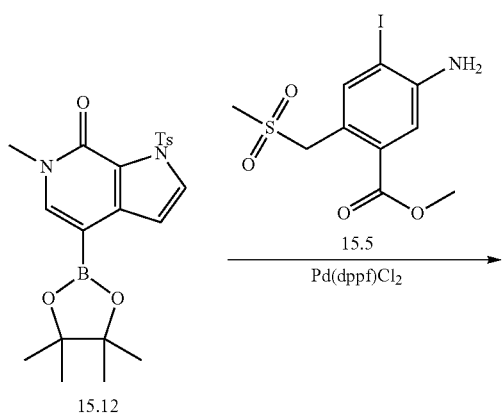

To a solution of Compound 15.14 (1.43 g, 6.8 mmol) in 1,4-Dioxane (10 mL) was added Cs$_2$CO$_3$ (1.329 g, 4.08 mmol), BrettPhos (365 mg, 0.68 mmol), Compound 15.13 (740 mg, 1.36 mmol) and BrettPhos Pd-G3 (247 mg, 0.27 mmol). The reaction was purged with N$_2$ for 3 minutes. The mixture was stirred at 100° C. under N₂ under microwave irradiation for 3 hours. The reaction was filtered and washed with MeOH (10 mL×3). The filtrate was dried over Na₂SO₄, concentrated, and the residue was purified by prep-TLC (5% MeOH in DCM, Rf=0.6) to afford Compound 15.15 (680 mg, 74%) as a yellow solid. LCMS (Method A): R$_T$=0.945 min, m/z=673.1 [M+1]⁺.

Step 13: methyl 5-((5-chloro-3-fluoropyridin-2-yl) amino)-4-(6-methyl-7-oxo-6,7-dihydro-1H-pyrrolo [2,3-c]pyridin-4-yl)-2-((methylsulfonyl)methyl)benzoate (Compound 15.16)

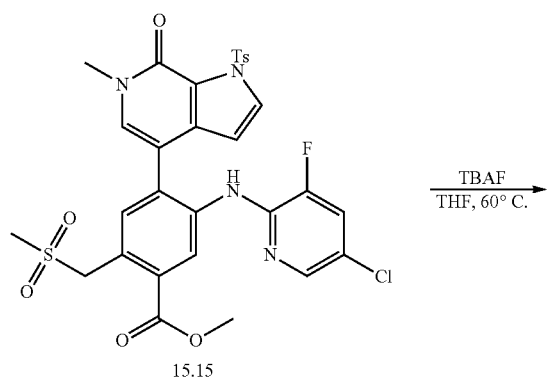

A mixture of Compound 15.15 (680.0 mg, 1.01 mmol) and a TBAF solution in THF (1.0 M, 30 mL) was stirred at 60° C. for 1 hour. The mixture was diluted with water (20 mL), extracted with DCM (20 mL×2), and the organic layer was washed with brine (20 mL×3). It was dried over Na₂SO₄, concentrated and purified by prep-TLC(5% MeOH in DCM, Rf=0.4) to afford Compound 15.16 (360 mg, 68%) as a yellow solid. LCMS (Method A): RT=0.842 min, m/z=519.1 [M+1]⁺.

Step 14: methyl 4-(5-chloro-3-fluoropyridin-2-yl)-10-methyl-7-((methylsulfonyl)methyl)-11-oxo-3,4, 10,11-tetrahydro-1H-1,4,10-triazadibenzo[cd,f]azulene-6-carboxylate (Compound 15.17)

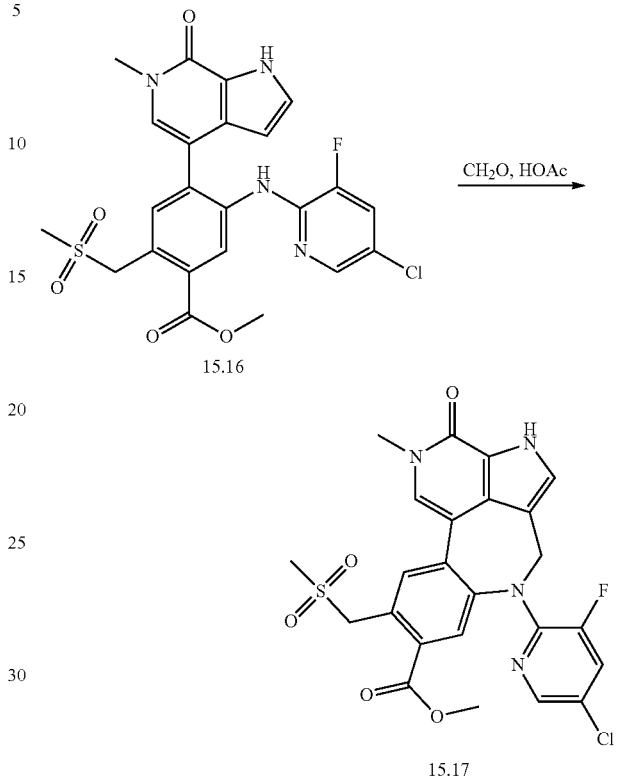

To a solution of Compound 15.16 (360.0 mg, 0.69 mmol) in acetic acid (5 mL) was added HCHO (103.6 mg, 3.45 mmol) under N₂, and the reaction mixture was stirred at 90° C. for 1 hour. The mixture was concentrated and purified by prep-TLC(5% MeOH in DCM, Rf=0.4) to afford Compound 15.17 (170 mg, 46%) as a yellow solid. LCMS (Method A): R$_T$=0.849 min, m/z=531.1 [M+1]⁺; ¹H NMR (400 MHz, CDCl₃) δ 9.66 (brs, 1H), 7.91 (s, 1H), 7.84 (s, 1H), 7.44 (s, 1H), 7.15-7.04 (m, 2H), 6.06-6.02 (m, 1H), 5.01-4.94 (m, 2H), 4.27-4.24 (m, 1H), 3.87 (s, 3H), 3.73 (s, 3H), 2.87 (s, 3H).

Step 15: methyl 4-(5-(3-((tert-butoxycarbonyl) amino)prop-1-yn-1-yl)-3-fluoropyridin-2-yl)-10-methyl-7-((methylsulfonyl)methyl)-11-oxo-3,4,10, 11-tetrahydro-1H-1,4,10-triazadibenzo[cd,f]azulene-6-carboxylate (Compound 15.19)

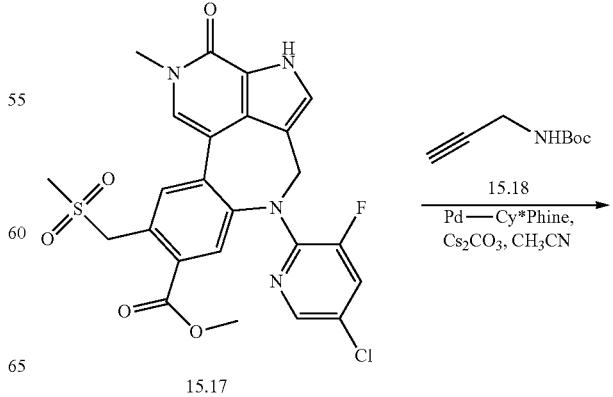

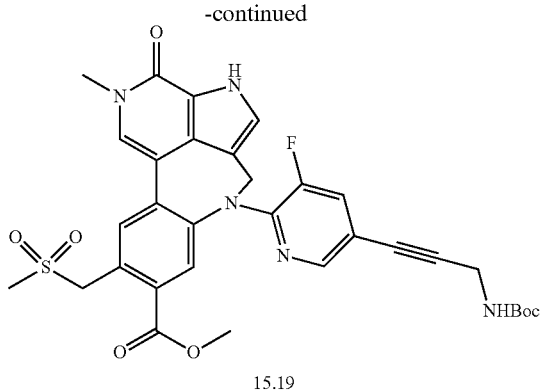

15.19

To a mixture of Compound 15.17 (80.0 mg, 0.15 mmol) in acetonitrile (2.0 mL) was added Pd-Cy*Phine (96.7 mg, 0.075 mmol), $Cs_2CO_3$ (146.62 mg, 0.45 mmol) and Compound 15.18 (116.19 mg, 0.75 mmol) under $N_2$. The mixture was stirred at 95° C. under microwave irradiation under the $N_2$ for 1.5 hours. The mixture was concentrated and purified by prep-TLC(5% MeOH in DCM, Rf=0.3) to afford Compound 15.19 (42 mg, 43.1%) as a yellow solid. LCMS (Method A): RT=0.879 min, m/z=650.2 [M+1]$^+$.

Step 16: methyl 4-(5-(3-aminoprop-1-yn-1-yl)-3-fluoropyridin-2-yl)-10-methyl-7-((methylsulfonyl)methyl)-11-oxo-3,4,10,11-tetrahydro-1H-1,4,10-triazadibenzo[cd,f]azulene-6-carboxylate (Compound 15)

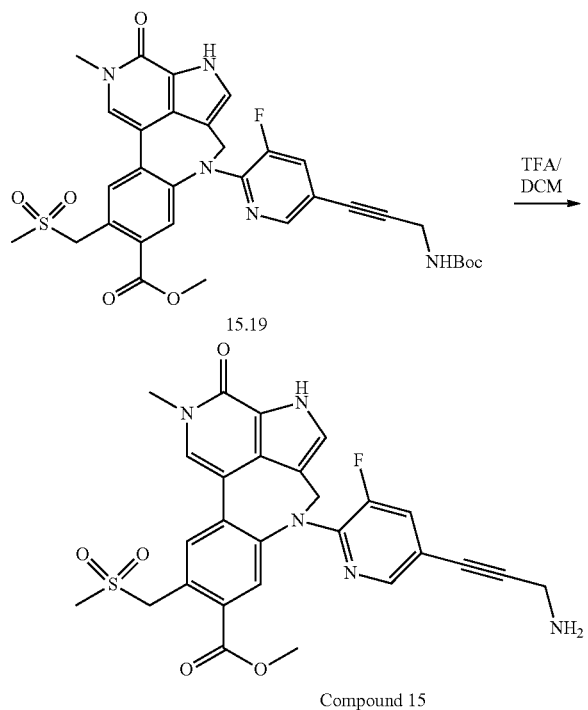

To a solution of Compound 15.19 (17.0 mg, 0.030 mmol) in DCM (2.5 mL) was added TFA (0.5o mL) and the mixture was stirred at 20° C. for 1 hour. The mixture was concentrated and the resulting residue was purified by prep-HPLC (15-45 water (0.225% FA)-ACN) to afford the product Compound 15 as formic acid salt (5.77 mg, 37%) as a white solid. HPLC(10-80AB/8 min): RT=3.52 min, showed 98.56% of desired product. LCMS (Method A): $R_T$=0.724 min, m/z=550.1 [M+1]$^+$; $^1$H NMR (400 MHz, DMSO-d6) δ 11.97 (s, 1H), 8.19 (s, 1H), 8.01 (s, 1H), 7.98 (s, 1H), 7.81 (s, 1H), 7.63 (s, 1H), 7.39 (dd, J=1.6, 13.6 Hz, 1H), 7.28 (s, 1H), 5.99 (br d, J=15.6 Hz, 1H), 5.16 (br d, J=15.2 Hz, 1H), 4.80 (br d, J=12.4 Hz, 1H), 4.24 (br d, J=17.2 Hz, 1H), 3.76 (s, 3H), 3.60 (s, 3H), 3.50 (s, 2H), 2.93 (s, 3H).

Example 16 tert-butyl (S)-2-(4-(4-(4-aminobutyl)phenyl)-2,3,9-trimethyl-6H-thieno[3,2-f][1,2,4]triazolo[4,3-a][1,4]diazepin-6-yl)acetate

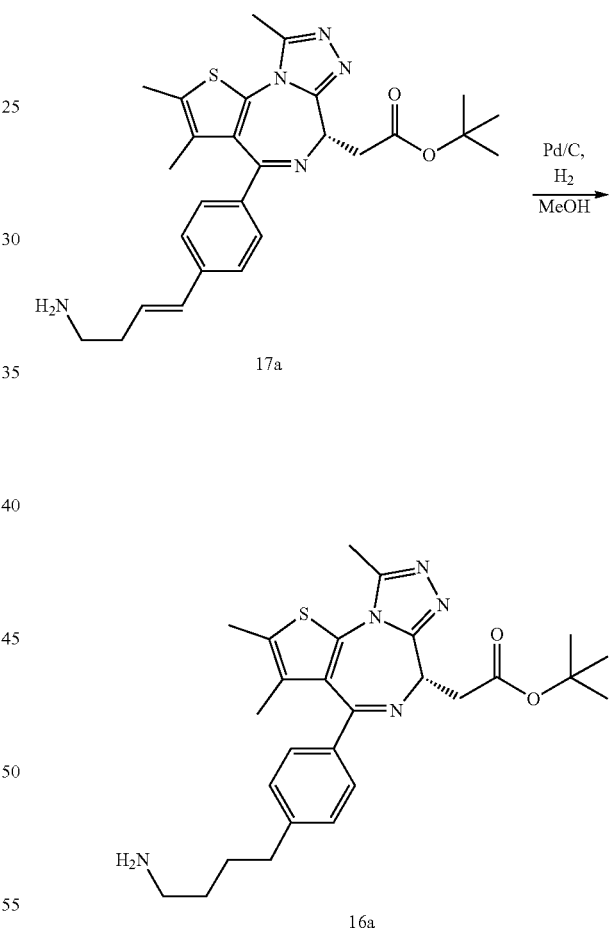

To solution of compound 17a (vide infra)(0.210 mmol) in anhydrous MeOH (6.0 mL) was added 10% Pd/C(112 mg). The reaction mixture was stirred at 20° C. under H2 for 0.5 h. The catalyst was filtered and the filtrate was concentrated in vacuo. The residue was separated by SFC(Supercritical CO2/EtOH-0.1% $NH_3H_2O$=30%; 60 ml/min), and then purified by prep-HPLC(Xtimate C18 150*25 mm*5 um, acetonitrile 20-50/0.225% FA in water) to afford compound 16a.

Example 17 tert-butyl (S,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate

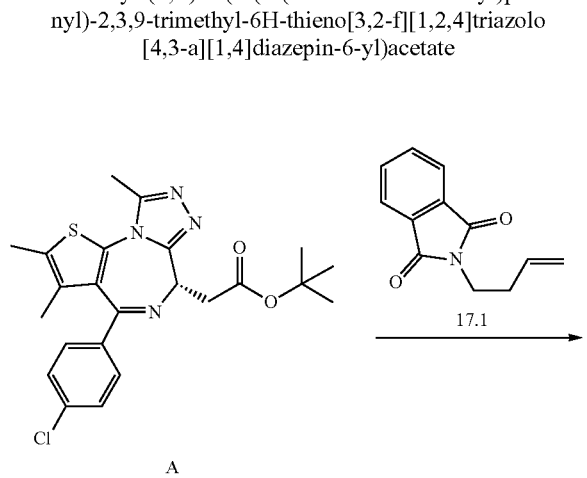

Step 1: Compound 17.2

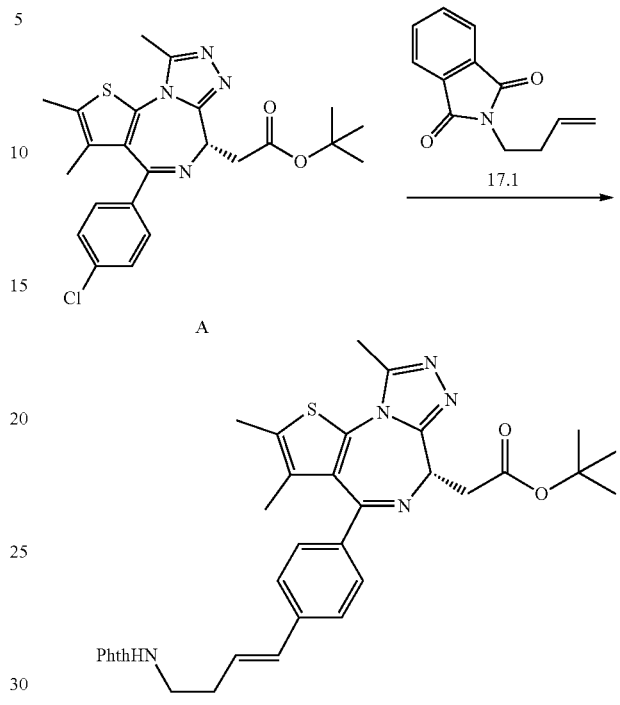

To a solution of $Pd_2(dba)_3$ (12.0 mg, 0.01 mmol) in NMP (3.0 mL) was added Compound A (30.0 mg, 0.07 mmol), [t-$Bu_3$PH]$^+$$BF_4^-$ (38.5 mg, 0.20 mmol), Compound 17.1 (0.20 mmol) and $Cy_2$NMe (15.2 mg, 0.05 mmol). The mixture was stirred at 160° C. for 20 minutes under microwave irradiation. Then the mixture was filtered, concentrated, and diluted with water (10.0 mL). The resulting solution was extracted with EtOAc (10 mL×3) and the combined organic layer was dried over anhydrous $Na_2SO_4$ and concentrated. The residue was purified by column chromatography (0-50% EtOAc in PE) to afford the desired product (Compound 17.2).

Step 2: tert-butyl (S,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate

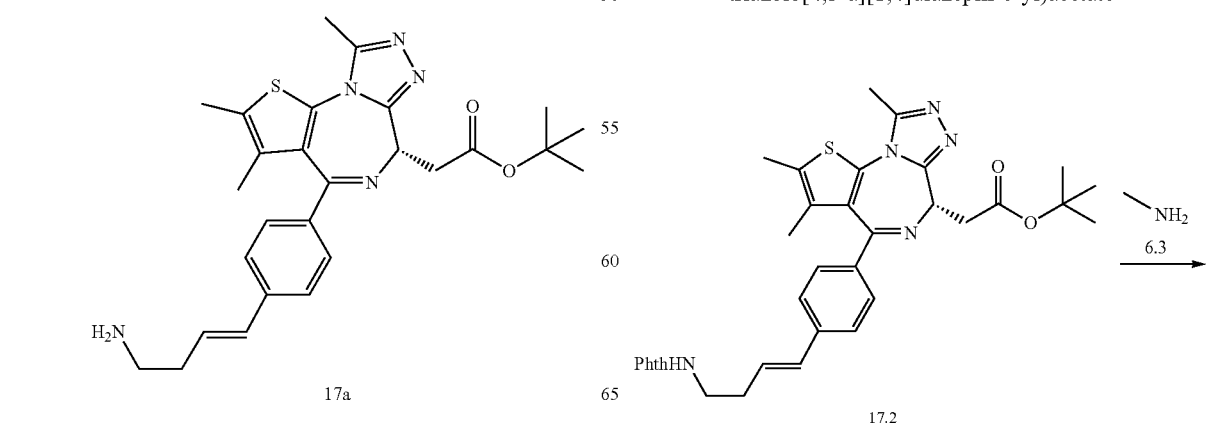

-continued

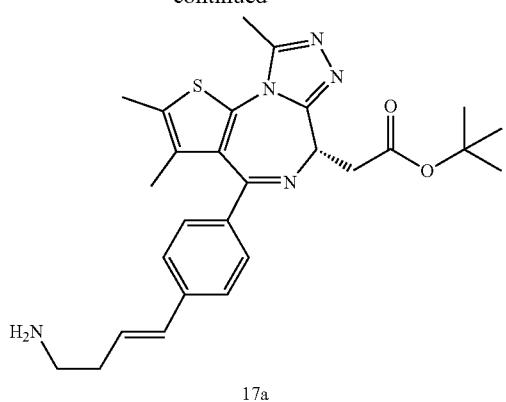

17a

A solution of Compound 17.2 (0.06 mmol) in CH₃NH₂/THF (2.0 mol/L, 10 mL) was stirred for 16 hours at 80° C. The mixture was concentrated, and purified by prep-HPLC (CN₃CN 20-50/0.1% FA in water) to afford the desired product (Compound 17a).

Example 20 tert-butyl (S,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate -continued

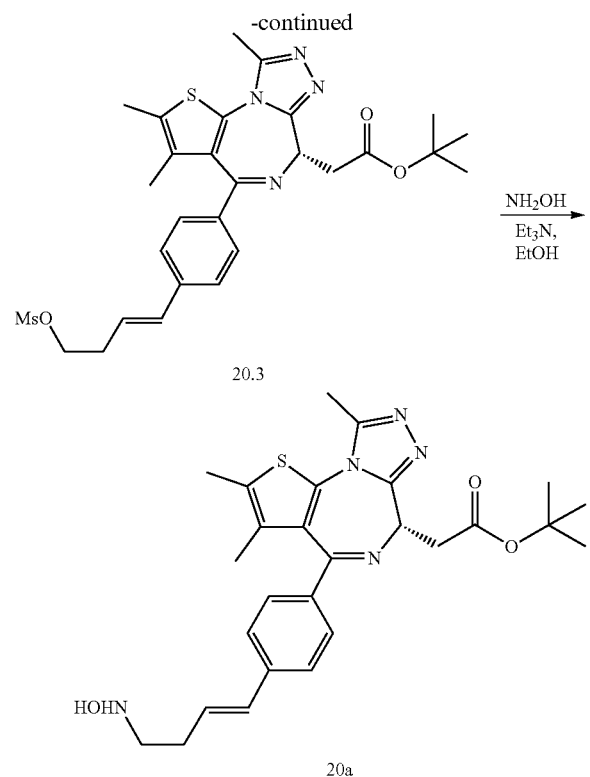

Step 1: Compound 20.2

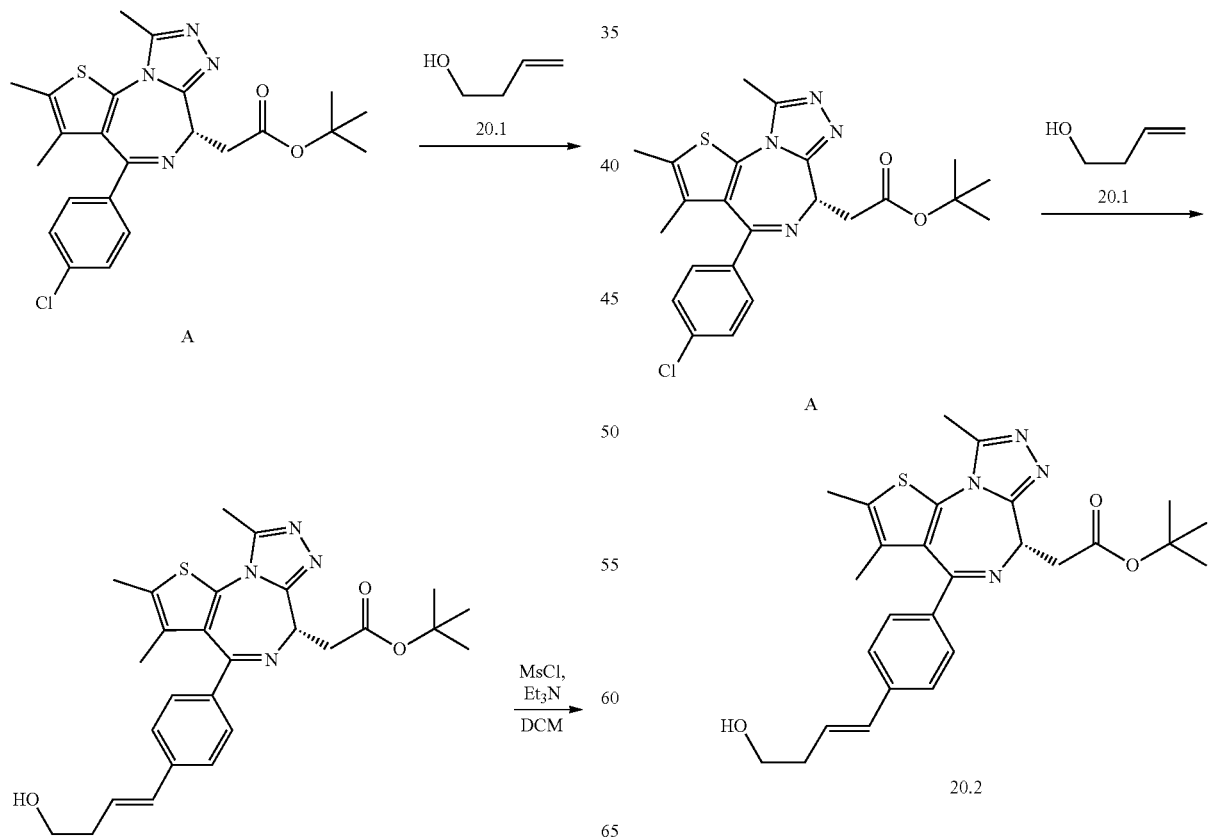

To a solution of Pd₂(dba)₃ (12.0 mg, 0.01 mmol) in NMP (3.0 mL) was added Compound A (30.0 mg, 0.07 mmol),

[t-Bu₃PH]⁺BF₄⁻ (38.5 mg, 0.20 mmol), Compound 20.1 (0.20 mmol) and Cy₂NMe (15.2 mg, 0.05 mmol). The mixture was stirred at 160° C. for 20 minutes under microwave irradiation. Then the mixture was filtered, concentrated, and diluted with water (10.0 mL). The resulting solution was extracted with EtOAc (10 mL×3) and the combined organic layer was dried over anhydrous Na₂SO₄ and concentrated. The residue was purified by column chromatography (0-50% EtOAc in PE) to afford the desired product (Compound 20.2).

Step 2: Compound 20.3

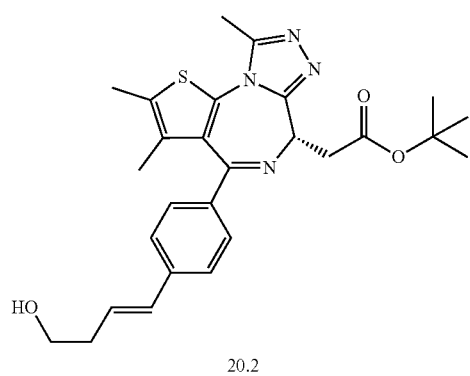

20.2

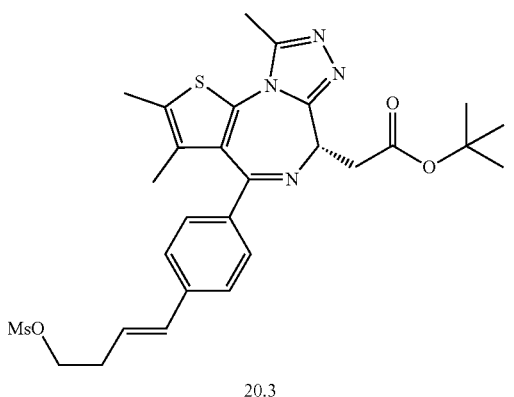

20.3

To Compound 20.2 (0.29 mmol) in DCM (10 mL) was added Et₃N(148.62 mg, 1.47 mmol) and MsCl (310.0 mg, 2.71 mmol). After the mixture was stirred at 25° C. for 1 hour, it was diluted with DCM (30 mL) and washed with water (10 mL×3). The organic layer was dried over anhydrous sodium sulfate, and concentrated to give Compound 20.3.

Step 3: tert-butyl (S,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate

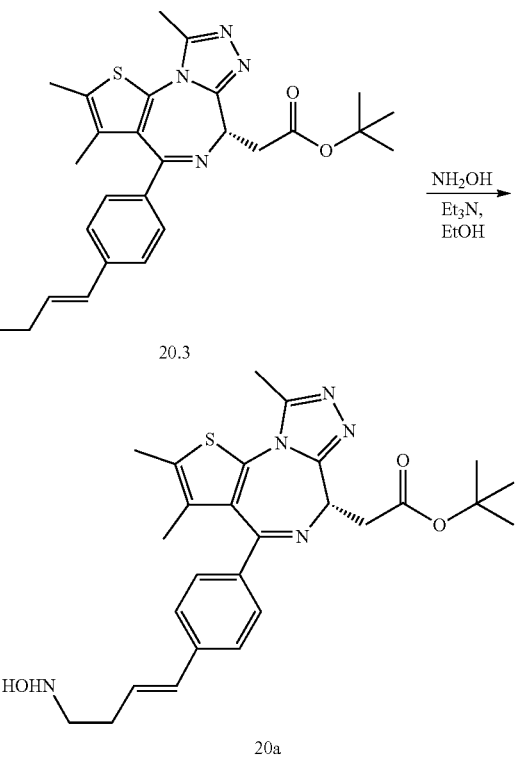

To a mixture of Compound 20.3 (0.290 mmol) in EtOH (10 mL) was added hydroxylamine (40.09 mg, 0.580 mmol) and Et₃N(87.57 mg, 0.870 mmol). The mixture was stirred at 90° C. for 1 hour. The mixture was concentrated and diluted with EtOAc (30 mL) and washed water (10 mL). The organic layer was concentrated and purified by prep-HPLC (acetonitrile 0-40/0.1% HCl in water) to afford the desired product (Compound 20a).

Example 23 tert-butyl (S)-2-(4-(4-(4-(hydroxyamino)butyl)phenyl)-2,3,9-trimethyl-6H-thieno[3,2-f][1,2,4]triazolo[4,3-a][1,4]diazepin-6-yl)acetate

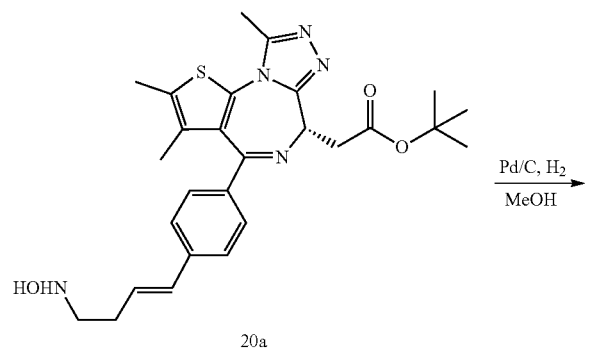

20a

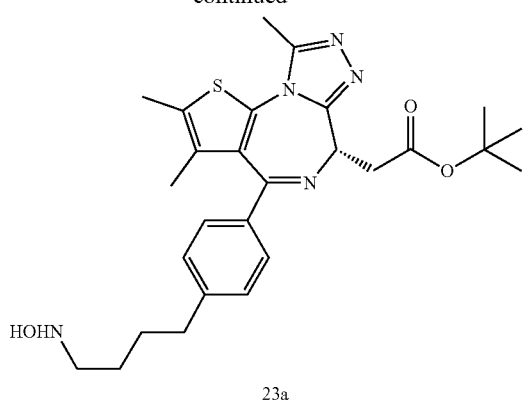

23a

To solution of compound 20a (0.210 mmol) in anhydrous MeOH (6.0 mL) was added 10% Pd/C(112 mg). The reaction mixture was stirred at 20° C. under $H_2$ for 0.5 h. The catalyst was filtered and the filtrate was concentrated in vacuo. The residue was separated by SFC(Supercritical $CO_2$/EtOH-0.1% $NH_3H_2O$=30%; 60 ml/min), and then purified by prep-HPLC (Xtimate C18 150*25 mm*5 um, acetonitrile 20-50/0.225% FA in water) to afford compound 23a.

Example 24 tert-butyl (S)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate

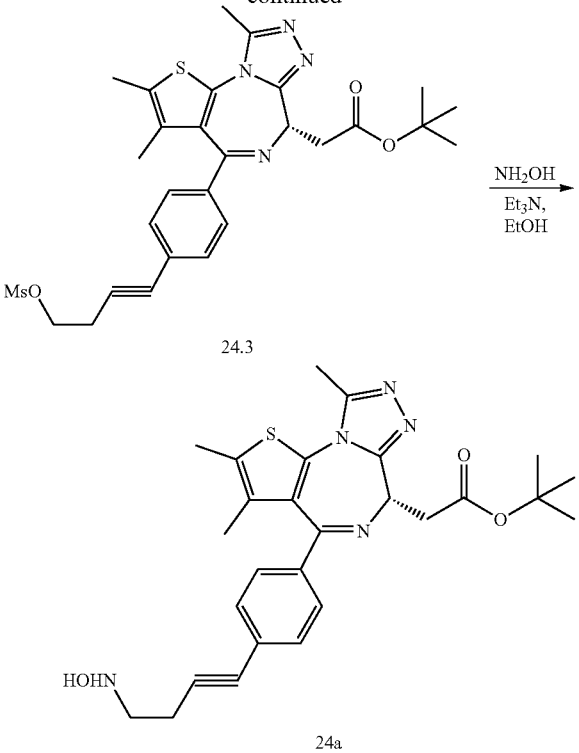

24.3

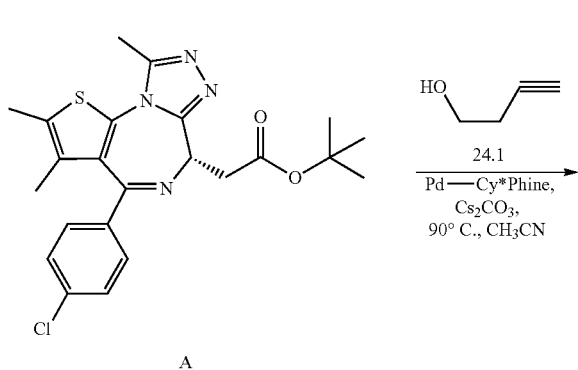

24a

Step 1: Compound 24.2

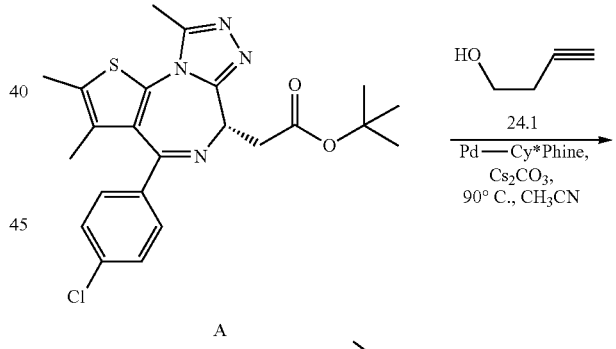

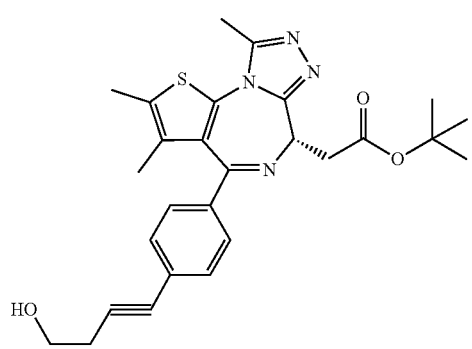

24.2

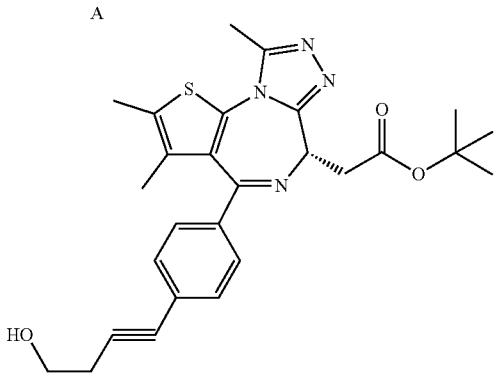

24.2

To a mixture of Compound A (2.63 mmol) in acetonitrile (12 mL) was added Pd-Cy*Phine (similar transformations described in *Eur. J Org. Chem.*, 2014, Vol. 32, pp. 7184-7192)(168.44 mg, 0.1300 mmol), $Cs_2CO_3$ (2.566 g, 7.88 mmol) and Compound 24.1 (723.17 mg, 13.13 mmol). The mixture was stirred at 90° C. in under microwave irradiation for 1 hour. The reaction mixture was filtered and purified by flash column chromatography (0-8% MeOH in DCM) to afford the product (24.2).

Step 2: Compound 24.3

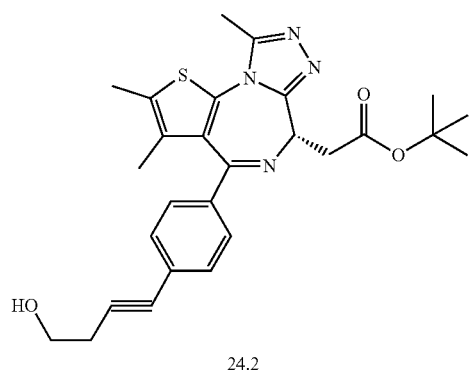

24.2

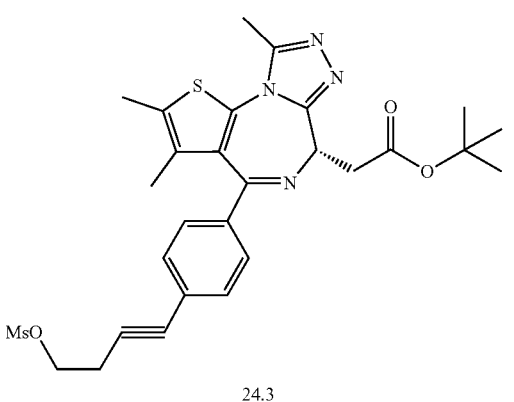

24.3

To Compound 24.2 (0.29 mmol) in DCM (10 mL) was added $Et_3N$(148.62 mg, 1.47 mmol) and MsCl (310.0 mg, 2.71 mmol). After the mixture was stirred at 25° C. for 1 hour, it was diluted with DCM (30 mL) and washed with water (10 mL×3). The organic layer was dried over anhydrous sodium sulfate, and concentrated to give Compound 24.3.

Step 3: tert-butyl (S)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate

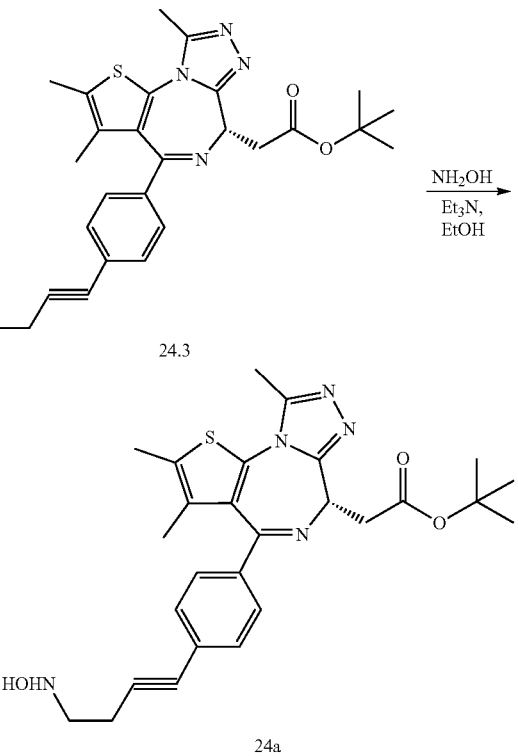

24a

To Compound 24.3 (0.290 mmol) in EtOH (10 mL) was added hydroxylamine (40.09 mg, 0.580 mmol) and $Et_3N$ (87.57 mg, 0.870 mmol). The mixture was stirred at 90° C. for 1 hour. The mixture was concentrated and diluted with EtOAc (30 mL) and washed water (10 mL). The organic layer was concentrated and purified by prep-HPLC(acetonitrile 0-40/0.1% HCl in water) to afford the desired product (Compound 24a).

Biological Assays

Example A: BRD4 BD1 and BD2 Biochemical Binding Assays

The following assay was used to measure the $IC_{50}$ for the test compounds ability to bind to the BRD4_BD1 and BRD4_BD2 bromodomains.

Binding of his6-tagged BRD4_BD1 bromodomain or his6-tagged BRD4_BD2 to a biotinylated bromodomain ligand (Compound C) was monitored by time resolved fluorescence resonance energy transfer (TR-FRET). Competitive binding of small molecules that bind to the bromodomain was detected by the displacement the biotinylated tracer and consequent decrease in the measured emission intensity at 665 nm or the emission ratio (emission at 665 nm/emission at 615).

Test compounds were transferred to the assay plate (PE 384-well white ProxiPlate PerkinElmer cat #6008289) using an Echo 555 Liquid Handler (Labcyte) in 2.5 nL increments and, as appropriate, intermediate stock concentrations of compounds, in order to prepare titration series. DMSO was backfilled to a final volume of 30 nL as required. The assay reagents (his6-tagged BRD4_BD1 bromodomain or his6-tagged BRD4_BD2, biotin-ligand (Compound C), and Eu-W1024 anti 6xHis antibody) were thawed at room temperature. 1x Assay Buffer was prepared (50 mM HEPES (Sigma cat #H3375), pH 7.5, 1 mM TCEP (Sigma cat #646547), 0.069 mM Brij-35 (Calbiochem cat #203728), 50 mM, NaCl (Sigma cat #S7653), 0.1 mg/mL BSA (Sigma cat #A9576)). Solution A-3x (0.0075 μM His-Flag BRD4_BD1 in Assay Buffer.), Solution B-3x (0.075 μM Compound C in Assay Buffer), and Solution C-3x (0.3 μM Streptavidin Surelight (SA-APC)(PerkinElmer cat #CR130-100), 0.6 nM Eu-W1024 anti 6xHis antibody (PerkinElmer cat #AD0110) diluted in Assay Buffer) were prepared. 1x Assay Buffer was dispensed (5 μL per well) into Minimum Signal control wells. 5 μL of Solution A-3x was dispensed into test wells and Maximum Signal control wells (containing DMSO instead of test compound). Samples were incubated 10 minutes at room temperature. 5 μL of Solution B-3x was dispensed into all wells. Samples were incubated incubate for 10 minutes at room temperature. 5 μL of Solution C-3x was dispensed into all wells. Samples were incubated 40 minutes at room temperature. Plates were read using an Envision (Perkin Elmer) with the following settings: Detection—LANCE Dual Laser 50/200. Mirror: LANCE/Delfia Dual/Bias D400/D630 PE Barcode 446. Light Source: TRF Laser (337 nm) Emission filter: APC 665 (PE Barcode 205)—Wavelength: 665 nm/7.5 nm bandwidth. 2nd Emission filter: Europium 615 (PE Barcode 203)—Wavelength: 615 nm/8.5 nm bandwidth. Percentage inhibition was calculated relative to the Minimum Signal control and Maximum Signal control wells. $IC_{50}$ values were derived by four parameter curve fitting using the Robust method.

The structure of Compound C is below.

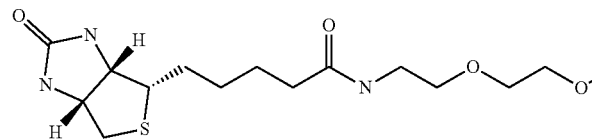

The results are set forth in Table 2.

TABLE 2

| Compound | BRD4-BD1 and BD2 Binding | |
|---|---|---|
| | BRD4-BD1 Average $IC_{50}$ (μM) | BRD4-BD2 Average $IC_{50}$ (μM) |
| A | 0.0288 | 0.0269 |
| 1a | 0.0155 | 0.0123 |
| 1b | 0.1990 | 0.2718 |
| 2a | 0.0144 | 0.0171 |
| 3a | 0.0145 | 0.0207 |
| 4a | 0.0130 | 0.0177 |
| 5a | 0.0072 | 0.0085 |
| 6a | 0.0256 | 0.0153 |
| 7a | 0.0178 | 0.0103 |
| 8a | 0.0211 | 0.0276 |
| 9a | 0.0233 | 0.0194 |
| 10a | 0.0066 | 0.0107 |

TABLE 2-continued

| Compound | BRD4 BD1 and BD2 Binding | |
|---|---|---|
| | BRD4-BD1 Average $IC_{50}$ (μM) | BRD4-BD2 Average $IC_{50}$ (μM) |
| 11a | 0.0141 | 0.0106 |
| 12a | 0.0113 | 0.0081 |
| 13a | 0.0234 | 0.0287 |
| 14a | 0.0188 | 0.0203 |
| 15 | 0.0033 | 0.0037 |

Example B: BRD4 Full Length Binding Assays in Cells

The BRD4 NanoBRET™ Target Engagement Assay analyzes the apparent affinity of test compounds for BRD4 in cells by competitive displacement of a BRD4 NanoBRET™ tracer reversibly bound to a NanoLuc® BRD4 fusion protein stably expressed in the cells.

Test compounds were transferred to the assay plate (384 Well White Non-Binding Corning Assay Plates (Corning-3574)) using an Echo 555 Liquid Handler (Labcyte) in 2.5 nL increments and, as appropriate, intermediate stock concentrations of compounds, in order to prepare a titration series. DMSO was backfilled to a final volume of 20 nL as required. 20 nL of 2000x BRD4 nanoBRET tracer in DMSO (Promega) was transferred into each well using an Echo 555. HEK 293 RT BRD4-NanoLuc® stable cells were cultured in DMEM High Glucose with Pyruvate, 10% fetal bovine serum, 2 mg/mL of Geneticin Selective Antibiotic (50 mg/mL) and 2 mM HEPES (1 M). Cells were seeded in Opti-MEM (Life Technologies-11058-021), 1.7x105 cells/mL, 40 μL per well into the assay plate, centrifuged at 500 rpm for 30 seconds and incubated for 2 hours. Max Signal control wells consisted of DMSO only treated wells. Minimum Signal control wells contained of 10 uM JQ1 (BRD4 antagonist—Compound A). 3x Complete Substrate plus Inhibitor Solution was prepared in Opti-MEM (consists of a 1:166 dilution of NanoBRET™ Nano-Glo® Substrate plus a 1:500 dilution of Extracellular NanoLuc® Inhibitor in Opti-MEM), and 20 μL was dispensed into each well of the 384-well plate and centrifuged at 1000 rpm for 1 minute, then incubated for 2 minutes at room temperature. Background Signal control wells were prepared without tracer for background correction steps.

Plates were read using a PerkinElmer Envision Reader (model 2104-0020) equipped with Luminescence option (Mirror: BRET2 Enh (PE Barcode 659), Emission Filter: Omega 610LP (Barcode 504), 2nd Emission Filter: Umbelliferone 460 (Barcode 207), Measurement height: 6.5 mm, Measurement time: 1 s). The raw BRET ratio values were

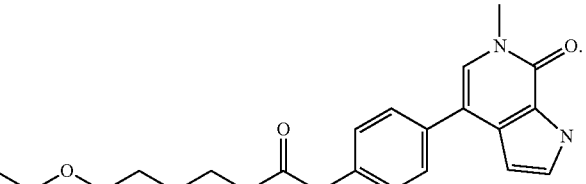

calculated by dividing the acceptor emission value (610 nm) by the donor emission value (460 nm) for each sample. To correct for background, the BRET ratio in the absence of tracer (average of no-tracer control samples) was subtract from the BRET ratio of each sample. Raw BRET units were converted to milliBRET units (mBU) by multiplying each raw BRET value by 1,000. The normalized NanoBRET signal was calculated relative to the Max Signal control wells (DMSO treated control wells) and the Minimum Signal control wells. Percentage inhibition was calculated relative to the Minimum Signal control and Maximum Signal control wells. $IC_{50}$ values were derived by four parameter curve fitting using the Robust method.

The results are set forth in Table 3 below.

TABLE 3

| BRD4 Full Length Binding | |
|---|---|
| Compound | Average $IC_{50}$ |
| A (JQ1) | 0.0376 |
| 1a | 0.0271 |
| 1b | 0.2638 |
| 2a | 0.0133 |
| 3a | 0.0131 |
| 4a | 0.0116 |
| 5a | 0.1388 |
| 9a | 0.0296 |
| 10a | 0.0109 |

Example C: BRD4 Degradation Assay in PC3-Steap1 Cells

PC3 prostate cancer cells, which were engineered to overexpress the Steap-1 gene (made using lipofectamine to transfect Steap1 gene (pRK vector) into PC-3 cells obtained from ATCC), were seeded on day-1 at a density of 9000 cells per well in CellCarrier-384 Ultra Microplates, tissue culture treated (Perkin Elmer #6057300) in 45 µL/well of assay media (RPMI, 10% FBS, containing 2 mM L-glutamine). On day-2, compounds were serially diluted 1/3 in dimethylsulfoxide (DMSO) to create 20-point dilutions across a 384 well v-bottom polypropylene microplate (Greiner #781091). 2 µL of each sample from the serial dilution was transferred to 98 µL of assay media as an intermediate dilution. 5 µL of intermediate dilution was added to 45 µL of cell plate. Columns 1, 2, 23 and 24 were treated with only 0.2% w/v final concentration of DMSO for data normalization as "neutral controls". After compound treatment, cell plates were stored in a 37° C. incubator for 4 hours.

After 4 hours cells were fixed in 3.7% final concentration of paraformaldehyde by addition of 15 µL of 16% w/v paraformaldehyde (Electron Microscopy Sciences #15710-S) directly to the 50 µL media and compound in the cell plate. Cell plate was incubated at room temperature for 20 minutes. Well contents were aspirated and washed with 100 µL/well PBS 3 times. 50 µL/well of PBS containing 0.5% w/v bovine serum albumen, 0.5% w/v Triton X-100 (Antibody Dilution Buffer) was added to each well. Samples were incubated for 30 minutes. Well contents were aspirated and washed 3 times with 100 µL/well of PBS. PBS was aspirated from the wells.

Immunofluorescence staining of BRD4 was carried out by diluting mAB Anti-BRD4 [EPR5150] antibody (Abcam 128874) 1:500 into Antibody Dilution Buffer (PBS, Triton X100 0.5%, BSA 0.5%). 25 µL per well of BRD4 antibody diluted in buffer was added and incubated overnight at 4° C. On day-3 samples were washed 3 times with 100 µL/well of PBS. 25 µL/well of secondary antibody solution (Goat Anti-Rabbit IgG, DyLight 488 Conjugated Highly Cross-adsorbed Thermo Fisher #35553) and Hoechst 33342 1 µg/mL diluted in Antibody Dilution Buffer) were dispensed into each well. Hoechst 33342 only was added to the bottom 3 columns for data normalization as "inhibitor controls". Samples were incubated for 2 hours at room temperature. Samples were washed 3 times with 100 µL PBS.

Quantitative fluorescence imaging of BRD4 was carried out using an Opera Phenix High-Content Screening System. Fluorescent images of the samples were captured using 488 nm and 405 nm channels. Hoechst channel was used to identify nuclear region. Mean 488 intensity of BRD4 quantitated in nuclear region. Data analysis was carried out using Genedata Screener, with DMSO and no primary antibody control treated samples being used to define the 0% and 100% changes in BRD4. The dose-response log(inhibitor) vs. response was used to define the inflexion point of curve ($IC_{50}$) and the plateau of the maximal effect. The $S_{inf}$ value reports degradation as percent change in protein level, so complete loss of the protein target is −100%. $S_{inf}$ is the maximum degradation achieved, obtained by determining the bottom of a dose-response (where the S-shaped curve levels out).

The results are set forth in Table 4.

TABLE 4

| Degradation of BRD4 in PC3-Steap1 cells | | |
|---|---|---|
| Compound | Average $EC_{50}$ (µM) | $S_{inf}$ (%) |
| A | >20.0 | |
| 1a | 0.0014 | −84.6 |
| 1b | 0.0105 | −74.5 |
| 2a | >20.0 | −21.8 |
| 3a | >20.0 | −41.9 |
| 4a | 0.0034 | −54.7 |
| 5a | 0.101 | −86 |
| 6a | 0.0048 | −73.1 |
| 7a | >20.0 | |
| 8a | 0.0024 | −92.6 |
| 9a | 0.2262 | −57.6 |
| 10a | >20.0 | |
| 11a | >20.0 | −43.3 |
| 12a | >20.0 | |
| 13a | >20 | |
| 14a | >20 | |
| 15 | >20 | |

Example D: BRD4 Degradation Assay in EoL-1 Cells

EoL-1 eosinophilic leukemia cells were seeded on day 1 at a density of 45,000 cells per well in Corning PureCoat Amine Microplates, (Corning #354719) in 45 µL/well of assay media (RPMI, 10% FBS, containing L-glutamine). After cells attached to the cell plate, compounds were serially diluted 1/3 in dimethylsulfoxide (DMSO) to create 20-point dilutions across a 384 well v-bottom polypropylene microplate (Greiner #781091). 2 µL of each sample from the serial dilution was transferred to 98 µL of assay media as an intermediate dilution. 5 µL of each well of the intermediate dilution was added to 45 µL of cell plate. Columns 1, 2, 23 and 24 were treated with only 0.2% final concentration of DMSO for data normalization as "neutral controls". After compound treatment, cell plates were stored in a 37° C. incubator for 4 hours.

After 4 hours, cells were fixed in 3.7% w/v final concentration of paraformaldehyde by addition of 15 µL of 16% w/v paraformaldehyde (Electron Microscopy Sciences #15710-S) directly to the 50 µL media and compound in the cell plate. The cell plate was incubated at room temperature for 20 minutes. Well contents were aspirated and washed with 100 µL/well PBS 3 times. 50 µL/well of PBS (pH7.5) containing 0.5% w/v bovine serum albumen, 0.5% w/v Triton X-100 (Block/Permeabilzation Buffer) was added to each well. Samples were incubated for 20 minutes. Well contents were aspirated and washed 3 times with 100 µL/well of PBS. PBS was aspirated from the well and 50 µL per well of EoL-1 Block Buffer (PBS containing 10% Normal Goat Serum (Abcam #ab7481)) was added to each well. Plates were incubated at room temperature for 30 minutes. Block buffer was decanted from the wells.

Immunofluorescence staining of BRD4 was carried out by diluting mAB Anti-BRD4 [EPR5150] antibody (Abcam 128874) 1:500 into Antibody Dilution Buffer (PBS, 2% Normal Goat Serum). 25 µL per well of BRD4 antibody diluted in buffer was added and incubated overnight at 4° C. On day-2 samples were washed 3 times with 100 µL/well of PBS. 25 µL/well of secondary antibody solution (Goat Anti-Rabbit IgG, DyLight 488 Conjugated Highly Crossadsorbed Thermo Fisher #35553) and Hoechst 33342 1 µg/mL diluted in Antibody Dilution Buffer) were dispensed into each well. Hoechst 33342 only was added to bottom 3 columns for data normalization as "inhibitor controls". Samples were incubated for 2 hours at room temperature. Samples were washed 3 times with 100 µL PBS.

Quantitative fluorescence imaging of BRD4 was carried out using an Opera Phenix High-Content Screening System. Fluorescent images of the samples were captured using 488 nm and 405 nm channels. Hoechst channel was used to identify nuclear region. Mean 488 intensity of BRD4 quantitated in nuclear region. Data analysis was carried out using Genedata Screener, with DMSO and no primary antibody control treated samples being used to define the 0% and 100% changes in BRD4. The dose-response log(inhibitor) vs. response was used to define the inflexion point of curve ($IC_{50}$) and the plateau of the maximal effect. The $S_{inf}$ value reports degradation as percent change in protein level, so complete loss of the protein target is −100%. $S_{inf}$ is the maximum degradation achieved, obtained by determining the bottom of a dose-response (where the S-shaped curve levels out).

The results are set forth in Table 5.

TABLE 5

Degradation of BRD4 in EoL-1 Cells

| Compound | Average $EC_{50}$ (µM) | $S_{inf}$ (%) |
| --- | --- | --- |
| A | >20.0 | |
| 1a | 0.0013 | −83.8 |
| 1b | 0.009 | −87.05 |
| 2a | >20.0 | |
| 3a | >20.0 | |
| 6a | 0.0002 | −77.9 |
| 8a | 0.0005 | −92.2 |
| 9a | >20.0 | |
| 10a | >20.0 | |
| 13a | >20.0 | |

TABLE 5-continued

Degradation of BRD4 in EoL-1 Cells

| Compound | Average $EC_{50}$ (µM) | $S_{inf}$ (%) |
| --- | --- | --- |
| 14a | >20.0 | |
| 15 | >20.0 | |

Example E: Cell Proliferation Assays for BRD4 Targeted Small Molecules and Antibody Conjugates To determine the anti-proliferative effects of small molecule degraders of BRD4, individually or as payload conjugated to an antibody, a standard cell viability assessment protocol was employed. As antibody conjugates were targeted to either STEAP-1 or CLL-1 antigens, cell lines assayed included PC-3-STEAP1 (PC-3 cells stably expressing STEAP-1) and EoL-1.

Culture media used for all cell lines was RPMI-1640 with reduced cysteine concentration (50 µM), plus 10% FBS and antibiotics. Cell seeding density was determined for each line to enable a 6 day treatment with test compounds or antibodies without overgrowth of cells. All incubations were at 37° C. in a humidified $CO_2$ incubator.

On day 1, cells were harvested by either centrifugation of suspension cells or by Acutase treatment of adherent cells, then seeded in 50 µL of fresh culture media in 384 well black/clear tissue culture plates at the following densities: PC-3-STEAP-1 (400 cells/well) and EoL-1 (2500 cells/well). Treatment with various concentrations of test molecules was started the following day by the addition of either small molecules diluted in DMSO or antibody conjugates in dilution buffer (20 mM histidine acetate, 240 mM sucrose, 0.02% polysorbate 20, pH 5.5), using an Echo acoustic dispenser (Labcyte).

After 6 days of treatment with the test molecules, assay plates were allowed to equilibrate to room temperature and the level of viable cells was assessed by addition of 40 µL of CellTiterGlo (Promega) according to manufacturer's instruction and luminescence read on an Envision instrument (PerkinElmer).

Level of luminescence is a direct correlation to ATP from the lysed cells and reflects the number of viable cells. Reduced signal as compared to control wells (DSMO or antibody diluent) was used as an indication of inhibition of proliferation or of cell death due to loss of BRD4.

The results are set forth in Table 6.

TABLE 6

Cell Proliferation Assays

| Compound | PC3-Steap1 ATP Average $IC_{50}$ | EoL-1 ATP Average $IC_{50}$ |
| --- | --- | --- |
| A | 0.4100 | 0.0873 |
| 1a | 0.0066 | 0.0022 |
| 1b | 0.1845 | 0.3002 |
| 2a | 0.0420 | 0.0098 |
| 3a | 0.2120 | 0.0420 |
| 4a | 0.3127 | 0.0530 |
| 5a | 0.7790 | 0.1867 |
| 6a | 0.0064 | 0.0017 |
| 7a | 0.2130 | 0.0439 |
| 8a | 0.0177 | 0.0052 |
| 9a | 0.4490 | 0.0442 |
| 10a | 0.0653 | 0.0101 |

TABLE 6-continued

Cell Proliferation Assays

| Compound | PC3-Steap1 ATP Average IC$_{50}$ | EoL-1 ATP Average IC$_{50}$ |
|---|---|---|
| 12a | 0.1370 | 0.0190 |
| 13a | 0.4975 | 0.1010 |
| 14a | 0.3960 | 0.0611 |
| 15 | 0.1125 | 0.0244 |

Example F: Myc mRNA Assay

Pharmacologic inhibition of MYC is achievable through targeting BET bromodomains through small molecule binder or degrader mechanisms. Such inhibitors may have clinical utility given the widespread pathogenetic role of MYC in cancer (Mertz, J., et al. (2011) "Targeting MYC dependence in cancer by inhibiting BET bromodomains," Proc. Natl. Acad. Sci. USA, 108(40): 16669-16674).

To determine the inhibition of MYC expression, MV-4-11 cells (ATCC) were plated at 10,000 cells per well in 96-well plates in RPMI1640 media supplemented with 10% fetal bovine serum and 2 mM L-glutamine. Test compounds diluted in DMSO were transferred to the cell plates, keeping final DMSO concentration consistent at 0.1%, and incubated for 4 hours at 37° C. Lysis and analysis for MYC expression were carried out using QuantiGene 2.0 reagents (Affymetrix/eBioscience, probe set cat #SA-50182) and following the vendor's instructions. Luminescence was read using an EnVision plate reader (PerkinElmer) and IC$_{50}$s generated in Genedata Screener using a 4-parameter non-linear regression fit.

Bromobinder molecules that potently inhibit, but do not degrade, the target will block up to 80% of the endogenous MYC expression in the MV-4-11 cells. Active degraders that have S$_{inf}$ values less than 60 to 70% may have maximum inhibition of Myc as low as 79%. Effective degraders with S$_{inf}$ values greater than 70% can surpass this and inhibit approximately 85 to 95% of MYC. Thus following the maximum inhibition within this assay provides valuable SAR.

The results are set forth in Table 7.

TABLE 7

Inhibition of MYC expression in MV-4-11 cells

| Compound | Average IC$_{50}$ (µM) | Maximum Inhibition (%) (mean) |
|---|---|---|
| A | 0.0834 | 76.3 |
| 1a | 0.0029 | 89.1 |
| 1b | 0.0675 | 86.6 |
| 2a | 0.0111 | 77.9 |
| 3a | 0.0117 | 78.7 |
| 4a | 0.0198 | 79.4 |
| 5a | 0.1238 | 87.6 |
| 6a | 0.0020 | 88.4 |
| 7a | 0.0257 | 72.9 |
| 8a | 0.0072 | 95.1 |
| 9a | 0.0277 | 78.1 |
| 10a | 0.0071 | 79.3 |
| 11a | 0.0207 | 72.5 |
| 12a | 0.0126 | 73.3 |
| 13a | 0.1625 | 71.6 |
| 14a | 0.0972 | 73.6 |
| 15 | 0.0072 | 75.7 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compound of Formula (I):

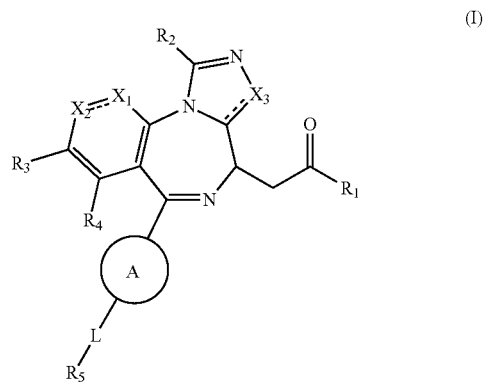

or a pharmaceutically acceptable salt or an enantiomer thereof, wherein:

$X_1$ is S or C(R$_{11}$);

$X_2$ is absent or C(R$_{12}$);

$X_3$ is N or O;

═════ is a single or a double bond;

wherein when $X_1$ is C(R$_{11}$), ═════ is a double bond between $X_1$ and $X_2$, and when $X_3$ is N, ═════ is a double bond between $X_3$ and the rest of the molecule;

ring A is phenyl or a 6-membered heteroaryl, wherein ring A is optionally further substituted with one or more substituents selected from the group consisting of halo, hydroxy, —C$_{1-3}$-alkyl, —O—C$_{1-3}$-alkyl, and —NH$_2$;

$R_1$ is —O—C$_1$-C$_6$-alkyl, or —N(R$_8$)(R$_9$), wherein $R_8$ and $R_9$ are independently selected from the group consisting of H, C$_1$-C$_4$-alkyl, and phenyl, wherein the phenyl is optionally substituted with R$_{10}$, wherein R$_{10}$ is hydroxyl;

$R_2$ is methyl;

$R_3$, $R_4$, $R_{11}$, and $R_{12}$ are each independently selected from the group consisting of H, methyl, and methoxy;

L is C$_1$-C$_4$ alkylene, C$_2$-C$_4$ alkenylene or C$_2$-C$_4$ alkynylene; and $R_5$ is selected from the group consisting of —N(R$_6$)(R$_7$); —C(H)(CH$_3$)—NH$_2$; —C(CH$_3$)$_2$—NH$_2$; methyl; and hydroxyl, wherein R$_6$ and R$_7$ are independently selected from the group consisting of H, methyl, —C(NH)—NH$_2$, hydroxy, and —C(O)CH$_3$.

2. The compound of claim 1, or a pharmaceutically acceptable salt or an enantiomer thereof, wherein ring A is selected from the group consisting of optionally substituted phenyl, optionally substituted pyridinyl, and optionally substituted pyrimidinyl.

3. The compound of claim 2, or a pharmaceutically acceptable salt or an enantiomer thereof, wherein ring A is phenyl.

4. The compound of claim 1, wherein the compound is of Formula (IV-1):

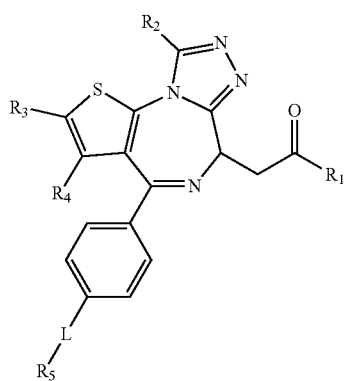

(IV-1)

or a pharmaceutically acceptable salt or an enantiomer thereof.

5. The compound of claim 1, wherein the compound is of Formula (IX-1):

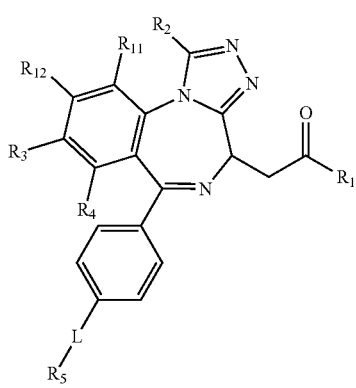

(IX-1)

or a pharmaceutically acceptable salt or an enantiomer thereof.

6. The compound of claim 1, or a pharmaceutically acceptable salt or an enantiomer thereof, wherein $R_1$ is —O—$C_1$-$C_4$-alkyl.

7. The compound of claim 6, or a pharmaceutically acceptable salt or an enantiomer thereof, wherein $R_1$ is —O-t-butyl.

8. The compound of claim 6, or a pharmaceutically acceptable salt or an enantiomer thereof, wherein $R_1$ is —O—$CH_3$.

9. The compound of claim 1, or a pharmaceutically acceptable salt or an enantiomer thereof, wherein $R_1$ is —N($R_8$)($R_9$).

10. The compound of claim 9, or a pharmaceutically acceptable salt or an enantiomer thereof, wherein $R_8$ and $R_9$ are each H.

11. The compound of claim 9, or a pharmaceutically acceptable salt or an enantiomer thereof, wherein $R_8$ is H and $R_9$ is $C_1$-$C_4$ alkyl.

12. The compound of claim 11, or a pharmaceutically acceptable salt or an enantiomer thereof, wherein $R_8$ is H and $R_9$ is ethyl.

13. The compound of claim 9, or a pharmaceutically acceptable salt or an enantiomer thereof, wherein $R_8$ is H and $R_9$ is phenyl substituted with $R_{10}$.

14. The compound of claim 13, or a pharmaceutically acceptable salt or an enantiomer thereof, wherein $R_{10}$ is hydroxy, and $R_9$ and $R_{10}$, taken together, are

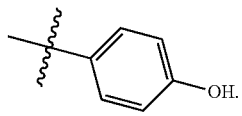 [SMILES: *c1ccc(O)cc1]

15. The compound of claim 1, or a pharmaceutically acceptable salt or an enantiomer thereof, wherein $R_3$ and $R_4$ are each methyl.

16. The compound of claim 1, or a pharmaceutically acceptable salt or an enantiomer thereof, wherein $R_3$ and $R_4$ are each H.

17. The compound of claim 1, or a pharmaceutically acceptable salt or an enantiomer thereof, wherein $R_3$ is methoxy and $R_4$ is H.

18. A pharmaceutical composition comprising a compound of claim 1, or a pharmaceutically acceptable salt or an enantiomer thereof, and one or more pharmaceutically acceptable excipients.

19. A method of treating a bromodomain-mediated disease or disorder in a human in need thereof, the method comprising administering to said human an effective amount of a compound of claim 1, or a pharmaceutically acceptable salt or an enantiomer thereof.

20. The method of claim 19, wherein the disease is a cancer.

21. A method of degrading a bromodomain-containing protein in a cell, the method comprising exposing the cell to a composition comprising an effective amount of the compound of claim 1, or a pharmaceutically acceptable salt or an enantiomer thereof, wherein the compound or pharmaceutically acceptable salt or enantiomer thereof effectuates the degradation of the bromodomain-containing protein.

22. The method of claim 21, wherein the bromodomain-containing protein is bromodomain-containing protein 4 (BRD4).

23. The compound of claim 1, or a pharmaceutically acceptable salt or an enantiomer thereof, wherein L-$R_5$ is selected from the group consisting of:

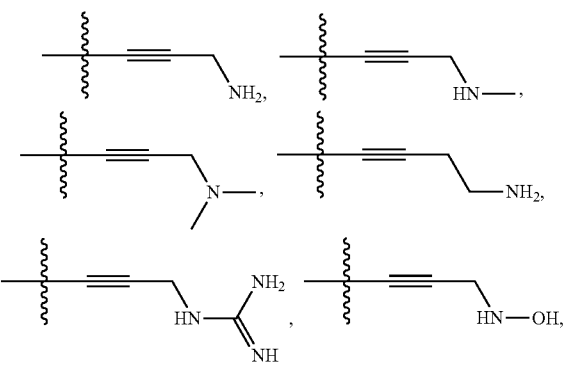

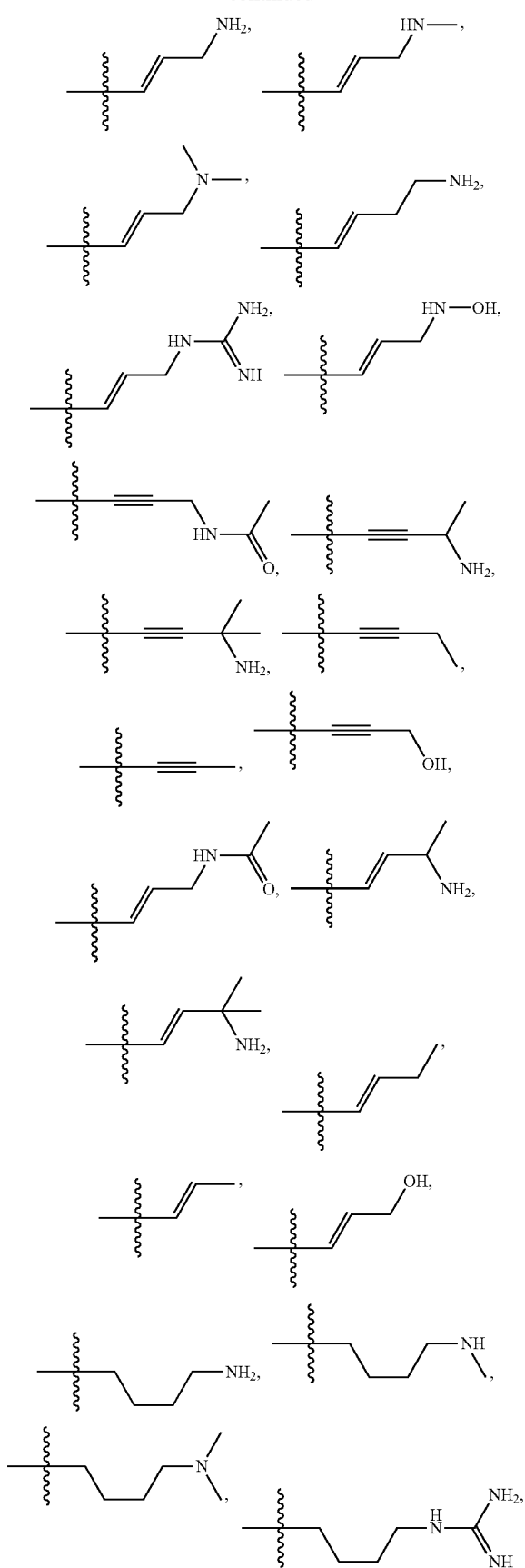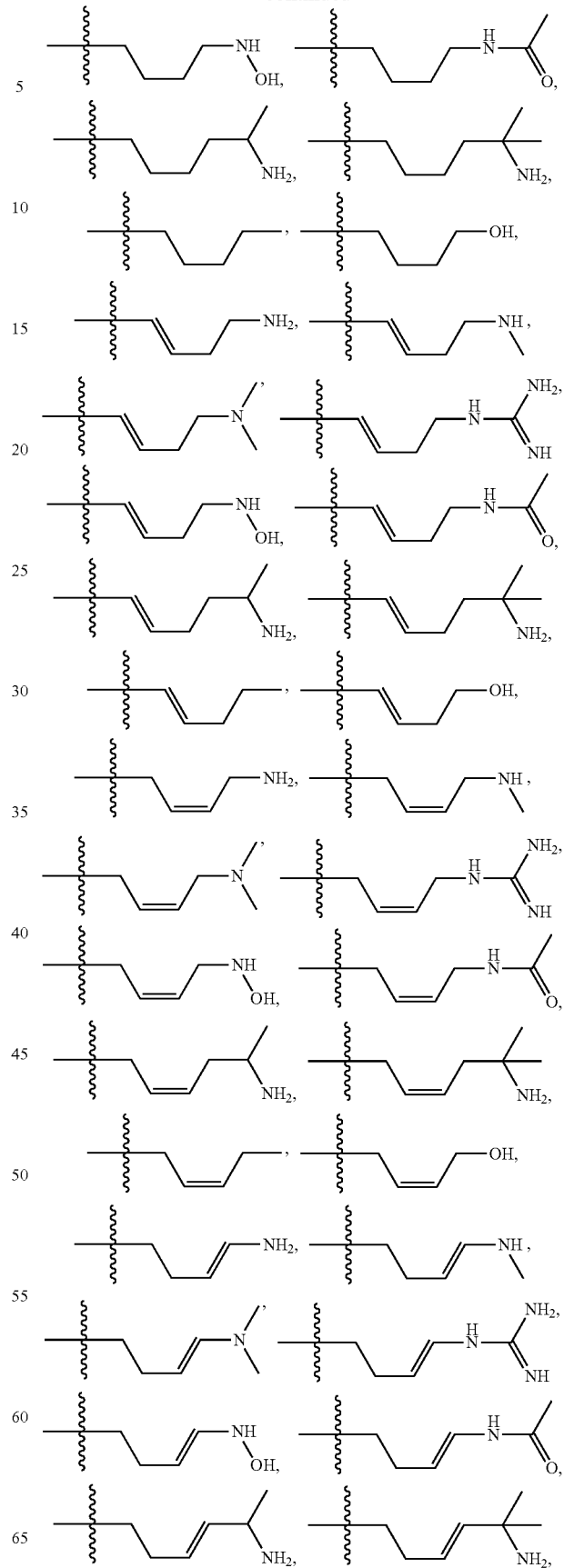

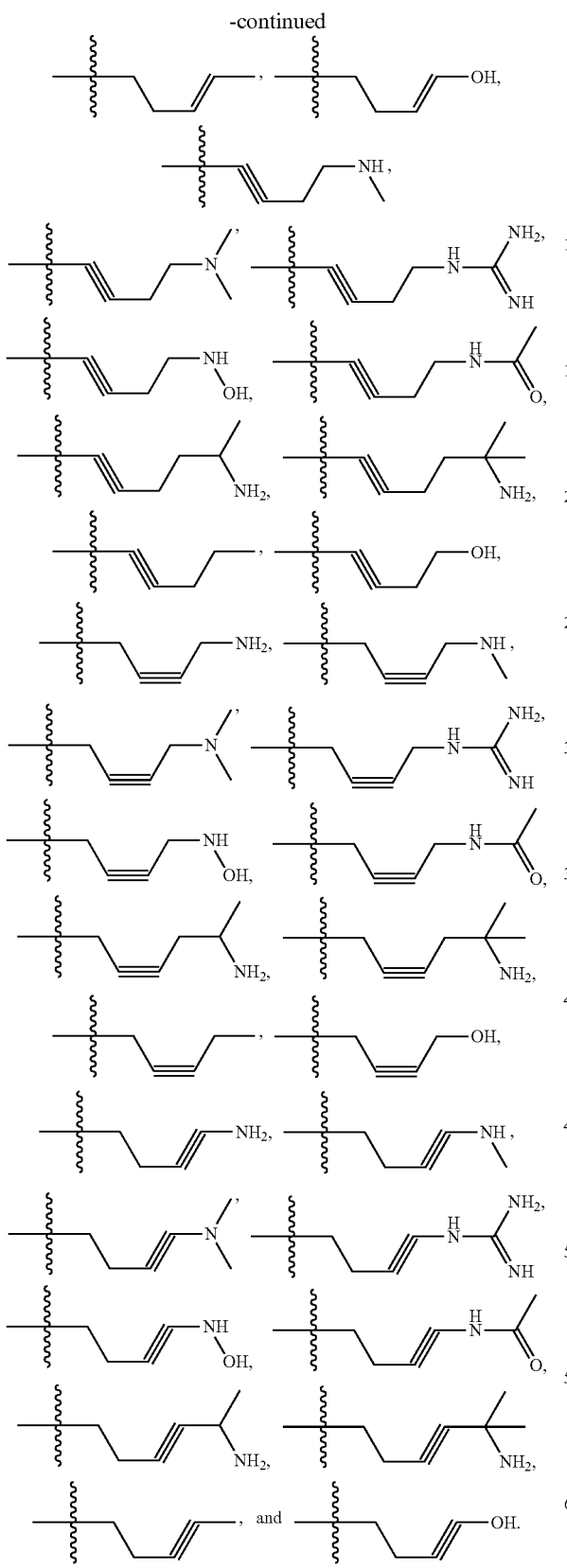

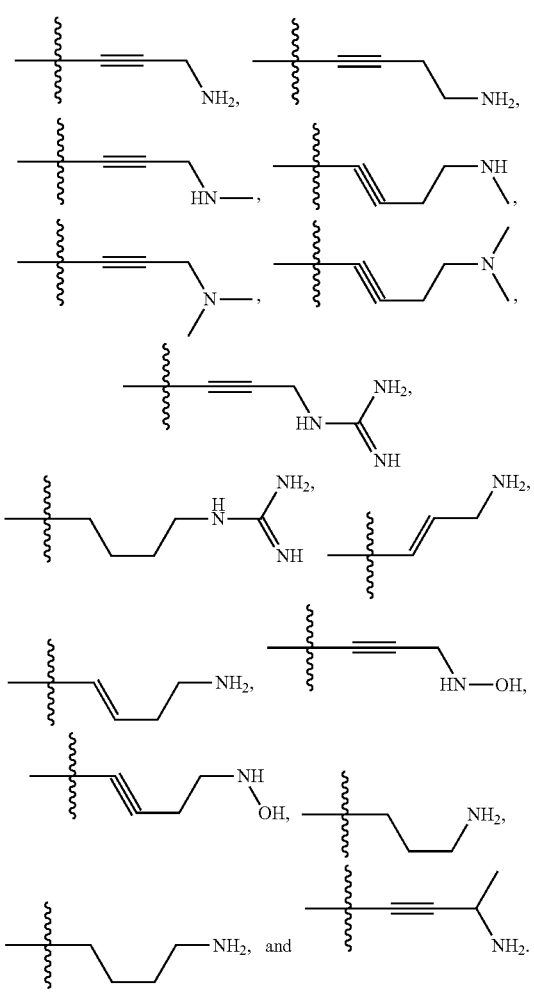

24. The compound of claim 1, or a pharmaceutically acceptable salt or an enantiomer thereof, wherein L is $C_2$-$C_4$ alkylene.

25. The compound of claim 1, or a pharmaceutically acceptable salt or an enantiomer thereof, wherein $R^5$ is selected from the group consisting of $CH_3$, OH, $NH_2$, $NH(CH_3)$, $N(CH_3)_2$, NH(OH), NH—C(NH)($NH_2$), NH—C(O)($CH_3$), $CH(CH_3)$—$NH_2$ and $C(CH_3)_2$—$NH_2$.

26. The compound of claim 1, or a pharmaceutically acceptable salt or an enantiomer thereof, wherein $R^5$ is selected from the group consisting of $NH_2$, $NH(CH_3)$, $N(CH_3)_2$, NH(OH), $CH(CH_3)$—$NH_2$ and NH—C(NH)($NH_2$).

27. The compound of claim 1, or a pharmaceutically acceptable salt or an enantiomer thereof, wherein L-$R_5$ is selected from the group consisting of:

28. The compound of claim 1, wherein the compound is selected from the group consisting of:
  tert-butyl 2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate,
  tert-butyl 2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate,
  tert-butyl 2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate,
  tert-butyl 2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate tert-butyl (E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate, tert-butyl 2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(3-(hydroxyamino) prop-1-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(3-aminopropyl)phenyl)-2,3,9-trimethyl-6H-thieno[3,2-f][1,2,4]triazolo[4,3-a][1,4]diazepin-6-yl)acetate, tert-butyl 2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(3-aminobut-1-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(but-1-yn-1-yl)phenyl)-2,3,9-trimethyl-6H-thieno[3,2-f][1,2,4]triazolo[4,3-a][1,4]diazepin-6-yl)acetate, tert-butyl 2-(2,3,9-trimethyl-4-(4-(prop-1-yn-1-yl)phenyl)-6H-thieno[3,2-f][1,2,4]triazolo[4,3-a][1,4]diazepin-6-yl)acetate, tert-butyl 2-(4-(4-(4-aminobutyl)phenyl)-2,3,9-trimethyl-6H-thieno[3,2-f][1,2,4]triazolo[4,3-a][1,4]diazepin-6-yl)acetate, tert-butyl (E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate, tert-butyl (E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate, tert-butyl (Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate, tert-butyl (E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate, tert-butyl (E)-2-(4-(4-(4-(hydroxyamino)but-2-en-1-yl)phenyl)-2,3,9-trimethyl-6H-thieno[3,2-f][1,2,4]triazolo[4,3-a][1,4]diazepin-6-yl)acetate, tert-butyl (Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate, tert-butyl 2-(4-(4-(4-(hydroxyamino)butyl)phenyl)-2,3,9-trimethyl-6H-thieno[3,2-f][1,2,4]triazolo[4,3-a][1,4]diazepin-6-yl)acetate, tert-butyl 2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate, tert-butyl 2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate, and tert-butyl 2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate, or a pharmaceutically acceptable salt or an enantiomer thereof.

29. The compound of claim 1, wherein the compound is selected from the group consisting of:

tert-butyl (S)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate, tert-butyl (R)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate, tert-butyl (S)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate, tert-butyl (S,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate, tert-butyl (R,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(3-hydroxyprop-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(3-(hydroxyamino) prop-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(3-(hydroxyamino) prop-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(3-aminopropyl)phenyl)-2,3,9-trimethyl-6H-thieno[3,2-f][1,2,4]triazolo[4,3-a][1,4]diazepin-6-yl)acetate, tert-butyl (R)-2-(4-(4-(3-aminopropyl)phenyl)-2,3,9-trimethyl-6H-thieno[3,2-f][1,2,4]triazolo[4,3-a][1,4]diazepin-6-yl)acetate, tert-butyl (S)-2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(3-acetamidoprop-1-yn-1-yl)phenyl)-2,3,9-trimethyl-6H-thieno[3,2-f][1,2,4]triazolo[4,3-a][1,4]diazepin-6-yl)acetate, tert-butyl 2-((6S)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate, tert-butyl 2-((6R)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(3-amino-3-methylbut-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(but-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(but-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(2,3,9-trimethyl-4-(4-(prop-1-yn-1-yl)phenyl)-6H-thieno[3,2-f][1,2,4]triazolo[4,3-a][1,4]diazepin-6-yl)acetate, tert-butyl (R)-2-(2,3,9-trimethyl-4-(4-(prop-1-yn-1-yl)phenyl)-6H-thieno[3,2-f][1,2,4]triazolo[4,3-a][1,4]diazepin-6-yl)acetate, tert-butyl (S)-2-(4-(4-(4-aminobutyl)phenyl)-2,3,9-trimethyl-6H-thieno[3,2-f][1,2,4]triazolo[4,3-a][1,4]diazepin-6-yl)acetate, tert-butyl (R)-2-(4-(4-(4-aminobutyl)phenyl)-2,3,9-trimethyl-6H-thieno[3,2-f][1,2,4]triazolo[4,3-a][1,4]diazepin-6-yl)acetate, tert-butyl (S,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate, tert-butyl (R,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate, tert-butyl (S,E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate, tert-butyl (R,E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate, tert-butyl (S,Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate, tert-butyl (R,Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate, tert-butyl (S,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate, tert-butyl (R,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate, tert-butyl (S,E)-2-(4-(4-(4-(hydroxyamino)but-2-en-1-yl)phenyl)-2,3,9-trimethyl-6H-thieno[3,2-f][1,2,4]triazolo[4,3-a][1,4]diazepin-6-yl)acetate tert-butyl (R,E)-2-(4-(4-(4-(hydroxyamino)but-2-en-1-yl)phenyl)-2,3,9-trimethyl-6H-thieno[3,2-f][1,2,4]triazolo[4,3-a][1,4]diazepin-6-yl)acetate, tert-butyl (S,Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate, tert-butyl (R,Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(4-(hydroxyamino)butyl)phenyl)-2,3,9-trimethyl-6H-thieno[3,2-f][1,2,4]triazolo[4,3-a][1,4]diazepin-6-yl)acetate, tert-butyl (R)-2-(4-(4-(4-(hydroxyamino)butyl)phenyl)-2,3,9-trimethyl-6H-thieno[3,2-f][1,2,4]triazolo[4,3-a][1,4]diazepin-6-yl)acetate, tert-butyl (S)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate, tert-butyl (R)-2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate, tert-butyl (S)-2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate, and tert-butyl (R)-2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate, or a pharmaceutically acceptable salt or an enantiomer thereof.

30. The compound of claim 1, wherein the compound is selected from the group consisting of:

tert-butyl (S)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate;

tert-butyl (R)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate;

tert-butyl (S)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate;

tert-butyl (S)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate;

tert-butyl (S)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate;

tert-butyl (S)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate;

tert-butyl (S,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate;

tert-butyl (S)-2-(4-(4-(3-(hydroxyamino) prop-1-yn-1-yl)phenyl)-2,3,9-trimethyl-6H-thieno[3,2-f][1,2,4]triazolo[4,3-a][1,4]diazepin-6-yl)acetate;

tert-butyl (S)-2-(4-(4-(3-aminopropyl)phenyl)-2,3,9-trimethyl-6H-thieno[3,2-f][1,2,4]triazolo[4,3-a][1,4]diazepin-6-yl)acetate;

tert-butyl 2-((6S)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-aminobutyl)phenyl)-2,3,9-trimethyl-6H-thieno[3,2-f][1,2,4]triazolo[4,3-a][1,4]diazepin-6-yl)acetate;
tert-butyl (R)-2-(4-(4-(4-aminobutyl)phenyl)-2,3,9-trimethyl-6H-thieno[3,2-f][1,2,4]triazolo[4,3-a][1,4]diazepin-6-yl)acetate;
tert-butyl (S,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate;
tert-butyl (R,E)-2-(4-(4-(4-aminobut-1-en-1-yl)phenyl)-2,3,9-trimethyl-6H-thieno[3,2-f][1,2,4]triazolo[4,3-a][1,4]diazepin-6-yl)acetate;
tert-butyl (S,E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate;
tert-butyl (R,E)-2-(4-(4-(4-aminobut-2-en-1-yl)phenyl)-2,3,9-trimethyl-6H-thieno[3,2-f][1,2,4]triazolo[4,3-a][1,4]diazepin-6-yl)acetate;
tert-butyl (S,Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate;
tert-butyl (R,Z)-2-(4-(4-(4-aminobut-3-en-1-yl)phenyl)-2,3,9-trimethyl-6H-thieno[3,2-f][1,2,4]triazolo[4,3-a][1,4]diazepin-6-yl)acetate;
tert-butyl (S,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate;
tert-butyl (R,E)-2-(4-(4-(4-(hydroxyamino)but-1-en-1-yl)phenyl)-2,3,9-trimethyl-6H-thieno[3,2-f][1,2,4]triazolo[4,3-a][1,4]diazepin-6-yl)acetate;
tert-butyl (R,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate;
tert-butyl (R,E)-2-(4-(4-(4-(hydroxyamino)but-2-en-1-yl)phenyl)-2,3,9-trimethyl-6H-thieno[3,2-f][1,2,4]triazolo[4,3-a][1,4]diazepin-6-yl)acetate;
tert-butyl (S,Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate;
tert-butyl (R,Z)-2-(4-(4-(4-(hydroxyamino)but-3-en-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-(hydroxyamino)butyl)phenyl)-2,3,9-trimethyl-6H-thieno[3,2-f][1,2,4]triazolo[4,3-a][1,4]diazepin-6-yl)acetate;
tert-butyl (R)-2-(4-(4-(4-(hydroxyamino)butyl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate;
tert-butyl (R)-2-(4-(4-(4-(hydroxyamino)but-1-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate;
tert-butyl (R)-2-(4-(4-(4-(hydroxyamino)but-2-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate;
tert-butyl (R)-2-(4-(4-(4-(hydroxyamino)but-3-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate;
tert-butyl (R)-2-(4-(4-(4-aminobut-2-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate; and
tert-butyl (R)-2-(4-(4-(4-aminobut-3-yn-1-yl)phenyl)-2,3,9-trimethyl-6H-thieno[3,2-f][1,2,4]triazolo[4,3-a][1,4]diazepin-6-yl)acetate;
or a pharmaceutically acceptable salt or an enantiomer thereof.

31. The compound of claim 30, wherein the compound is selected from the group consisting of:
tert-butyl (S)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate;
tert-butyl (R)-2-(4-(4-(3-aminoprop-1-yn-1-yl)phenyl)-2,3,9-trimethyl-6H-thieno[3,2-f][1,2,4]triazolo[4,3-a][1,4]diazepin-6-yl)acetate;
tert-butyl (S)-2-(2,3,9-trimethyl-4-(4-(3-(methylamino)prop-1-yn-1-yl)phenyl)-6H-thieno[3,2-f][1,2,4]triazolo[4,3-a][1,4]diazepin-6-yl)acetate;
tert-butyl (S)-2-(4-(4-(3-(dimethylamino)prop-1-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(4-aminobut-1-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(3-guanidinoprop-1-yn-1-yl)phenyl)-2,3,9-trimethyl-6H-thieno[3,2-f][1,2,4]triazolo[4,3-a][1,4]diazepin-6-yl)acetate;
tert-butyl (S,E)-2-(4-(4-(3-aminoprop-1-en-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(3-(hydroxyamino) prop-1-yn-1-yl)phenyl)-2,3,9-trimethyl-6H-thieno[3,2-f][1,2,4]triazolo[4,3-a][1,4]diazepin-6-yl)acetate;
tert-butyl (S)-2-(4-(4-(3-aminopropyl)phenyl)-2,3,9-trimethyl-6H-thieno[3,2-f][1,2,4]triazolo[4,3-a][1,4]diazepin-6-yl)acetate; and
tert-butyl 2-((6S)-4-(4-(3-aminobut-1-yn-1-yl)phenyl)-2,3,9-trimethyl-6H-thieno[3,2-f][1,2,4]triazolo[4,3-a][1,4]diazepin-6-yl)acetate;
or a pharmaceutically acceptable salt or an enantiomer thereof.

* * * * *